US011827876B2

(12) United States Patent
Alphey et al.

(10) Patent No.: US 11,827,876 B2
(45) Date of Patent: Nov. 28, 2023

(54) SELF-LIMITING, SEX-SPECIFIC GENE AND METHODS OF USING

(71) Applicant: OXITEC LTD., Abingdon (GB)

(72) Inventors: Luke Alphey, Pirbright (GB); Tarig Dafa'alla, Abingdon (GB); Amandine Collado, Abingdon (GB); Simon Warner, Abingdon (GB); Kelly Matzen, Abingdon (GB); Sian Spinner, Abingdon (GB)

(73) Assignee: OXITEC LTD., Abingdon (GB)

( * ) Notice: Subject to any disclaimer, the term of this patent is extended or adjusted under 35 U.S.C. 154(b) by 1295 days.

(21) Appl. No.: 16/324,078

(22) PCT Filed: Aug. 9, 2017

(86) PCT No.: PCT/IB2017/001128

§ 371 (c)(1),
(2) Date: Feb. 7, 2019

(87) PCT Pub. No.: WO2018/029534

PCT Pub. Date: Feb. 15, 2018

(65) Prior Publication Data

US 2020/0407748 A1 Dec. 31, 2020

Related U.S. Application Data

(60) Provisional application No. 62/420,270, filed on Nov. 10, 2016, provisional application No. 62/374,415, filed on Aug. 12, 2016.

(51) Int. Cl.
*A01K 67/033* (2006.01)
*C12N 15/85* (2006.01)

(52) U.S. Cl.
CPC ...... *C12N 15/8509* (2013.01); *A01K 67/0339* (2013.01); *A01K 2227/706* (2013.01); *A01K 2267/02* (2013.01); *C12N 2830/003* (2013.01); *C12N 2840/44* (2013.01)

(58) Field of Classification Search
CPC ................................................. C12N 15/8509
See application file for complete search history.

(56) References Cited

U.S. PATENT DOCUMENTS 5,254,801 A 10/1993 Dotson et al.
5,278,057 A 1/1994 Jorgense
5,670,353 A 9/1997 Ahlquist et al.
5,674,747 A 10/1997 Hammock et al.
5,773,697 A 6/1998 Tomes et al.
5,851,796 A 12/1998 Schatz
5,977,441 A 11/1999 Oliver et al.
6,200,800 B1 3/2001 Choulika et al.
6,235,278 B1 5/2001 Miller et al.
6,338,040 B1 1/2002 Buman et al.
6,962,810 B2 11/2005 Fraser et al.
7,998,475 B2 8/2011 Alphey
8,124,404 B2 2/2012 Alphey
8,704,041 B2 4/2014 Gordon-Kamm et al.
9,121,036 B2 9/2015 Alphey
9,125,388 B2 9/2015 Alphey et al.
9,133,477 B2 9/2015 Alphey
9,487,801 B2 11/2016 Alphey
9,970,025 B2 5/2018 Alphey
10,059,961 B2 8/2018 Alphey
10,844,402 B2 11/2020 Alphey
10,941,416 B2 3/2021 Alphey
2003/0150007 A1 8/2003 Savakis et al.
2003/0213005 A1 11/2003 Alphey et al.
2004/0082032 A1 4/2004 Bovi et al.
2005/0221430 A1 10/2005 Prentice
2006/0212949 A1 9/2006 Alphey
2006/0242717 A1 10/2006 Alphey
2006/0275276 A1 12/2006 Alphey
2007/0056051 A1 3/2007 Alphey
2008/0115233 A1 5/2008 Alphey et al.
2009/0170793 A1 7/2009 Gaur
2009/0183269 A1 7/2009 Alphey
2013/0298266 A1 11/2013 Alphey et al.
2015/0143552 A1 5/2015 Alphey
2016/0044902 A1 2/2016 Alphey et al.
2016/0060651 A1 3/2016 Alphey
2016/0122780 A1 5/2016 Alphey
2017/0009253 A1 1/2017 Alphey
2017/0188559 A1 7/2017 Koukidou et al.
(Continued)

FOREIGN PATENT DOCUMENTS

CA 2012311 C 6/2003
EP 636310 A1 2/1995
(Continued)

OTHER PUBLICATIONS

Salvemini et al. (2011, BMC Evol. Biol., vol. 11:41, pp. 1-19) (Year: 2011).*
Adelman, "Formation and loss of large, unstable tandem arrays of the piggyBac transposable element in the yellow ever mosquito, Aedes aegypti", Transgenic Res, vol. 13, No. 5, 2004, pp. 411-425.
Alignment of SEQ ID No. 22 of D1 (WO 2005/012534) with tTAV, Jul. 4, 2014.
Allen et al., "Flight muscle-specific expression of acI88F: GFP in transgenic Culex quinauefasciatus Say (Diptera: Culicidae)", Parasitology Int vol. 53, No. 4, 2004, pp. 307-317.
Allen et al., "PiggyBac transformation of the New World screwworm, Cochliomyia hominivorax, produces multiple distinct mutant strains", Med. Vet. Entomol vol. 18, Mar. 2004, pp. 1-9.
(Continued)

*Primary Examiner* — Anoop K Singh
*Assistant Examiner* — David A Montanari
(74) *Attorney, Agent, or Firm* — MORRISON & FOERSTER LLP

(57) ABSTRACT

The invention provides a splice control module for sex-specific splicing and expression of a gene of interest. In certain embodiments, a dsx-based splice control module is used to express a lethal gene in an insect that is spliced in a sex-specific manner to impart lethality to female insects but not male insects.

11 Claims, 10 Drawing Sheets

Specification includes a Sequence Listing.

(56) References Cited

U.S. PATENT DOCUMENTS

| | | | |
|---|---|---|---|
| 2018/0251785 | A1 | 9/2018 | Alphey |
| 2018/0312870 | A1 | 11/2018 | Alphey |
| 2021/0137083 | A1 | 5/2021 | Koukidou et al. |
| 2021/0324409 | A1 | 10/2021 | Turkle et al. |
| 2022/0098597 | A1 | 3/2022 | Joyce et al. |

FOREIGN PATENT DOCUMENTS

| | | | | |
|---|---|---|---|---|
| EP | 955364 | A2 | 11/1999 | |
| EP | 3152311 | B1 | 8/2019 | |
| GB | 2355459 | A | 4/2001 | |
| GB | 2404382 | A | 2/2005 | |
| GB | 2443186 | A | 4/2008 | |
| GB | 2500113 | A | 9/2013 | |
| JP | 2008-67678 | A | 3/2008 | |
| WO | WO-1990008830 | A1 | 8/1990 | |
| WO | WO-1994003619 | A2 | 2/1994 | |
| WO | WO-1996004393 | A2 | 2/1996 | |
| WO | WO-1996024605 | A1 | 8/1996 | |
| WO | WO-1997030162 | A1 | 8/1997 | |
| WO | WO-1998008960 | A1 | 3/1998 | |
| WO | WO-1999010488 | A1 | 3/1999 | |
| WO | WO-2000073510 | A1 | 12/2000 | |
| WO | WO-2001039599 | A2 | 6/2001 | |
| WO | WO-2001059088 | A2 | 8/2001 | |
| WO | WO-2001091802 | A1 | 12/2001 | |
| WO | WO-2002046444 | A2 | 6/2002 | |
| WO | WO-2002101061 | A2 | 12/2002 | |
| WO | WO-2004044150 | A2 | 5/2004 | |
| WO | WO-2004098278 | A1 | 11/2004 | |
| WO | WO-2004108933 | A1 | 12/2004 | |
| WO | WO-2005003364 | A2 | 1/2005 | |
| WO | WO-2005012534 | A1 | 2/2005 | |
| WO | WO-2007091099 | A1 * | 8/2007 | ......... A01K 67/0335 |
| WO | WO-2008134068 | A2 | 11/2008 | |
| WO | WO-2009016627 | A1 | 2/2009 | |
| WO | WO-2009115569 | A1 | 9/2009 | |
| WO | WO-2009157771 | A2 | 12/2009 | |
| WO | WO-2013131920 | A1 | 9/2013 | |
| WO | WO-2014135604 | A1 | 9/2014 | |
| WO | WO-2015185933 | A1 | 12/2015 | |
| WO | WO-2018029534 | A1 | 2/2018 | |
| WO | WO-2019186175 | A1 | 10/2019 | |
| WO | WO-2020035673 | A1 | 2/2020 | |

OTHER PUBLICATIONS

Allen et al., "Stable, germ-line transformation of Culex quinquefasciatus (Diptera: Culicidae)", J Med Entomol vol. 38 No.5, 2001, pp. 701-710.

Alphey et al., "Dominant Lethality and Insect Population Control", Mol. Biochem Parasitol. vol. 121 No. 2, May 2002, p. 173-178.

Alphey et al., "Malaria control with genetically manipulated insect vectors", Science vol. 298, Oct. 4, 2002, pp. 119-121.

Alphey et al., "Managing Insecticide Resistance by Mass Release of Engineered Insects", J Econ. Entomol, vol. 100, No. 5, 2007, pp. 1642-1649.

Alphey et al., "Modeling resistance to genetic control of insects", Journal of Theoretical Biology, vol. 270, 2011, pp. 12-55.

Alphey et al., (2002). "Re-engineering the sterile insect technique," Insect Biochem Mol Biol., 32:1243-1247. Abstract Only.

Alphey, "Engineering Insects for the Sterile Insect Technique," in: Area-wide Control of Insect Pests: from Research to Field Implementation, Vreysen et al., (eds.), Dordrecht, The Netherlands, Springer (2007) pp. 51-60.

Ant et al., "Control of the olive fruit fly using genetics-enhanced sterile insect technique", BMC Biology vol. 10, No. 51, 2012, 8 pages.

Arama et al., "Caspase activity and a specific cytochrome Care required for sperm differentiation in *Drosophila*", Dev Cell vol. 4, No. 5, May 1, 2003, pp. 687-697.

Arribas et al., "The ubiquitin genes in D. melanogaster: transcription and polymorphism", Biochimica et Biophysica Acta, vol. 868, 1986, pp. 119-127.

Arya et al., "Basic principles of real-time quantitative PCR", Expert Rev Mol Diagn, vol. 5, No. 2, 2005, pp. 209-219.

Atkinson et al., "Genetic transformation systems in insects", Annu Rev Entomol vol. 46, Jan. 2001, pp. 317-346.

Atkinson et al., "Hermes and other hAT Elements as Gene Vectors in Insects", Insect Transgenesis: Methods and Applications, Hadler et al. {eds.), Boca Raton CRC Press, 2000, pp. 219-235.

Barreau et al., "Post-Meiotic Transcription in *Drosophila* Testes", Development, vol. 135, No. 11, 2008, pp. 1897-1902.

Bauer Dumont et al., "Recurrent positive selection at bgcn, a key determinant of germ line differentiation, does not appear to be driven by simple coevolution with its partner protein barn", Mol Biol Evol vol. 24 No.1, 2007, pp. 182-191.

Beall et al., "Discovery of tMAC: a *Drosophila* testis-specific meiotic arrest complex paraloqous to Myb-Muv B", Genes Dev vol. 21, No. 8, 2007, pp. 904-919.

Bello et al., "Spatial and temporal targeting of gene expression in *Drosophila* by means of a tetracycline-dependent transactivator system", Development vol. 125, No. 12, 1998, pp. 2193-2202.

Bennett et al., "Ectopic Expression of Inhibitors of Protein Phosphatase Type 1 (PP1) Can Be Used to Analyze Roles of PP1 in Drosophila Development", Department of Zoology, Oxford University, Oxford OX1 3PS, United Kingdom, Genetics 164, May 2003, pp. 235-245.

Berghammer et al., "A universal marker for transgenic insects", Nature vol. 402, No. 6760, 1999, pp. 370-371.

Beullens et al., "Inactivation of nuclear inhibitory polypeptides of protein phosphatase-1 {NIPP-1) by protein kinase A", J Biol Chem vol. 268, No. 18, 1993, pp. 13172-13177.

Beullens et al., "Molecular determinants of nuclear protein phosphatase-1 regulation by NIPP-1", J Biol Chem, vol. J74, No. 20, 1999, pp. 14053-14061.

Beullens et al., "The isolation of novel inhibitory polypeptides of protein phosphatase 1 from bovine thymus nuclei", J Biol Chem vol. 267, No. 23, 1992, pp. 16538-16544.

Beumer et al., "Efficient gene targeting in Drosophila with zinc-finger nucleases", Genetics, vol. 172, No. 4, 2006, pp. 391-2403.

Bibikova et al., "Targeted chromosomal cleavage and mutagenesis in *Drosophila* using zinc-finger nucleases", Genetics, vol. 161, No. 3, 2002, pp. 1169-1175.

Bieschke et al., "Doxycycline-Induced Transgene Expression During *Drosophila* Development and Aging", Mol. Gen Genel. vol. 258, No. 6, Jun. 1998, pp. 571-579.

Black et al., Why RIDL is not SIT, Trends Parasitol, vol. 27, No. 8, 2001, pp. 362-370.

Blitvich et al., "Developmental- and tissue-specific expression of an inhibitor of apoptosis protein 1 homologue from Aedes triseriatus mosquitos", Insect Molecular Biology, vol. 11, No. 5, 2002, pp. 431-442.

Boudrez et al., "Identification of MYPT1 and NIPP1 as subunits of protein phosphatase 1 in rat liver cytosol", FEBS Letters, vol. 455, 1999, pp. 175-178.

Brand et al., "Ectopic expression in *Drosophila*", Methods Cell Biol, vol. 44, 1994, pp. 635-654.

Brand et al., "Targeted gene expression as a means of altering cell fates and generating dominant phenotypes", Development, vol. 118, No. 2, 1993, pp. 401-415.

Burcin et al., "A regulatory system for target gene expression", Frontiers in Biosc. vol. 3(c), 1998, pp. 1-7.

Burn et al., "Alternative 5C actin transcripts are localized in different patterns during *Drosophila embryogenesis*", Dev Biol, vol. 131, No. 2, 1989, pp. 345-355.

Burt et al., "Site-specific selfish genes as tools for the control and genetic engineering of natural populations", Proc Biol Sci. vol. 270, 2003, pp. 921-928.

Cabrera et al., "Expression Pattern of Gal4 Enhancer Trap Insertions into the bric a brae Locus Generated by p. Element Replacement", Genesis, vol. 34, 2002, pp. 62-65.

Caceres et al., "Mass rearing of temperature sensitive genetic sexing strains in the Mediterranean fruit fly (Ceratitis Capitata)", Genetica, vol. 115, No. 1, 2002, pp. 107-116.

(56) References Cited

OTHER PUBLICATIONS

Cagan et al., "Spermatogenesis: Borrowing the Apoptotic Machinery", Curr Biol, vol. 13, 2003, pp. R600-R602.
Cande et al., "Apoptosis-Inducing Factor (AIF): Key to the Conserved Caspase-Independent Pathways of Cell Death?", Journal of Cell Science, vol. 115, No. 24, 2002, pp. 4727-4734.
Carriere and Tabashnik, "Reversing Insect Adaptation to Transgenic Insecticidal Plants", Proc. R. Soc. Lond. B. vol. 268, 2001, pp. 1475-1480.
Catteruccia et al., "An Anopheles transgenic sexing strain for vector control", Nat Biotechnol, vol. 23, No. 11, J005, pp. 1414-1417.
Catteruccia et al., "Impact of genetic manipulation on the fitness of Anopheles stephensi mosquitoes", Science, vol. 299, No. 5610, 2000, pp. 1225-1227.
Catteruccia et al., "Stable germline transformation of the malaria mosquito Anopheles stephensi", Nature, vol. 105, No. 6789, 2000, pp. 959-962.
Catteruccia et al., "Transgenic technologies to induce sterility", Malaria Journal, vol. 8(SUPP2)S7, 2009.
Cenik et al., "Genome analysis reveals interplay between 5'UTR intrans and nuclear mRNA export for secretory and mitochondrial genes", PLOS Genet, vol. 794:e1001366, 2011.
Cha et al., "Expression of green fluorescent protein in insect larvae and its application for heterologous protein production", Biotechnol Bioena, vol. 56, No. 3, 1997, pp. 239-247.
Chalfie et al., "Green fluorescent protein as a marker for gene expression", Science, vol. 263, No. 5148, 1994, pp. 802-805.
Chen et al., "Apoptotic Activity of REAPER is Distinct from Signaling by the Tumor Necrosis Factor Receptor 1 Death Domain", The Journal of Biological Chemistry, vol. 271, No. 42, 1996, pp. 25735-25737.
Chen et al., "The Use of Modified Tetracycline Regulatory Expression System with Reduced Basal Level to Develop an In Vivo Biopesticide Expression System", Food Science Agriculture Chem. vol. 2, No. 4, Oct. 2000, pp. 20-225.
Cheng et al., "Cellular transformation by Simian Virus 40 and Murine Polyoma Virus T antigens", Semin Cancer Biol, vol. 19, No. 4, 2009, pp. 218-228.
Chintapalli et al., "Using FlyAtlas to identify better *Drosophila* melanogaster models of human disease", Nature Genetics, vol. 39, No. 6, 2007, pp. 715-720.
Cho, "Enhancers", WIREs Dev Biol vol. 1, 2012, pp. 469-478.
Choi et al., "The Baculovirus Transactivator IE1 Binds to Viral Enhancer Elements in the Absence of Insect Cell Factors", Journal of Virology, vol. 69, No. 7, 1995, pp. 4548-4551.
Curtis et al., "Assessment of the impact of potential tetracycline exposure on the phenotype of Aedes aegypti OX513A: Implications for field use", PLOS Neglected Tropical Diseases, vol. 9, No. 8, 2015.
Dafa'alla et al., "Transposon-Free Insertions for Insect Genetic Engineering", Nature Biotechnology, vol. 24, No. 7, Jul. 2006, pp. 820-821.
Dane et al., "The Transformer Gene in Ceratitis Capitata Provides a Genetic Basis for Selecting and remembering the Sexual Fate", Dipartimento di Genetica, Biologia Generale e Molecolare, Development 129, 2002, pp. 3715-3725.
Dapathanos et al., "Sex Separation Strategies: Past Experience and New Approaches", Malaria Journal, vol. 8, J009.
Darker et al., "Functional Interaction between Nuclear Inhibitor of Protein Phosphatase Type 1 (NIPP1) and Protein Phosphatase Type 1 (PP1) in *Drosophila*: Consequences of Overexpression Of NIPP1 in Flies and Suppression by Co-expression of PP1", Biochemical Journal, vol. 368, 2002, pp. 789-797.
Davis et al., "Engineered Underdominance Allows Efficient and Economical Introgression of Traits into Pest Populations", J Theor. Biol., vol. 212, No. 1, 2001, pp. 83-98.
De Valdez et al., "Genetic Elimination of Dengue Vector Mosquitoes", Proceedings of the National Academy of Sciences of the United States of America, vol. 108, No. 12, 2011, 4772-4775.
Definition of "pest" from the Concise Oxford American Dictionary, Concise Oxford American Dictionary, 2006, p. 661.
Deng et al., "A targeted gene silencing technique shows that Drosophila myosin VI is required for egg chamber and imaginal disc morphogenesis", J Cell Science, vol. 112, 1999, pp. 3677-3690.
Deredec et al., "The population genetics of using homing endonuclease genes in vector and pest management", Genetics, vol. 179, No. 4, 2008, pp. 2013-2026.
Derezgasga et al., "Regulation of Transcription of Meiotic Cell Cycle and Terminal Differentiation Genes by the Testis-specific Zn-finger Protein Matotopelli", Development, vol. 131, No. 8, 2004, pp. 1691-1702.
Devault et al., "Biotechnology and new integrated pest management approaches", Nature Biotechnology, vol. 14, 1996, pp. 46-49.
Dhillon, "The melon fruit fly, Bactrocera cucurbitae: A review of its biology and management", J Insect Sci., vol. 5, 2005, 40 Pages.
Diamantidis et al., (2008). "Life-history evolution of an invasive tephritid," J. Appl. Entomol., 132:695-705. Abstract Only.
Dyck et al., "Genetic sexing strains in the Mediterranean Fruit Fly, an example for other species amenable to large- scale rearing for the sterile insect technique", Sterile Insect Technique, Principles and Practice in Area-Wide Integrated Pest Management and The Netherlands, Springer, 2005, pp. 427-451.
Egloff et al., "Structural basis for the recognition of regulatory subunits by the catalytic subunit of protein Phosphatase 1", EMBO J, vol. 16, No. 8, 1997, pp. 1876-1887.
Elick et al., "Analysis of the Cis-Acting DNA Elements Required for piggyback Transposable Element Excision", Mol. Gen. Genet., vol. 255, 1997, pp. 605-610.
Ernst, "Regulation of Sexual Differentiation in Drosophila: Alternative Splicing of the Transformer Primary Transcript Requires Masking of the Non-Specific Acceptor Site in Females", Inaugural Dissertation, Aus Frankfurt I Main, BRO., 1991, 32 pages.
FAO/IAEA/USDA, "Product Quality Control and Shipping Procedures for Sterile Mass-reared Tephritid Fruit Flies", AEA, Vienna, Version 5.0, May 2003, 2 pages.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, DYCK et al., (eds), The Netherlands, Springer (2005) pp. 427-451.
Franz, "Recombination between homologous autosomes in medfly (Ceratitis capitata) males: type-1 recombination and the implications for the stability of genetic sexing strains", Genetica, vol. 116, No. 1, 2012, pp. 73-84.
Fraser, "Insect transgenesis: current applications and future prospects", Annu Rev Entomol, vol. 57, 2012, pp. 267-289.
Fryxell et al., "Autocidal biological control: a general strategy for insect control based on genetic transformation with highly conserved gene", J Econ Entomol, vol. 88, No. 5, 1995, pp. 1221-1232.
Fu et al., "Female-specific flightless phenotype for mosquito control", Proc Natl Acad Sci USA, vol. 107, No. 10, 2010, pp. 4550-4554.
Fu et al., "Female-specific insect lethality engineered using alternative splicing", Nature Biotechnology, vol. 25, No. 3, J007, pp. 353-357.
Fuller, "Spermatogenesis", The Development of *Drosophila melanogaster*, BATE et al., Cold Spring Harbor Laboratory Press, 1993, pp. 71-147.
Funaguma et al., "The Bmdsx transgene including trimmed introns is sex-specifically spliced in tissues of the silkworm, Bombyx mori", Journal of Insect Science (online), vol. 5, No. 17, 2005, pp. 1-6.
Fussenegger et al., "Autoregulated multicistronic expression vectors provide one-step cloning of regulated product gene expression in mammalian cells", Biotechnol. Prog., vol. 13, 1997, pp. 733-740.
Fussenegger et al., "Regulated Multicistronic Expression Technology for Mammalian Metabolic Engineering", Biotechnology, vol. 28, 1998, pp. 111-126.
Fussenegger et al., "Streptogramin-based gene regulation systems for mammalian cells", Nat Biotechnol, vol. 18, No. 11, 2000, pp. 1203-1208.

(56) References Cited

OTHER PUBLICATIONS

Fussenegger et al., "The impact of mammalian gene regulation concepts on functional genomic research, metabolic engineering, and advanced gene therapies", Biotechnol Prog, vol. 17, No. 1, 2001, pp. 1-51.
Fux et al., "Novel Macrolide-Adjustable Bidirectional Expression Modules for Coordinated Expression of Two Different Transgenes in Mice", J Gene Medicine, vol. 5, 2003, pp. 1067-1079.
Ghosh et al., "Transcription factor binding and induced transcription alter chromosomal c-myc replicator activity", Mol gen Biol, vol. 24, No. 23, 2004, pp. 10193-10207.
Gill et al., (1988). "Negative effect of the transcriptional activator GAL4," Nature, 334(6184):721-724.
Gloor et al., "Targeted Gene Replacement in Drosophila Via P Element-Induced Gap Repair", Science, vol. 253, 1991, pp. 1110-1117.
Golovnin et al., "The su(Hw) insulator can disrupt enhancer-promoter interactions when located more than 20 Kilobases away from the Drosophila achaete-scute complex", Mol Cell Biol, vol. 19, No. 5, 1999, pp. 3443-3456.
Gonczy, "Bag-of-marbles and benign genial cell neoplasm act in the germline to restrict proliferation during Drosophila spermatogenesis", Development, vol. 124, No. 21, 1997, pp. 4361-4371.
Gong et al., "A dominant lethal genetic system for autocidal control of the Mediterranean fruit fly", Nat Biotechnol, vol. 23, No. 4, 2005, pp. 453-456.
Gong et al., "Ends—Out, or replacement, gene targeting in *Drosophila*", Proc Nall Acad Sci {USA), vol. 100, No. 5, J003, pp. 2556-2561.
Gonzy-Treboul et al., "Enhancer-Trap Targeting at the Broad-Complex Locus of *Drosophila melanogaster*", Genes Dev. vol. 9, 1995, pp. 1137-1148.
Gossen et al., "Studying gene function in eukaryotes by conditional gene inactivation", Annu Rev Genet, vol. 36, 2002, pp. 153-173.
Gossen et al., "Tetracycline in Biology, Chemistry and Medicine", 2001, pp. 139-157.
Gossen et al., "Tight control of gene expression in mammalian cells by tetracycline- responsive promoters", Proc Natl Acad Sci {USA), vol. 89, No. 12, 1992, pp. 5547-5551.
Graham et al., "Larval diets containing dyes for tagging pink bollworm moth internally", J Econ Entomol, vol. 64, 1971, pp. 376-379.
Great Britain Application No. 1303932.6, filed Mar. 5, 2013, 42 pages.
GSN: AAD40186, Retrieved from the internet: <http://ibis.internal.epo.org/exam/dbfetch.jsp?id=GSN:AAD40186>, Oct. 22, 2002.
GSN: BB010346, Retrieved from the internet: <http://ibis.internal.epo.org/exam/dbfetch.jsp?id=GSN:BB010346>, Nov. 6, 2014.
Guo et al., "Species-specific signals for the splicing of a short *Drosophila* intron in vitro", Mol Cell Biol, vol. 13, No. 02, 1993, pp. 1104-1118.
Hadjieconomou et al., "Flybow: genetic multicolor cell labeling for neural circuit analysis in *Drosophila melanogaster*", Nature Methods, vol. 8, 2011, pp. 260-266.
Hagler et al., "Methods for marking insects: current techniques and future prospects", Annu. Rev. Entomol. vol. 46, 2001, pp. 511-543.
Hagler et al., (1994). "Determining the frequency of heteropteran predation on sweet potato whitefly and pink bollworm using multiple ELISAs," Entomol. Exp. Appl., 72:59-66.
Hagler, "An Alternative to Conventional Insect Marking Procedures; Detection of a Protein Mark on Pink Bollworm by ELISA", Entomologia Experimentalis et Applicata, vol. 103, No. 1, 2002, pp. 1-9.
Han et al., "Enhancer-Driven Membrane Markers for Analysis of Nonautonomous Mechanisms Reveal Neuron-Glia Interactions in *Drosophila*", Proceedings of the National Academy of Sciences, vol. 108, No. 23, Jun. 7, 2011, pp. 9673-9678.
Handler et al., "A Current Prospective on Insect Gene Transformation", Insect Biochemistry and Molecular Biology, vol. 31, No. 2, 2002, pp. 111-128.
Handler et al., "Germline Transformation of *Drosophila melanogaster* with the Piggybac Transposon Vector", Insect Molecular Biology, vol. 8, No. 4, 1999, pp. 449-457.
Handler et al., "Polyubiquitin-Regulated DsRed Marker for Transgenic Insects", Bio Techniques, vol. 31, 2001, pp. 820-828.
Handler et al., "Prospects for Using Genetic Transformation for Improved SIT and New Biocontrol Methods", Genetics, vol. 116, 2002, pp. 137-149.
Handler et al., "The Lepidopteran Transposon Vector, Piggybac, Mediates Germ-Line Transformation in The Mediterranean Fruit Fly", Proceedings of the National Academy of Sciences, vol. 95, 1998, pp. 7520-7525.
Handler et al., "Use of piggyback Transposon for Germ-Line Transformation of Insects", Insect Biochemistry and Molecular Biology, vol. 32, 2002, pp. 1211-1220.
Hansen et al., "Quantifying changes in the rates of forest clearing in Indonesia from 1990 to 2005 using remotely sensed data sets", Environmental Research Letters, vol. 4, 2009, 12 pages.
Hansen et al., (2009). "Genome-Wide Identification of Alternative Splice Forms Down-Regulated by Nonsense-Mediated mRNA Decay in Drosophila," PLOS Genetics, 5(6):e1000525, 14 pages.
Harris et al., "Field performance of engineered male mosquitoes", Nature Biotechnology, vol. 29 (11), November J011, pp. 1034-1037.
Hartl et al., "Gene Linkage and Genetic Mapping", in Essential Genetics, Jones and Bartlett Publishers, Sudbury, Massachussetts, 1999, pp. 126-127.
He et al., "The Actin Gene Family in the Oriental Fruit Fly Bactrocera Dorsalis, Muscle Specific Actins", Insect Biochemistry and Molecular Biology, vol. 24, No. 9, 1994, pp. 891-906.
Heinrich et al., "A Repressible Female-Specific Lethal Genetic System for Making Transgenic Insect Strains Suitable or a Sterile-Release Program", Proceedings of the National Academy of Sciences of the United States of America, vol. 97, Jul. 18, 2000, pp. 8229-8232.
Hendrichs et al., "Strategic Options in using Sterile Insects For Area-Wide Integrated Pest Management", Sterile Insect Technique, Springer, Netherlands, 2005, pp. 563-600.
Heslip et al., "Targeted Transposition at the Vestigial Locus of *Drosophila melanogaster*", Genetics, vol. 138, 1994, p. 1127-1135.
Hiller, "Testis-Specific TAF Homologs Collaborate to Control a Tissue—Specific Transcription Program", Development, vol. 131, 2004, pp. 5297-5308.
Hockemeyer et al., "Genetic Engineering of Human Pluripotent Cells Using TALE Nucleases", Nature Biotechnology, Vo. 28, No. 8, 2011, pp. 731-734.
Hofmann et al., "Rapid Retroviral Delivery of Tetracycline-Inducible Genes in a Single Autoregulatory Cassette", Proceedings of the National Academy of Sciences of the United States of America, vol. 93, 1996, pp. 5185-5190.
Hollenhorst et al., "Expression profiles frame the promoter specificity dilemma of the ETS family of transcription actors", Nucleic Acids Res, vol. 32, No. 18, 2004, pp. 5693-5702.
Hondred et al., "Use of Ubiquitin Fusions to Augment Protein Expression in Transgenic Plants", Plant Physiology, vol. 119, 1999, pp. 713-723.
Horn et al., "A Transgene-Based, Embryo-Specific Lethality System for Insect Pest Management", Nature Biotechnology, vol. 1, 2003, pp. 64-70.
Horn et al., "Fluorescent Transformation Markers for Insect Transgenesis", Insect Biochemistry and Molecular Biology, vol. 32, 2002, pp. 1221-1235.
Horn et al., "Highly Sensitive, Fluorescent Transformation Marker for *Drosophila* Transgenesis", Development Genes and Evolution, vol. 210, 2000, pp. 623-629.
Horn,"PiggyBac-Based Insertional Mutagenesis and Enhancer Detection as a Tool for Functional Insect Genomics", Genetics, Vo. 163, 2003, pp. 647-661.
Huang et al., "Evolutionary conservation of apoptosis mechanisms: Lepidopteran and baculoviral inhibitor of apoptosis proteins are inhibitors of mammalian caspase-9", PNAS, vol. 97, No. 4, Feb. 15, 2000, pp. 1427-1432.

(56) References Cited

OTHER PUBLICATIONS

Imai et al., "Control of insecticide resistance in a filed population of houseflies, Musca domestica, by releasing susceptible flies", Researches on Population Ecology, vol. 29, 1987, pp. 129-146.

Inoue, "Binding of the *Drosophila* Sex-Lethal Gene Product to the Alternative Splice Site of Transformer Primary Transcript", Nature, vol. 344, 1990, pp. 461-463.

Irvin et al., "Assessing Fitness Costs for Transgenic Aedes Aegypti Expressing the GFP Marker and Transposase 3enes", Proceedings of the National Academy of Sciences of the United States of America, vol. 101, No. 3, January JO, 2004, pp. 891-896.

Jagiello et al., "NIPP-1, A Nuclear Inhibitory Subunit of Protein Phosphatase-1, Has RNA-Binding Properties", Journal of Biological Chemistry, vol. 272, No. 35, 1997, pp. 22067-22071.

Jattani et al., "Deficiency Screen Identifies a Novel Role for Beta 2 Tubulin in Salivary Gland and Myoblast Migration in the *Drosophila* Embryo", Developmental Dynamics, vol. 238, No. 4, Apr. 2009, pp. 853-863.

Jiang et al., "Tombola, a Tesmin/TS01-Family Protein, Regulates Transcriptional Activation in the *Drosophila* Male 3ermline and Physically Interacts with Always Early", Development, vol. 134, No. 8, 2007, pp. 1549-1559.

Jiang et al., "Transcriptional Activation in Drosophila Spermatogenesis Involves the Mutually Dependent Function of Aly and a Novel Meiotic Arrest Gene Cookie Monster", Development, vol. 130, No. 3, 2003, pp. 563-573.

Jin et al., "Engineered Female-Specific Lethality for Control of Pest Lepidoptera", ACS Synthetic Biology, American Chemical Society, USA, vol. 2 (3), Jan. 8, 2013, pp. 160-166.

Jin et al., "Mapping of The RNA-Binding and Endoribonuclease Domains of NIPP1, A Nuclear Targeting Subunit of Protein Phosphatase 1", Biochemical Journal, vol. 342, 1999, pp. 13-19.

Johnson-Schlitz et al., "P-Element-Induced Interallelic Gene Conversion of Insertions and Deletions in *Drosophila melanogaster*", Molecular and Cellular Biology, vol. 13, No. 11, 1993, pp. 7006-7018.

Kawase et al., "Gbb/Bmp Signaling Is Essential for Maintaining Germline Stem Cells and for Repressing Barn Transcription in the *Drosophila* Testis", Development, vol. 131, No. 6, 2004, pp. 1365-1375.

Kelly et al., "*Drosophila* MEF2 is a Direct Regulator of Actin57B Transcription in Cardiac, Skeletal, and Visceral Muscle Lineages", Mechanisms of Development, vol. 110, No. 1-2, 2002, pp. 39-50.

Kim et al., "Hybrid Restriction Enzymes: Zinc Finger Fusions to Fok I Cleavage Domain", Proceedings of the National Academy of Sciences of the United States of America, vol. 93, 1996, pp. 1156-1160.

Klassen et al., "Sterile Insect Technique, in: Sterile Insect Technique", Principles and Practice in Area-Wide Integrated Pest Management, The Netherlands, Springer, Curits et al., 2005, pp. 33-36.

Knipling et al., "Possibilities of Insect Control or Eradication Through the Use of Sexually Sterile Males", Journal of Economic Entomology, vol. 48, 1955, pp. 459-462.

Koukidou et al., "Germ Line Transformation of the Olive Fly Bactrocera Oleae Using a Versatile Transgenesis Marker", Insect Molecular Biology, vol. 15, No. 1, Feb. 2006 pp. 95-103.

Krafsur et al., "Bionomics of the Face Fly, Musca Autumnalis", Annual Review of Entomology, vol. 42, 1997, pp. 503-523.

Lankenau et al., "Comparison of Targeted-Gene Replacement Frequencies in *Drosophila melanogaster* at the Forked and White Loci", Molecular and Cellular Biology, vol. 16, No. 7, 1996, pp. 3535-3544.

Leftwich et al., (2014). "Genetic elimination of field-cage populations of Mediterranean fruit flies," Proc Biol Sci, 281(1792):20141372.

Leftwich, Philip T., "Male reproductive success and population control in the Mediterranean Fruit Fly, Ceratitis capitata", School of Biological Sciences, Aug. 2012, 226 pages.

Li et al., "piggyBac internal sequences are necessary for efficient transformation of target genomes", Insect Molecular Biology, vol. 14 (1), Jan. 2005, pp. 17-30.

Loew et al., "Improved Tel-Responsive Promoters with Minimized Background Expression", BMC Biotechnology, vol. 10, No. 81, 2010.

Louis et al., "A Theoretical Model for the Regulation of Sex-Lethal, a Gene that Controls Sex Determination and Dosage Compensation in *Drosophila melanogaster*", Genetics, vol. 165, Nov. 2003, pp. 1355-1384.

Loukeris et al., "Gene Transfer Into the Medfly, Ceratitis Capilala, with a *Drosophila* Hydei Transposable Element", Science, vol. 270, No. 5244, 1999, pp. 2002-2005.

Loukeris et al., "Introduction of the Transposable Element Minos into the Germ Line of *Drosophila melanogaster*", Proceedings of the National Academy of Sciences, vol. 92, 1995, pp. 9485-9489.

Lukyanov et al., "Natural Animal Coloration Can Be Determined by a Nonfluorescent Green Fluorescent Protein Homolog", The Journal of Biological Chemistry, vol. 275 (34), 2000, pp. 25879-25882.

Lycett et al., "Conditional Expression in the Malaria Mosquito Anopheles stephensi with Tel- On and Tel-Off Systems", Genetics, vol. 167, No. 4, Aug. 2004, pp. 1781-1790.

Mahfouz et al., "De nova-engineered transcription activator-like effector (TALE) hybrid nuclease with novel DNA binding specificity creates double-strand breaks", Proc Nall Acad Sci, vol. 101, No. 6, 2011, pp. 2623-2628.

Marrelli et al., "Mosquito Transgenesis: what is the fitness cost?", Trends Parasitol, Vo. 22, No. 5, 2006, pp. 197-202.

Mattox et al., "Alternative splicing of the sex determination gene transformer-2 is sex-specific in tile germ line but not in the soma", Genes & Development, vol. 4, No. 5, 1990, pp. 789-805.

Mattox et al., "Autoregulation of the splicing of transcripts from the transformer-2 gene of *Drosophila*", Genes & Development, vol. 5, 1991, pp. 786-796.

Matz et al., "Fluorescent Proteins from *Nonbioluminescent Anthozoa* Species", Nature Biotechnology, vol. 17, No. 10 1999, pp. 969-973.

May et al., "Tropical Arthropod Species, More or Less?", Science, vol. 329, 2010, pp. 41-42.

Maynard-Smith et al., "A Directed Approach for Engineering Conditional Protein Stability Using Biologically Silent Small Molecules", Journal of Biological Chemistry, vol. 282, No. 34, 2007, pp. 24866-24872.

McInnis et al., "Mating and Remating of Medflies (Diptera: Tephritidae) in Guatemala: Individual Fly Marking in Field Cages", Florida Entomologist, vol. 85(1), Mar. 2002, pp. 126-137.

Michiels et al., "A 14 Bp Promoter Element Directs the Testis Specificity of the Drosophila B2 Tubulin Gene", The EMBO Journal vol. 8, No. 5, 1989, pp. 1559-1565.

Miller et al., "A TALE Nuclease Architecture for Efficient Genome Editing", Nature Biotechnology, vol. 29, No. 2, J011, pp. 143-148.

Miller et al., "An Improved Zinc-finger Nuclease Architecture for Highly Specific Genome Editing", Nature Biotechnology, vol. 25, No. 7, 2007, pp. 778-785.

Mishra et al., "Understanding Forest Biology", Discovery publishing house, 2009, 3 pages.

Morrison et al., "Engineered repressible lethality for controlling the pink bollworm, a lepidopteran pest of cotton", PLOS One, vol. 7, No. 12:e50922, 2012.

Morrison et al., "Genetic Improvements to The Sterile Insect Technique for Agricultural Pests", Asia-Pacific Journal of Molecular Biology and Biotechnology, vol. 18, No. 2, 2010, pp. 275-295.

Mounier et al., "Insect Muscle Actins Differ Distinctly from Invertebrate and Vertebrate Cytoplasmic Actins", Journal of Molecular Evolution, vol. 34, No. 5, 1992, pp. 406-415.

Mumford, John D., "Science, Regulation, and Precedent for Genetically Modified Insects", PLOS, vol. 6, Issue 1, Jan. 2012, 4 pages.

Munoz et al., "The AeAct-4 Gene is Expressed in the Developing Flight Muscles of Female Aedes Aegypti", Insect Molecular Biology, vol. 13, No. 5, Oct. 2004, pp. 563-568.

Nagaraju et al., "Lepidopteran Sex Determination: A Cascade of Surprises", Sexual Development, vol. 8, Available online at: <htlps://doi.org/10.1159/000357483>, 2014, pp. 104-112.

Namciu et al., "Human Matrix Attachment Regions Insulate Transgene Expression from Chromosomal Position Effects in *Drosophila melanogaster*", Molecular and Cellular Biology, vol. 18, No. 4, 1998, pp. 2382-2391.

(56) References Cited

OTHER PUBLICATIONS

Nene et al., Genome sequence of Aedes aegypti, a major arbovirus vectM, Science, vol. 316, No. 5832, 2007, pp. 1718-1723.
Nielsen et al., "Axoneme-specific Beta-tubulin Specialization: A Conserved C-terminal Motif Specifies The Central Pair", Current Biology, vol. 11, No. 7, 2001, pp. 529-533.
Nitasaka et al., "Repressor of P Elements in *Drosophila melanogaster*: Cytotype Determination by a Defective P Element Carrying Only Open Reading Frames O Through 2", Proceedings of the National Academy of Sciences of the United States of America, vol. 84, No. 21, 1987, pp. 7605-7608.
Nongthomba et al., "Expression and Function of the *Drosophila* Act88F Actin Isoform is not Restricted to the Indirect Flight Muscles", Journal of Muscle Research and Cell Motility, vol. 22, No. 2, 2001, 1 Page.
O'Brochta et al., "Gene Vector and Transposable Element Behavior in Mosquitos", The Journal of Experimental Biology, vol. 206, 2003, pp. 3823-3834.
Ohshima et al., "Reassessment of 79B actin gene expression in the abdomen of adult *Drosophila melanogaster*", Insect Molecular Biology, vol. 6, No. 3, 1997, 2 pages.
Olsen, "Fibroblast Growth Factor {FGF) Homologous Factors Share Structural but Not Functional Homology with rGFs", J Biol. Chem. vol. 278, 2003, pp. 34226-34236.
Olson et al., "A GH3-like Domain in Reaper Is Required for Mitochondrial Localization and Induction of IAP Degradation", The Journal of Biological Chemistry, vol. 278, No. 45, 2003, pp. 44758-44768.
Osanai-Futahasi et al., "A Visible Dominant Marker for Insect Transgenesis", Nature Communications, vol. 3, No. 1295, 2012.
Osterwalder et al., "A Conditional Tissue-specific Transgene Expression System using Inducible GAL4", Proceedings of the National Academy of Sciences of the United States of America, vol. 98, No. 22, 2001, pp. 12596-12601.
Oxitec, Newsletter, http://www.oxitec.com/our-news/newsletters/november—J011—newsletter/, downloaded, Dec. 13, 2011, 6 pages.
Pane et al., (2002). "The transformer gene in Ceratitis capitata provides a genetic basis for selecting and remembering the sexual fate," Development, 129:3715-3725.
Papathanos et al., "Sex separation strategies: past experience and new approaches," Malar J. (2009) 8 Supp 2:S5.
Parker et al., "Functional Interaction between Nuclear Inhibitor of Protein Phosphatase Type 1 {NIPP1) and Protein Phosphatase Type 1 {PP1) in *Drosophila*: Consequences of Overexpression Of NIPP1 in Flies and Suppression by co-expression of PP1", Biochemical Journal, vol. 368, 2002, pp. 789-797.
Parker, "Mass-rearing for sterile insect release," The Netherlands, Springer (2005) pp. 209-232.
Peloquin et al., "Germ-line Transformation of Pink Bollworm (Lepidoptera: Gelechiidae) Mediated by The Piggybac Transposable Element", Insect Molecular Biology, vol. 9, No. 3, 2000, pp. 323-333.
Perera et al., "Germ-line Transformation of the South American Malaria Vector, Anopheles albimanus, with a Piggybac/Egfp Transposon Vector, is Routine and Highly Efficient", Insect Molecular Biology, vol. 11, No. 4, 2002, pp. 91-297.
Perezgasga et al., "Regulation of transcription of meiotic cell cycle and terminal differentiation genes by the testis-specific Zn-finger protein matotopetli," Development (2004) 131 (8):1691-1702.
Perrin et al., "The Actin Gene Family: Function follows Isoform", Cy1oskeleton, vol. 67, No. 10, 2010, pp. 630-634.
Phuc et al., "Late-acting dominant lethal genetic systems and mosquito control," BMC Biol (2007) 5:11.
PiggyBac Website, http://piggybac.bio.nd.edu/, Mar. 21, 2006.
Pinkerton et al., "Green Fluorescent Protein as a Genetic Marker in Transgenic Aedes Aegypti", Insect Molecular Biology, vol. 9, No. 1, 2000, pp. 1-10.
Prasher et al., "Primary structure of the Aequorea victoria green-fluorescent protein," Gene (1992) 111 (2):229-233.
Qin et al., "Systematic Comparison of Constitutive Promoters and the Doxycycline-inducible Promoter", PLOS One, vol. 5, No. 5, 2010.
Raja et al., "Replacement by *Drosophila melanogaster* Protamines and Mst77F of Histones during Chromatin condensation in Late Spermatids and Role of Sesame in the Removal of These Proteins from the Male Pronucleus", Molecular and Cellular Biology, vol. 25, No. 14, 2005, pp. 6165-6177.
Remy et al., "Zinc-finger Nucleases: A Powerful Tool for Genetic Engineering of Animals", Transgenic Research, vol. 19, 2010, pp. 363-371.
Rendon et al., "Medfly (Diptera: Tephritidae) Genetic Sexing: Large-scale Field Comparison of Males-only and Bisexual Sterile Fly Releases in Guatemala", Journal of Economic Entomology, vol. 97, No. 5, 2004, pp. 1547-1553.
Robinson et al., "Ceratitis Capitata-a Suitable Case for Genetic Sexing", Genetica, vol. 58, No. 3, 1982, pp. 229-237.
Robinson et al., "Genetic Basis of the Sterile Insect Technique", in: Sterile Insect Technique, Principles and Practice in Area-Wide Integrated Pest Management, 2005, pp. 95-114.
Robinson et al., "Prospects for The Future Development and Application of the Sterile Insect Technique", The Netherlands, Springer, 2005, pp. 727-760.
Robinson et al., "Recent Findings on Medfly Sexual Behaviour: Implications for SIT", Florida Entomologist, 85(1), Mar. 2002, pp. 171-181.
Robinson et al., "Mutations and Their Use in Insect Control", Mutation Research, vol. 511, 2002, pp. 113-132.
Ronaldson et al., "Two independent cis-acting elements regulate the sex- and tissue specific expression of yp3 in *Drosophila melanogaster*", Genet Res., vol. 6, No. 1, 1995, pp. 9-17.
Rong et al., "A Targeted Gene Knockout in *Drosophila*", Genetics, vol. 157, No. 3, 2001, pp. 1307-1312.
Rong et al., "Gene Targeting by Homologous Recombination in *Drosophila*", Science, vol. 288, No. 5473, 2000, pp. 2013-2018.
Rong et al., "Targeted Mutagenesis by Homologous Recombination in *D. melanogaster*", Genes & Development, vol. 16, 2002, pp. 1568-1581.
Roper et al., "Contribution of Sequence Variation in *Drosophila* Actins to their Incorporation Into Actin-based Structures in Vivo", Journal of Cell Science, vol. 118, 2005, pp. 3937-3948.
Rossler et al., "The Genetics of the Mediterranean Fruit Fly: A "White Pupae" Mutant", Annals of the Entomological Society of America, vol. 72, 1979, pp. 583-585.
Rubin et al., "Genetic Transformation of *Drosophila* with Transposable Element Vectors", Science, vol. 218, No. 1570, 1982, pp. 348-353.
Russ et al., "Self-Deleting Retrovirus Vectors for Gene Therapy", Journal of Virology, vol. 70, No. 8, 1996, pp. 4927-4932.
Saccone et al., "Sex Determination in Flies, Fruit Flies and Butterflies", Genetica, vol. 116, 2002, pp. 15-23.
Saccone et al., "Sex Determination in Medfly: A Molecular Approach", Area-Wide Control of Fruit Flies and other Insect Pests I IAEA, 2000, pp. 491-496.
Salvemini et al., "Genomic organization and splicing evolution of the double sex gene, a *Drosophila* regulator of sexual differentiation, in the dengue and yellow fever mosquito Aedes aegypti", BMC Evolutionary Biology, vol. 11, No. 1:41, 2011.
Santel et al., The *Drosophila* Don Juan (Di) Gene Encodes a Novel Sperm Specific Protein Component Characterized by an Unusual Domain of a Repetitive Amino Acid Motif, Mechanisms of Development, vol. 64, No. 1-2, 1997, pp. 19-30.
Scali et al., "Identification of Sex-specific Transcripts of the Anopheles Gambiae Doublesex Qene", Journal of Experimental Biology, vol. 208, No. 19, Oct. 2005, pp. 3701-3709.
Schetelig et al., "Strategy for Enhanced Transgenic Strain Development for Embryonic Conditional Lethality in Anastrepha Suspensa", Proceedings of the National Academy of Sciences of the United States of America, vol. 24, J012, pp. 9348-9353.
Schwechheimer et al., "Transactivation of a Target Gene Through Feedforward Loop Activation in Plants", Functional & Integrative Genomics, vol. 1, 2000, pp. 35-43.

(56) References Cited

OTHER PUBLICATIONS

Scolari et al., "A transgenic sperm marking system in the medfly, as a tool for pest control strategies and sperm use analysis", Entomological Research, vol. 37, 2007, pp. A56.
Sepp et al., "Conversion of Lacz Enhancer Trap Lines to Gal4 Lines using Targeted Transposition in *Drosophila melanogaster*", Genetics, vol. 151, 1999, pp. 1093-1101.
Shah et al., "Cardiac remodeling in Drosophila arises from changes in actin gene expression and from a contribution of lymph gland-like cells to the heart musculature", Mechanisms of Development, vol. 128, No. 3, 2011, pp. 222-233.
Shelton et al., "Field Tests on Managing Resistance to BI-engineered Plants", Nature Biotechnology, vol. 18, 2000, pp. 339-342.
Shockett et al., "A Modified Tetracycline-Regulated System Provides Autoregulatory, Inducible Gene Expression in Cultured Cells and Transgenic Mice", Proceedings of the National Academy of Sciences of the United States of America, vol. 92, Jul. 1995, pp. 6522-6526.
Shukla et al., "Two female-specific DSX proteins are encoded by the sex-specific transcripts of dsx, and are required or female sexual differentiation in two wild silkmoth species, Antheraea assama and Antheraea mylitta {Lepidoptera, Saturniidae)", Insect Biochemistry and Molecular Biology, vol. 40 (9), Sep. 2010, pp. 672-682.
Simmons et al., "Field Performance of a Genetically Engineered Strain of Pink Bollworm", Plos ONE, vol. 6 (9), 24110, Sep. 2011, 11 pages.
Smith et al., "Testis-specific Expression of The Beta2 Tubulin Promoter of Aedes Aegypti and It's Armlication as a Aenetic Sex-separation Marker", Insect Molecular Biology, vol. 16, No. 1, 2007, pp. 16-71.
Sondergaard et al., "Nutritional Response in a Drosophila Yolk Protein Gene Promoter", Molecular Genetics and 3enomics, vol. 248, No. 1, 1995, pp. 25-32.
Spradling et al., "P Element-mediated Transformation", *Drosophila*: A Practical Approach, Chapter 8, 1986, pp. 175-197.
Spradling et al., "Transposition of Cloned p. Elements Into *Drosophila* Germ Line Chromosomes", Science, vol. J18, No. 4570, 1982, pp. 341-347.
Stadtfeld et al., Without A Trace? Piggybac-ing Toward Pluripotency, Nature Methods, vol. 6, No. 5, 2009, pp. 329-330.
Stebbins et al., "Adaptable Doxycycline-Regulated Gene Expression Systems for *Drosophila*", Gene, vol. 270, 2001, pp. 103-111.
Stebbins et al., "Tetracycline-Inducible Systems for *Drosophila*", Proceedings of the National Academy of Sciences of the United States of America, vol. 98, 2001, pp. 10775-10780.
Steiner et al., "Homologous Recombination as the Main Mechanism for DNA Integration and Cause of Rearrangements in the Filamentous Ascomycete Ashbya Gossypii", Genetics, vol. 140, 1995, pp. 973-987.
Suzuki et al., "Role of the male BmDSX protein in the sexual differentiation of Bombyx mori", Evolution & Development, vol. 7 (1), 2005, pp. 58-68.
Tan et al., "Transgene-based, female-specific lethality system for genetic sexing of the silkworm, Bombyx mori", PNAS, vol. 110 (17) Available online at: <hllps://doi.org/10.1073/pnas.1221700110>, Apr. 23, 2013, pp. 6766-6770.
Theodoraki et al., "cDna Cloning, Heat Shock Regulation and Developmental Expression of the Hsp83 Gene in the Mediterranean Fruit Fly Ceratitis Capitata", Insect Molecular Biology, vol. 15, No. 6, 2006, pp. 839-852.
Thibault et al., "Precise excision and transposition of piggyBac in pink bollworm embryos", Insect Molecular Biology, vol. 8 (1), Feb. 1999, pp. 119-123.
Thomas et al., "Insect Population Control using a Dominant, Repressible, Lethal Genetic System", Science, vol. 287, No. 5462,2000, pp. 2474-2476.
Timoshevskiy et al., "An integrated linkage, chromosome, and Genome map for the Yellow Fever Mosquito Aedes egypti", PLOS Neglected Tropical Diseases, vol. 7, No. 2:e2052, 2013.
Timoshevskiy et al., "Genomic composition and evolution of Aedes aegypti chromosomes revealed by the analysis Jf physically mapped supercontigs", BMC Biology vol. 12, No. 1:27, 2014.
Toshiki et al., "Germline Transformation of The Silkworm *Bombyx mori* L. using a Piggybac Transposon-derived Vector", Nature Biotechnology, vol. 18, No. 1, 2000, pp. 81-84.
Urnov et al., "Highly Efficient Endogenous Human Gene Correction using Designed Zinc—finger Nucleases", Nature, vol. 435, 2005, pp. 646-651.
Van Eynde et al., "Molecular cloning of NIPP-1, a nuclear inhibitor of protein phosphatase-1, reveals homology with polypeptides involved in RNA processing," J Biol Chem (1995) 270(47}:28068-28074.
Van Eynde et al., "Organization and alternate splice products of the gene encoding nuclear inhibitor of protein phosphatase-1 (IPP-1)," Eur J Biochem (1999) 261(1):291-300.
Vernooy et al., "Cell Death Regulation in *Drosophila*: Conservation of Mechanism and Unique Insights", The Journal Jf Cell Biology, vol. 150, No. 2, Jul. 2000, pp. F69-F75.
Viktorinova et al., "Comparative Analysis of Binary Expression Systems for Directed Gene Expression in Transqenic Insects", Insect Biochemistry and Molecular Biology, vol. 37, 2007, pp. 246-254.
Vivinus et al., "An element within the 5' untranslated region of human Hsp70 mRNA which acts as a general enhancer of mRNA translation," European Journal of Biochemistry, vol. 268, 2001, pp. 1908-1917.
Vreysen et al., "Engineering Insects for the Sterile Insect Technique", Dordrechl, The Netherlands, Springer, 2007, pp. 51-60.
Vulsteke et al., "Properties And Phosphorylation Sites Of Baculovirus-expressed Nuclear Inhibitor Of Protein Dhosphatase-1 (Nipp-1 }", Journal of Biological Chemistry, vol. 272, No. 52, 1997, pp. 32972-32978.
Wang et al., "Conserved RNA cis-elements regulate alternative splicing of Lepidopteran doublesex," Insect Biochemistry and Molecular Biology, vol. 44, Jan. 2014, 11 pages.
Webster et al.,(1988). "The yeast UASG is a transcriptional enhancer in human hela cells in the presence of the GAL4 trans-activator," Cell, 52:169-178.
Weinmann et al., "A Chimeric Transactivator Allows Tetracycline-responsive Gene Expression In Whole Plants", The Diani Journal, vol. 5, No. 4, 1994, pp. 559-569.
Wera et al., "Inhibition Of Translation By Mrna Encoding Nipp-1, A Nuclear Inhibitor Of Protein Phosphatase-1", European Journal of Biochemistry, vol. 247, No. 1, 1997, pp. 411-415.
Wharton et al., "CNS Midline Enhancers Of The *Drosophila* Slit And Toll Genes", Mechanisms of Development, vol. 10, No. 3, 1993, pp. 141-154.
White et al., "Cell Killing by the Drosophila Gene reaper", Science, vol. 271, Feb. 9, 1996, pp. 805-807.
White-Cooper et al., "Transcription Of Meiotic Cell Cycle And Terminal Differentiation Genes Depends On A conserved Chromatin Associated Protein, Whose Nuclear Localisation Is Regulated", Development, vol. 127, 2000, p. 5463-5473.
Wilson et al., "Hepatocyte-direcled Gene Transfer in Vivo Leads to Transient Improvement of Hypercholesterolemia in Low Density Lipoprotein Receptor-deficient Rabbits," J Biol Chem, vol. 267, 1992, pp. 963-967.
Wilson et al., "Position Effects On Eukaryotic Gene Expression", Annual Review of Cell and Developmental Biology, vol. 6, 1990, pp. 679-714.
Wilson et al., "Sperm Plasma Membrane Breakdown During Drosophila Fertilization Requires Sneakv, An Acrosoma Membrane Protein", Development, vol. 133, No. 24, 2006, pp. 4871-4879.
Wimmer et al., "Eco-friendly Insect Management", Nature Biotechnology, vol. 23, No. 4, 2005, pp. 432-433.
Windbichler et al., "A Synthetic Homing Endonuclease-based Gene Drive System In The Human Malaria Mosquito", Nature, vol. 473, No. 7346, 2011, pp. 212-215.
Windbichler et al., "Homing Endonuclease Mediated Gene Targeting in Anopheles Gambiae Cells and Embryos", Nucleic Acids Research, vol. 35, 2007, pp. 5922-5933.

(56) References Cited

OTHER PUBLICATIONS

Windbichler et al., "Targeting The X Chromosome During Spermatogenesis Induces Y Chromosome Transmission Ratio Distortion And Early Dominant Embryo Lethality In Anopheles Qambiae", PLOS Genetics, vol. 4, No. 12, 2008.
Wing et al., "Distinct Cell Killing Properties of the *Drosophila reaper*, Head Involution Defective, and Grim Genes", Cell Death and Differentiation, 1998, pp. 930-939.
Wing et al., "The RHG motifs of Drosophila Reaper and Grim are important for their distinct cell death-inducing abilities", Mechanisms of Development, vol. 102, 2001, pp. 193-203.
Wise De Valdez et al., "Genetic elimination of dengue vector mosquitoes," Proc Natl Acad Sci USA (2011} 108(12):4772-4775.
Wobus et al., "A New Transposable Element in Chironomus thummi", Molecular Genetics and Genomics, vol. 222, 1990, pp. 311-316.
Woltjen et al., "Piggybac Transposition Reprograms Fibroblasts to Induced Pluripotent Stem Cells", Nature, vol. 158, No. 7239, 2009, 766-770.
Wool et al., "Genetically-Induced Susceptibility to Malathion in Tribolium Castaneum Despite Selection for Resistance", Entomologia Experimentalis et Applicata, 1980, pp. 183-190.
Wu et al., "Expression of Highly Controllable Genes in Insect Cells using a Modified Tetracycline-regulated Gene Expression System", Journal of Biotechnology, vol. 80, Issue 1, Jun. 2000, pp. 75-83.
Wu et al., "Receptor-mediated Gene Delivery and Expression in Vivo," J Biological Chemistry, vol. 263, 1988, pp. 14621-14624.
Xu et al., "Sexually dimorphic traits in the silkworm, Bombyx mori, are regulated by doublesex", Insect Biochemistry and Molecular Biology vol. 80, Jan. 2017, pp. 42-51.
Zhao et al., "Male Germ Cell Specification and Differentiation", Developmental Cell, vol. 2, No. 5, May 2002, pp. 37-547.
Zimowska et al., "The Beta2-tubulin Gene from three Tephritid Fruit Fly Species and Use of Its Promoter for Sperm Marking", Insect Biochemistry and Molecular Biology, vol. 39, No. 8, 2009, pp. 508-515.
Advisory Action for U.S. Appl. No. 11/733,737, dated Jun. 3, 2013, 7 pages.
Advisory Action for U.S. Appl. No. 11/733,737, dated Aug. 5, 2009, 4 pages.
Amendment for U.S. Appl. No. 10/562,843, filed Feb. 24, 2009, 13 pages.
Amendment for U.S. Appl. No. 10/562,843, filed Nov. 30, 2010, 7 pages.
Amendment for U.S. Appl. No. 10/562,843, filed Oct. 5, 2009, 10 pages.
Amendment for U.S. Appl. No. 10/566,448, filed Oct. 27, 2010, 20 pages.
Amendment for U.S. Appl. No. 10/566,448, filed Jul. 7, 2009, 15 pages.
Amendment for U.S. Appl. No. 11/352,177, filed Dec. 10, 2009, 20 pages.
Amendment for U.S. Appl. No. 11/352,177, filed Oct. 14, 2010, 13 pages.
Appeal Brief for U.S. Appl. No. 11/733,737, filed Feb. 3, 2014, 40 pages.
Appeal Brief for U.S. Appl. No. 12/278,849, filed Oct. 16, 2014, 31 pages.
Communication pursuant to Article 94(3) EPC for EP 07712717.3, dated Jul. 11, 2014, 8 pages.
Communication pursuant to Article 94(3) EPC for EP 07712717.3, dated Nov. 6, 2015, 4 pages.
Communication pursuant to Article 96(2) EPC for EP 00979774.7, dated Aug. 2, 2005, 4 pages.
Communication pursuant to Article 96(2) EPC for EP 00979774.7, dated Nov. 28, 2003, 5 pages.
Communication pursuant to Article 96(2) EPC for EP 00979774.7, dated Oct. 4, 2004, 4 pages.
Communication pursuant to Article 96(2) EPC for EP 00979774.7, dated Mar. 8, 2006, 4 pages.
Communication under Rule 51 (4) EPC, directed to EP 00979774.7, dated May 9, 2007, 4 pages.
Communication under Rule 71 (3) EPC for EP 07712717.3, dated Jun. 20, 2016, 7 pages.
Decision on Further Processing for EP 00979774.7, dated Jan. 29, 2007, 1 page.
EP First Office Action, dated Feb. 16, 2012, in European Patent Application No. 04743590.4, a corresponding application, 8 pages.
Examination Report for EP 04743590.4, dated Nov. 14, 2008, 4 pages.
Examination Report for NZ 519175, dated Nov. 28, 2003, 1 page.
Examination Report for NZ 519175, dated Jul. 9, 2002, 2 pages.
Examiner's Answer to Appeal Brief for U.S. Appl. No. 11/733,737, dated Jul. 18, 2014, 12 pages.
Final Office Action for U.S. Appl. No. 10/148,041, dated Mar. 7, 2006, 9 pages.
Final Office Action for U.S. Appl. No. 10/562,843, filed Aug. 25, 2011, 5 pages.
Final Office Action for U.S. Appl. No. 10/562,843, dated Feb. 3, 2010, 5 pages.
Final Office Action for U.S. Appl. No. 10/566,448, dated Nov. 10, 2009, 18 pages.
Final Office Action for U.S. Appl. No. 10/566,448, dated Aug. 14, 2014, 24 pages.
Final Office Action for U.S. Appl. No. 10/566,448, dated Feb. 2, 2011, 13 pages.
Final Office Action for U.S. Appl. No. 11/352,177, dated Oct. 14, 2014, 6 pages.
Final Office Action for U.S. Appl. No. 11/352,177, dated Mar. 16, 2011, 18 pages.
Final Office Action for U.S. Appl. No. 11/733,737, dated Apr. 17, 2009, 16 pages.
Final Office Action for U.S. Appl. No. 11/733,737, dated Aug. 4, 2010, 18 pages.
Final Office Action for U.S. Appl. No. 11/733,737, dated Jan. 7, 2013, 26 pages.
Final Office Action for U.S. Appl. No. 12/278,849, dated Jun. 6, 2013, 24 pages.
Final Office Action for U.S. Appl. No. 12/278,849, dated Mar. 17, 2014, 24 pages.
Final Office Action for U.S. Appl. No. 12/278,849, dated Oct. 9, 2015, 7 pages.
Final Office Action for U.S. Appl. No. 13/942,601, dated Jul. 31, 2014, 23 pages.
Formal Report (translation) for BR PI0707579-0, dated Jun. 21, 2016, 2 pages.
Formal Report (translation} for BR PI0413024-3, dated Jun. 7, 2016, 10 pages.
Further International Search Report GB 9928181.8; dated Apr. 30, 2001, 2 pages.
International Preliminary Examination Report for PCT/GB00/04541, dated Apr. 4, 2002, 2 pages.
International Preliminary Report on Patentability for PCT/EP2014/054290, dated Sep. 8, 2015, 7 pages.
International Preliminary Report on Patentability for PCT/GB2004/002021, dated Nov. 18, 2005, 6 pages.
International Preliminary Report on Patentability for PCT/GB2004/002869, dated Jan. 3, 2006, 9 pages.
International Preliminary Report on Patentability for PCT/GB2004/003263, dated Jan. 30, 2006, 6 pages.
International Preliminary Report on Patentability for PCT/GB2007/000488, dale of search May 5, 2008, 11 pages.
International Search Report and Written Opinion for PCT/EP2013/054417, dated Jul. 12, 2013, 14 pages.
International Search Report and Written Opinion for PCT/EP2014/054290, dated Jun. 18, 2014, 11 pages.
International Search Report and Written Opinion received for PCT Patent Application No. PCT/GB2015/051633, dated Oct. 16, 2015, 11 pages.
International Search Report and Written Opinion received for PCT Patent Application No. PCT/GB2019/050897, dated Jun. 18, 2019, 10 pages.

(56) References Cited

OTHER PUBLICATIONS

International Search Report and Written Opinion received for PCT Patent Application No. PCT/IB2017/001128, dated Dec. 13, 2017, 17 pages.
International Search Report for PCT/GB2000/04541, dated Nov. 19, 2001.
International Search Report for PCT/GB2004/002021, dated Oct. 6, 2004, 3 pages.
International Search Report for PCT/GB2004/002869, dated Jan. 11, 2005, 5 pages.
International Search Report for PCT/GB2004/003263, dated Nov. 5, 2004, 3 pages.
International Search Report for PCT/GB2007/000488, dated Jun. 6, 2007, 3 pages.
Notice of Allowance for U.S. Appl. No. 10/566,448, dated Jul. 13, 2015, 10 pages.
Notice of Allowance for U.S. Appl. No. 10/566,448, dated Mar. 19, 2015, 10 pages.
Notice of Allowance for U.S. Appl. No. 11/352,177, dated Mar. 17, 2015, 10 pages.
Notice of Allowance for U.S. Appl. No. 11/352,177, dated Jul. 7, 2015, 9 pages.
Notice of Allowance for U.S. Appl. No. 13/942,601, dated Apr. 10, 2015, 11 pages.
Notice of Allowance for U.S. Appl. No. 13/942,601, dated Jul. 7, 2015, 9 pages.
Notice of Appeal for U.S. Appl. No. 10/566,448, filed Feb. 18, 2015, 4 pages.
Notice of Appeal for U.S. Appl. No. 11/733,737, filed Jul. 3, 2013, 1 page.
Notice of Appeal for U.S. Appl. No. 12/278,849, filed Jun. 17, 2014, 1 page.
Notice of Appeal for U.S. Appl. No. 13/942,601, filed Feb. 2, 2015, 1 page.
Noting of loss of rights (R. 69(1) EPC) for EP 00979774.7, dated Jul. 17, 2004, 1 page.
Office Action for AU 17165/01, dated Jul. 13, 2004, 3 pages.
Office Action for CN 00818682.0, fax dated Feb. 4, 2005, 7 pages.
Office Action for IL 149885, dated Apr. 26, 2007, 4 pages.
Office Action for U.S. Appl. No. 10/148,041, dated Jul. 1, 2005, 14 pages.
Office Action for U.S. Appl. No. 10/148,041, dated Oct. 10, 2006, 8 pages.
Office Action for U.S. Appl. No. 10/556,804, dated Feb. 1, 2011, 4 pages.
Office Action for U.S. Appl. No. 10/556,804, dated May 12, 2010, 8 pages.
Office Action for U.S. Appl. No. 10/562,843, dated Nov. 12, 2008, 6 pages.
Office Action for U.S. Appl. No. 10/562,843, dated Feb. 16, 2011, 4 pages.
Office Action for U.S. Appl. No. 10/562,843, dated Jul. 30, 2010, 7 pages.
Office Action for U.S. Appl. No. 10/562,843, dated Jun. 9, 2009, 5 pages.
Office Action for U.S. Appl. No. 10/566,448, dated Nov. 22, 2013, 24 pages.
Office Action for U.S. Appl. No. 10/566,448, dated Apr. 27, 2010, 12 pages.
Office Action for U.S. Appl. No. 10/566,448, dated Jan. 7, 2009, 14 pages.
Office Action for U.S. Appl. No. 11/352,177, dated Jan. 30, 2014, 17 pages.
Office Action for U.S. Appl. No. 11/352,177, dated Jun. 10, 2009, 14 pages.
Office Action for U.S. Appl. No. 11/352,177, dated Apr. 14, 2010, 15 pages.
Office Action for U.S. Appl. No. 11/733,737, dated Oct. 1, 2009, 21 pages.
Office Action for U.S. Appl. No. 11/733,737, dated Apr. 10, 2008, 8 pages.
Office Action for U.S. Appl. No. 11/733,737, dated Mar. 27, 2012, 17 pages.
Office Action for U.S. Appl. No. 11/733,737, dated Jun. 28, 2011, 14 pages.
Office Action for U.S. Appl. No. 11/733,737, dated Feb. 8, 2011, 6 pages.
Office Action for U.S. Appl. No. 12/278,849, dated Aug. 9, 2013, 22 pages.
Office Action for U.S. Appl. No. 12/278,849, dated Oct. 10, 2012, 12 pages.
Office Action for U.S. Appl. No. 12/278,849, dated Mar. 10, 2015, 18 pages.
Office Action for U.S. Appl. No. 12/278,849, dated Dec. 5, 2014, 15 pages.
Office Action for U.S. Appl. No. 13/942,601, dated Nov. 4, 2013, 17 pages.
Prosecution history for related application U.S. Appl. No. 10/148,041, 64 pages.
Prosecution history for related application U.S. Appl. No. 10/556,804, 27 pages.
Prosecution history for related application U.S. Appl. No. 10/562,843, 63 pages.
Prosecution history for related application U.S. Appl. No. 10/566,448, 142 pages.
Prosecution history for related application U.S. Appl. No. 11/352,177, 129 pages.
Prosecution history for related application U.S. Appl. No. 11/733,737, 175 pages.
Prosecution history for related application U.S. Appl. No. 12/278,849, 20 pages.
Rejection for CN 00818682.0, fax dated Jan. 26, 2006, 4 pages.
Reply Brief and Request for Oral Hearing for U.S. Appl. No. 11/733,737, filed Sep. 18, 2014, 16 pages.
Request for Continued Examination for U.S. Appl. No. 10/148,041, filed Sep. 11, 2006, 8 pages.
Request for Continued Examination for U.S. Appl. No. 10/566,448, filed Jun. 18, 2015, 3 pages.
Request for Continued Examination for U.S. Appl. No. 10/566,448, filed Aug. 2, 2011, 23 pages.
Request for Continued Examination for U.S. Appl. No. 10/566,448, filed Feb. 25, 2010, 18 pages.
Request for Continued Examination for U.S. Appl. No. 11/352,177, filed Sep. 16, 2011, 3 pages.
Request for Continued Examination for U.S. Appl. No. 11/352,177, filed Jun. 17, 2015, 3 pages.
Request for Continued Examination for U.S. Appl. No. 11/733,737, filed Aug. 14, 2009, 1 page.
Request for Continued Examination for U.S. Appl. No. 13/942,601, filed Jun. 19, 2015, 3 pages.
Request for Further Processing for EP 00979774.7, filed Jan. 4, 2007, 4 pages.
Response for U.S. Appl. No. 10/562,843, filed Feb. 24, 2009, 13 pages.
Response for U.S. Appl. No. 10/562,843, filed Nov. 30, 2010, 8 pages.
Response for U.S. Appl. No. 10/562,843, filed Oct. 5, 2009, 10 pages.
Response for U.S. Appl. No. 11/352,177, filed Dec. 10, 2009, 20 pages.
Response for U.S. Appl. No. 11/352,177, filed Oct. 14, 2010, 13 pages.
Response to Communication for EP 00979774.7, filed Apr. 14, 2005, 7 pages.
Response to Communication for EP 00979774.7, filed Sep. 20, 2004, 8 pages.
Response to Communication pursuant to Article 94(3) EPC, for EP 07712717.3 filed Mar. 16, 2016, 5 pages.
Response to Communication pursuant to Article 96(2) EPC for EP 00979774.7, filed Feb. 13, 2006, 8 pages.
Response to Final Office Action for U.S. Appl. No. 10/562,843, filed Nov. 21, 2011, 6 pages.

(56) References Cited

OTHER PUBLICATIONS

Response to Final Office Action for U.S. Appl. No. 10/566,448, filed Dec. 15, 2014, 9 pages.
Response to Final Office Action for U.S. Appl. No. 11/352,177, filed Sep. 16, 2011, 15 pages.
Response to Final Office Action for U.S. Appl. No. 11/352,177, filed Dec. 3, 2014, 8 pages.
Response to Final Office Action for U.S. Appl. No. 11/733,737, filed Jul. 17, 2009, 26 pages.
Response to Final Office Action for U.S. Appl. No. 11/733,737, filed Dec. 6, 2010, 26 pages.
Response to Final Office Action for U.S. Appl. No. 11/733,737, filed Apr. 8, 2013, 25 pages.
Response to Office Action for U.S. Appl. No. 10/148,041, filed Dec. 5, 2005, 11 pages.
Response to Office Action for U.S. Appl. No. 10/556,804, filed Nov. 12, 2010, 12 pages.
Response to Office Action for U.S. Appl. No. 10/556,804, filed Mar. 25, 2011, 9 pages.
Response to Office Action for U.S. Appl. No. 10/562,843, filed Jun. 16, 2011, 9 pages.
Response to Office Action for U.S. Appl. No. 10/566,448, filed Apr. 22, 2014, 17 pages.
Response to Office Action for U.S. Appl. No. 10/566,448, filed Oct. 27, 2010, 20 pages.
Response to Office Action for U.S. Appl. No. 10/566,448, filed Aug. 28, 2009, 15 pages.
Response to Office Action for U.S. Appl. No. 10/566,448, filed Jul. 7, 2009, 15 pages.
Response to Office Action for U.S. Appl. No. 11/352,177, dated May 28, 2014, 14 pages.
Response to Office Action for U.S. Appl. No. 11/733,737, filed Oct. 10, 2008, 8 pages.
Response to Office Action for U.S. Appl. No. 11/733,737, filed Feb. 18, 2011, 11 pages.
Response to Office Action for U.S. Appl. No. 11/733,737, filed Oct. 28, 2011, 27 pages.
Response to Office Action for U.S. Appl. No. 11/733,737, filed Jan. 29, 2010, 23 pages.
Response to Office Action for U.S. Appl. No. 11/733,737, filed Aug. 9, 2012, 24 pages.
Response to Office Action for U.S. Appl. No. 12/278,849, dated Apr. 10, 2013, 19 pages.
Response to Office Action for U.S. Appl. No. 12/278,849, dated Jan. 9, 2014, 21 pages.
Response to Office Action for U.S. Appl. No. 12/278,849, filed Aug. 7, 2015, 24 pages.
Response to Office Action for U.S. Appl. No. 13/942,601, dated Feb. 4, 2014, 45 pages.
Response to Restriction Requirement for U.S. Appl. No. 10/148,041, filed Apr. 13, 2005, 10 pages.
Response to Restriction Requirement for U.S. Appl. No. 10/556,804, filed Jun. 29, 2009, 2 pages.
Response to Restriction Requirement for U.S. Appl. No. 10/562,843, filed Jun. 27, 2008, 2 pages.
Response to Restriction Requirement for U.S. Appl. No. 10/566,448, filed Dec. 1, 2008, 9 pages.
Response to Restriction Requirement for U.S. Appl. No. 10/566,448, filed Feb. 8, 2008, 9 pages.
Response to Restriction Requirement for U.S. Appl. No. 11/352,177, filed Mar. 13, 2009, 12 pages.
Response to Restriction Requirement for U.S. Appl. No. 11/352,177, filed Nov. 3, 2008, 8 pages.
Response to Restriction Requirement for U.S. Appl. No. 11/352,177, filed Jun. 9, 2008, 9 pages.
Response to Restriction Requirement for U.S. Appl. No. 11/733,737, filed Jan. 26, 2009, 8 pages.
Response to Restriction Requirement for U.S. Appl. No. 12/278,849, filed Sep. 28, 2010, 13 pages.
Restriction Requirement for U.S. Appl. No. 10/148,041, dated Mar. 10, 2005, 5 pages.
Restriction Requirement for U.S. Appl. No. 10/556,804, dated May 28, 2009, 5 pages.
Restriction Requirement for U.S. Appl. No. 10/562,843, dated Jun. 12, 2008, 6 pages.
Restriction Requirement for U.S. Appl. No. 10/566,448, dated Aug. 29, 2008, 7 pages.
Restriction Requirement for U.S. Appl. No. 10/566,448, dated Jan. 9, 2008, 5 pages.
Restriction Requirement for U.S. Appl. No. 11/352,177, dated Jan. 13, 2009, 10 pages.
Restriction Requirement for U.S. Appl. No. 11/352,177, dated Sep. 2, 2008, 5 pages.
Restriction Requirement for U.S. Appl. No. 11/352,177, dated Mar. 31, 2008, 8 pages.
Restriction Requirement for U.S. Appl. No. 11/733,737, dated Dec. 31, 2008, 9 pages.
Restriction Requirement for U.S. Appl. No. 12/278,849, dated May 28, 2010, 7 pages.
Search Report for GB 0317656.7, date of search Nov. 25, 2003, 1 page.
Search Report for GB 0621234.4, dated of search Feb. 21, 2007, 1 page.
Second Office Action for AU 17165/01, dated Mar. 21, 2006, 2 pages.
Second Office Action for CN 00818682.0, dated Jul. 28, 2006, 4 pages.
Summary of Office Action for MX PA/a/2002/005337, dated Jan. 3, 2007, 2 pages.
Supplemental Amendment for U.S. Appl. No. 11/352,177, filed Oct. 21, 2010, 15 pages.
Supplemental Response for U.S. Appl. No. 11/352, 177, filed Dec. 6, 2010, 4 pages.
Written Opinion received from International Preliminary Examining Authority for PCT Patent Application No. PCT/GB2004/002869, dated Jan. 12, 2005, 8 pages.
Written Opinion received from International Preliminary Examining Authority for PCT Patent Application No. PCT/GB2004/003263, dated Nov. 5, 2004, 5 pages.
Written Opinion received from International Preliminary Examining Authority for PCT Patent Application No. PCT/GB2007/000488, dated Jun. 6, 2007, 8 pages.
Written Opinion received from International Preliminary Examining Authority for PCT Patent Application No. PCT/GB2004/002021, dated Oct. 4, 2004, 5 pages.

* cited by examiner

| OX5034 Transgenic Strain | Doxycycline concentration (µg/ml) | Proportion of functional adults carrying the OX5034 transgene | |
|---|---|---|---|
| | | Males | Females |
| O4a | 0 | 95.7 | 0.0 (±0.0) |
| | 1 | 93.3 | 91.6 (±1.7) |
| S4a | 0 | 94.4 | 0.0 (±0.0) |
| | 1 | 93.4 | 95.1 (±1.4) |
| Latin WT | 0 | 92.7 | 96.5 (±1.7) |
| | 1 | 91.4 | 95.3 (±0.8) |

Figure 5

| Strain | Strain exclusion | | | | Selected as candidate strain |
|---|---|---|---|---|---|
| | Failed to produce a male-selecting phenotype | Disproportionate fluorescent : wt ratio | Reduced survival when carrying two copies of the transgene. | | |
| | | | Pupal stage | Adult stage | |
| A4a | | | | ✓ | |
| A4c | | | | ✓ | |
| C4a | | | | ✓ | |
| C4b | | | ✓ | | |
| C4c | | | | ✓ | |
| F4a | | ✓ | | | |
| F4b | ✓ | | | | |
| I4b | | | ✓ | | |
| I4c | | | ✓ | | |
| M4a | | | | ✓ | |
| O4a | | | | | ✓ "O" |
| O4b | | | ✓ | | |
| P4a | | | | ✓ | |
| P4b | | | ✓ | | |
| P4c | | | ✓ | | |
| R4a | ✓ | | | | |
| R4b | ✓ | | | | |
| S4a | | | | | ✓ "S" |
| S4b | ✓ | | | | |
| S4c | ✓ | | | | |

Figure 7

SELF-LIMITING, SEX-SPECIFIC GENE AND METHODS OF USING

CROSS REFERENCE TO RELATED APPLICATIONS

This application is a U.S. national phase of International Patent Application No. PCT/IB2017/001128, filed Aug. 9, 2017, which claims the benefit of priority to U.S. provisional patent applications 62/374,415, filed Aug. 12, 2016, entitled "A SELF-LIMITING, SEX-SPECIFIC GENE AND METHODS OF USING," 62/420,270, filed Nov. 10, 2016, entitled "A SELF-LIMITING, SEX-SPECIFIC GENE AND METHODS OF USING" and the contents of which are hereby incorporated by reference in their entirety for all purposes.

REFERENCE TO SEQUENCE LISTING

This application incorporates by reference a "Sequence Listing" (identified below) which was submitted in text file format via the U.S. Patent Office's Electronic Filing System (EFS). The text file copy of the Sequence Listing submitted was labeled 750402001300SeqList, a file of 78,749 bytes in size, and was created on Feb. 7, 2019; this Sequence Listing is incorporated by reference in its entirety herein.

BACKGROUND OF THE INVENTION

Alternative splicing plays a key role in the regulation of gene expression in many developmental processes ranging from sex determination to apoptosis (Black, D. L. (2003) *Annu. Rev. Biochem.* 72, 291-336), and defects in alternative splicing have been linked to many human disorders (Caceres, J. F. & Kornblihtt, A. R. (2002) *Trends Genet.* 18, 186-193). In general, alternative splicing is regulated by proteins that associate with the pre-mRNA and function to either enhance or repress the ability of the spliceosome to recognize the splice site(s) flanking the regulated exon (Smith, C. W. & Valcarcel, J. (2000) *Trends Biochem. Sci.* 25, 381-388).

Alternative splicing involves the removal of one or more introns and ligation of the flanking exons. This reaction is catalyzed by the spliceosome, a macromolecular machine composed of five RNAs, including small nuclear RNA and protein particles (snRNPs) which assemble with pre-mRNA to achieve RNA splicing, by removing introns from eukaryotic nuclear RNAs, thereby producing mRNA which is then translated to protein in ribosomes (Jurica, M. S. & Moore, M. J. (2003) *Mol. Cell* 12, 5-14; Smith, C. W. & Valcarcel, J. (2000) *Trends Biochem. Sci.* 25, 381-388). Alternative splicing generates multiple mRNAs from a single gene, thus increasing proteome diversity (Graveley, B. R. (2001) *Trends Genet.* 17, 100-107).

Whether a particular alternative exon will be included or excluded from a mature RNA in each cell is thought to be determined by the relative concentration of a number of positive and negative splicing regulators and the interactions of these factors with the pre-mRNA and components of the spliceosome (Smith, C. W. & Valcarcel, J. (2000) *Trends Biochem. Sci.* 25, 381-388).

Dengue fever is a viral disease primarily transmitted by the mosquito, *Aedes aegypti*, with an estimated incidence of 390 million infections annually (Bhatt et al., 2013). With no specific drugs available and a limited distribution of the licensed vaccine, Dengvaxia® (Villar et al, 2015, Constenia & Clark, 2016), efforts to reduce transmission depend predominantly on insecticide based vector control (WHO-TDR, 2009). *Aedes aegypti* also transmits other dangerous diseases such as yellow fever, chikungunya, and Zika. With the potential for the spread of insecticide resistance, the development of transgenic vectors may provide an effective method to limit the transmission of the disease by reducing the density or vectoral capacity of the vector population.

We have developed and tested a self-limiting technology that confers a repressible phenotype whereby, in the absence of a tetracycline analogue, all mosquitoes carrying a copy of the transgene die at an early larval stage due to the accumulation of tTAV protein produced by a positive feedback loop. Male mosquitoes, which do not bite or transmit disease, are selected and released to mate with wild females and therefore, the progeny, which inherit the self-limiting gene do not survive to adulthood due to the lack of tetracycline in the environment. In generating mosquitoes for release, the larvae and pupae are grown in the presence of tetracycline, wherein the mosquito pupae can mature to adulthood. However, in order to select only males, the pupae must be sorted by sex before eclosion.

Currently, the sex separation in *Aedes* mosquitoes is being done with a manual/mechanical procedure. While the procedure is very effective, it is extremely labour-intensive and human error can result in sexing errors. It is an inefficient method in medium to large-scale operational programs. We have pioneered in the development of mechanical sex sorters and methods for sorting larvae from pupae to facilitate the sex sort at scale, but these too require people and quality control to ensure efficient and accurate male production. Early and non-labour-intensive elimination of females could further enhance the cost saving benefit as potentially twice as many males could be produced from the same rearing environment as is currently possible.

There is a need in the art for a self-selecting separation procedure to increase the accuracy and efficiency of male/female separation.

BRIEF SUMMARY OF THE INVENTION

The invention provides a splice control module for differentially expressing a gene of interest in an organism.

The invention provides a doublesex (dsx) splice control module polynucleotide comprising, from 5' to 3':

a. an exon 4 of dsx;
b. a truncated intron 4 of dsx comprising a 5' terminal fragment of the dsx intron 4 and a 3' fragment of the dsx intron 4;
c. an exon 5a of dsx;
d. an intron 5 of dsx;
e. a modified exon 5b of dsx;
f. a truncated intron 6 of dsx comprising a 5' terminal fragment of the dsx intron 6 and a 3' fragment of the dsx intron 6; and
g. a 5' fragment of exon 6.

In some embodiments, the dsx splicing is derived from *Aedes aegypti* (Aeadsx).

In some embodiments, the dsx splice control module has a modified exon 5b in which an open reading frame is created for the entire exon. In some embodiments, the modified exon 5b comprises at least one substitution, insertion, and/or deletion to form an open reading frame for the entire exon.

The invention provides a dsx splice control module wherein splicing occurs on a sex-specific basis when introduced into an insect. In some embodiments, the insect is of the order selected from the group consisting of Diptera or Calliphoridae. In some embodiments, the insect is a dipteran selected from the group consisting of Medfly (*Ceratitis capitata*), Mexfly (*Anastrepha ludens*), Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha obliqua*).

In some embodiments, the dipteran insect is a mosquito of a genera selected from the group consisting of *Stegomyia, Aedes, Anopheles* and *Culex*. In specific embodiments, the mosquito is a species selected from the group consisting of *Stegomyia aegyptae* (also known as *Aedes aegypti*), *Stegomyia albopicta* (also known as *Aedes albopictus*), *Anopheles stephensi, Anopheles albimanus* and *Anopheles gambiae.*

In other embodiments, the insect is a Calliphoridae insect selected from the group consisting of New world screwworm (*Cochliomyia hominivorax*), Old world screwworm (*Chrysomya bezziana*) and Australian sheep blowfly (*Lucilia cuprina*). In other embodiments, the insect is a Lepidoptera insect selected from the group consisting of codling moth (*Cydia pomonella*), silk worm (*Bombyx mori*), pink bollworm (*Pectinophora gossypiella*), diamondback moth (*Plutella xylostella*), the Gypsy moth (*Lymantria dispar*), Navel Orange Worm (*Amyelois transitella*), Peach Twig Borer (*Anarsia lineatella*) rice stem borer (*Tryporyza incertulas*), and noctuid moths (e.g., Heliothinae).

In other embodiments, the insect is a Coleoptera insect selected from the group consisting of Japanese beetle (*Popilla japonica*), white-fringed beetle (*Graphognatus* spp.), boll weevil (*Anthonomous grandis*), corn root worm (*Diabrotica* spp.) and Colorado potato beetle (*Leptinotarsa decemlineata*).

In certain specific embodiments, the insect is the mosquito is *Aedes aegypti.*

The invention also provides a gene expression system comprising a polynucleotide comprising a doublesex (dsx) splice control module of the invention and a polynucleotide encoding heterologous protein. In some embodiments, the dsx splice control module is derived from *Aedes aegypti* (Aeadsx).

In some embodiments, the gene expression system of the invention further comprising a polynucleotide encoding a gene that is deleterious, lethal or sterilizing operably linked to 3' of said splice control module. In some embodiments, the gene is a synthetic tetracycline repressive transcriptional activator protein (tTAV). In some embodiments, the gene expression system further comprises a polynucleotide sequence encoding a Fusion Leader Polypeptide (e.g., ubiquitin) fused in frame to the 5' end of said polynucleotide encoding said tTAV. In some embodiments, the gene expression system further comprising a 5' untranslated region (5'UTR) operably linked 5' of said splice control module. In some embodiments, the 5'UTR comprises a promoter operable in an insect. In some embodiments, the promoter is a *Drosophila melanogaster* minimal HSP70 promoter (DmHsp70). In some embodiments, the 5'UTR further comprises a tetracycline responsive operator (e.g., TetOx7). In some embodiments, the gene expression system further comprising a 3' untranslated region (3'UTR) operably linked 3' of said tTAV. In some embodiments, the 3'UTR is an SV40 3'UTR.

The invention also provides an expression vector plasmid comprising a gene expression system of the invention. In some embodiments, the expression vector plasmid further comprises a polynucleotide encoding a fluorescent marker protein (e.g., DsRed2). In some embodiments, the polynucleotide encoding said fluorescent marker protein is operably linked to a promoter (e.g., an IE1 promoter). In some embodiments, the expression vector plasmid further comprises a piggyBac transposable element ends to direct incorporation of said expression vector plasmid into the chromosome of an organism.

The invention also provides a genetically engineered insect comprising a gene expression system incorporated into a chromosome of said insect, said gene expression system comprising a polynucleotide construct comprising:

a. a doublesex (dsx) splice control module wherein said splice control module comprises the components from 5' to 3':
b. an exon 4;
c. a truncated intron 4 of dsx comprising a 5' terminal fragment of the dsx intron 4 and a 3' fragment of the dsx intron 4;
d. an exon 5a;
e. an intron 5 of dsx;
f. a modified exon 5b of said dsx;
g. a truncated intron 6 of dsx comprising a 5' terminal fragment of the dsx intron 6 and a 3' fragment of the dsx intron 6; and
h. a 5' fragment of exon 6;
i. a polynucleotide encoding ubiquitin fused in frame to the 5' end of a polynucleotide encoding tTAV positioned 3' of said splice control module; and
j. a 5'UTR positioned 5' of said splice control module wherein said 5'UTR comprises a tetracycline responsive operator (TetO x7) and a promoter.

In some embodiments, the genetically engineered insect is a mosquito, such as one of a genera selected from the group consisting of *Aedes, Anopheles*, and *Culex*. In some embodiments, the mosquito is *Aedes aegypti.*

In some embodiments, the genetically engineered insect further comprises a polynucleotide encoding a fluorescent protein (e.g., DsRed2). In some embodiments, the fluorescent protein is operably linked to a promoter (e.g., an IE1 promoter).

The invention also provides a method of producing genetically engineered insects comprising modifying an insect's chromosome by inserting a gene expression system, wherein said gene expression system comprises:

a. a doublesex (dsx) splice control module wherein said splice control module comprises the components from 5' to 3':
b. an exon 4;
c. a truncated intron 4 of dsx comprising a 5' terminal fragment of the dsx intron 4 and a 3' fragment of the dsx intron 4;
d. an exon 5a;
e. an intron 5 of dsx;
f. a modified exon 5b of said dsx;
g. a truncated intron 6 of dsx comprising a 5' terminal fragment of the dsx intron 6 and a 3' fragment of the dsx intron 6; and
h. a 5' fragment of exon 6;
i. a polynucleotide encoding ubiquitin fused in frame to the 5' end of a polynucleotide encoding tTAV positioned 3' of said splice control module; and
j. a 5'UTR positioned 5' of said splice control module wherein said 5'UTR comprises a tetracycline responsive operator (TetO x7) and a promoter.

In some embodiments of the method of the invention, the insect is a mosquito of a genus selected from the group consisting of *Aedes, Anopheles*, and *Culex*. In some embodiments, the mosquito is *Aedes aegypti*.

In some embodiments of the method of the invention, the gene expression system further comprises a polynucleotide encoding a fluorescent protein (e.g., DsRed2). In some embodiments, the fluorescent protein is operably linked to a promoter (e.g., an IE1 promoter).

The invention also provides a method of selectively rearing male genetically engineered insects comprising, rearing a genetically engineered insect of the invention in the absence of tetracycline.

The invention also provides a genetically engineered male insect produced by the method of the invention.

The invention also provides a method of reducing a wild insect population comprising contacting said wild insect population with a plurality of the male genetically engineered insects of the invention wherein said male genetically engineered insects mate with wild female insects of the same species. In some embodiments, the insect is a mosquito of a genus selected from the group consisting of *Aedes, Anopheles*, and *Culex*. In some embodiments, the mosquito is *Aedes aegypti*.

BRIEF DESCRIPTION OF THE DRAWINGS

FIG. 5 shows the proportion of functional DSX-tTAV-Red adults surviving from on-off doxycycline rearing of DSX-tTAV-Red-O and DSX-tTAV-Red-S. Percentages are means of individuals becoming functional adults, based on the number of fluorescent pupae collected per strain. 95% confidence intervals are displayed in parentheses for female samples. Male samples were pooled (see methods section).

FIG. 7 shows a summary of the criteria for the strain selection that resulted in DSX-tTAV-Red-O and DSX-tTAV-Red-S.

DETAILED DESCRIPTION OF THE INVENTION

Definitions

This description contains citations to various journal articles, patent applications and patents. These are herein incorporated by reference as if each was set forth herein in its entirety.

The term "penetrance," as used herein, refers to the proportion of individuals carrying a particular variant of a gene that also express the phenotypic trait associated with that variant. Thus, "penetrance", in relation to the present invention, refers to the proportion of transformed organisms which express the lethal phenotype.

The term "construct," as used herein, refers to an artificially constructed segment of DNA for insertion into a host organism, for genetically modifying the host organism. At least a portion of the construct is inserted into the host organism's genome and alters the phenotype of the host organism. The construct may form part of a vector or be the vector.

Figure 1:
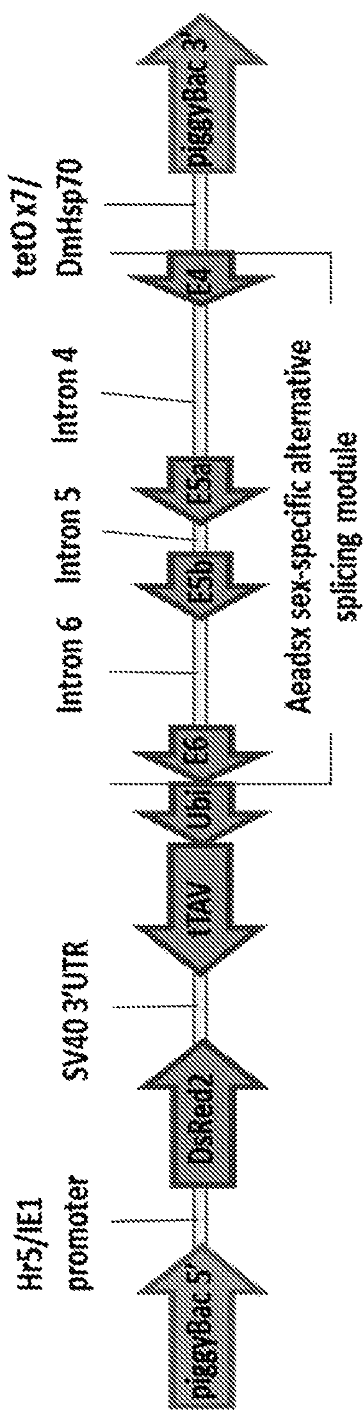
FIG. 1 shows two gene cassettes are present in the rDNA of DSX-tTAV-Red. One expresses the fluorescent marker, DsRed2 and the other expresses the tTAV protein female-specifically. Exons are expressed as E4, E5a, E5b, and E6. Hr5/IE1 are the promoter/Enhancer from the Baculovirus *Autographica californica* nucleopolyhedrosisvirus (AcNPV), DmHSP70 is the HSP70 gene from *Drosophila melanogaster*.

The term "transgene," as used herein, refers to the polynucleotide sequence comprising a first and a second gene expression system to be inserted into a host organism's genome, to alter the host organism's phenotype. The portion of the plasmid vector containing the genes to be expressed (as shown in FIG. 1, for example) is referred to herein as the transfer DNA or recombinant DNA (rDNA).

The term "gene expression system," as used herein, refers to a gene to be expressed together with any genes and DNA sequences which are required for expression of said gene to be expressed.

The term "splice control sequence," as used herein, refers to a DNA sequence associated with a gene, wherein the DNA sequence, together with a spliceosome, mediates alternative splicing of a RNA product of said gene. Preferably, the splice control sequence, together with the spliceosome, mediates splicing of a RNA transcript of the associated gene to produce an mRNA coding for a functional protein and mediates alternative splicing of said RNA transcript to produce at least one alternative mRNA coding for a non-functional protein. A "splice control module" may contain multiple splice control sequences that join multiple exons to form a polypeptide encoding nucleic acid.

The term "transactivation activity," as used herein, refers to the activity of an activating transcription factor, which results in an increased expression of a gene. The activating transcription factor may bind a promoter or operator operably linked to said gene, thereby activating the promoter and, consequently, enhancing the expression of said gene. Alternatively, the activating transcription factor may bind an enhancer associated with said promoter, thereby promoting the activity of said promoter via said enhancer.

The term "lethal gene," as used herein, refers to a gene whose expression product has a lethal effect, in sufficient quantity, on the organism within which the lethal gene is expressed.

The term "lethal effect," as used herein, refers to a deleterious or sterilising effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

The term "tTAV gene variant," as used herein, refers to a polynucleotide encoding the functional tTA protein but which differ in the sequence of nucleotides. These nucleotides may encode different tTA protein sequences, such as, for example, tTAV2 and tTAV3.

The term "promoter," as used herein, refers to a DNA sequence, generally directly upstream to the coding sequence, required for basal and/or regulated transcription of a gene. In particular, a promoter is sufficient to allow initiation of transcription, generally having a transcription initiation start site and a binding site for the RNA polymerase transcription complex.

The term "minimal promoter," as used herein, refers to a promoter as defined above, generally having a transcription initiation start site and a binding site for the polymerase complex, and further generally having sufficient additional sequence to permit these two to be effective. Other sequences, such as that which determines tissue specificity, for example, may be lacking.

The term "exogenous control factor," as used herein, refers to a substance which is not found naturally in the host organism and which is not found in a host organism's natural habitat, or an environmental condition not found in a host organism's natural habitat. Thus, the presence of the exogenous control factor is controlled by the manipulator of a transformed host organism in order to control expression of the gene expression system.

The term "tetO element," as used herein, refers to one or more tetO operator units positioned in series. The term, for example, "tetOx(number)," as used herein, refers to a tetO element consisting of the indicated number of tetO operator units. Thus, references to "tetOx7" indicates a tetO element consisting of seven tetO operator units. Similarly, references to "tetOx14" refers to a tetO element consisting of 14 tetO operator units, and so on.

The term "tra intron," as used herein, refers to a splice control sequence wherein alternative splicing of the RNA transcript is regulated by the tra protein, for instance binding thereof, alone or in combination (i.e., when complexed) with TRA2.

Where reference to a particular nucleotide or protein sequence is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences.

However, it will be understood that despite the above sequence homology, certain elements, in particular the flanking nucleotides and splice branch site must be retained, for efficient functioning of the system. In other words, whilst portions may be deleted or otherwise altered, alternative splicing functionality or activity, to at least 30%, preferably 50%, preferably 70%, more preferably 90%, and most preferably 95% compared to the wild type should be retained. This could be increased compared to the wild type, as well, by suitably engineering the sites that bind alternative splicing factors or interact with the spliceosome, for instance.

As used herein, "splice control module" means a polynucleotide construct in that is incorporated into a vector that, when introduced into an insect, undergoes differential splicing (e.g., stage-specific, sex-specific, tissue-specific, germline-specific, etc.) and thus creates a different transcript in females than males if the splice control module confers differential splicing in a sex-specific manner.

As used herein, doublesex (dsx) refers to a gene in both male and female insects, such as Diptera that is subject to alternative splicing.

As used herein, "5'UTR," refers to an untranslated region of an RNA transcript that is 5' of the translated portion of the transcript and often contains a promoter sequence.

As used herein, "3'UTR," refers to an untranslated region of an RNA transcript that is 3' of the translated portion of the transcript and often contains a polyadenylation sequence.

A. Overview of the Technology

The invention provides constructs and methods for differentially expressing proteins in insects in a sex-specific manner such that either a male insect or a female insect will express the protein and the other will not. The constructs of the invention have been engineered with a splice control module that is spliced differently in male insects than female insects. The splice control module may be operably linked to a heterologous protein-encoding polynucleotide such that the heterologous protein of interest is expressed in a sex-specific manner when introduced into an insect species. The constructs of the invention also may contain other elements for regulating expression in an insect, for identifying insects that have an integrated construct in their genome, and for selecting transformed cells, for example as will be described more fully below.

i. The Splice Control Module

Thus, in a first aspect, the present invention provides a splice control module polynucleotide sequence which provides for differential splicing (e.g., sex-specific, stage-specific, germline-specific, tissue-specific, etc.) in an organism. In particular, the invention provides a splice control module which provides for sufficient female-specificity of the expression of a gene of interest to be useful. In certain embodiments of the invention, the gene of interest is a gene that imparts a deleterious, lethal or sterilizing effect. For convenience, the description will refer to a lethal effect, however, it will be understood that the splice module may be used on other genes of interest as described in further detail below.

Expression of the dominant lethal genes of the transgene may be sex-specific, or be a combination of sex-specific and stage-specific, germline-specific or tissue-specific, due to the presence of at least one splice control module in each gene expression system operably linked to a gene of interest to be differentially expressed. In some embodiments, the sex-specific expression is female-specific. The splice control module in each gene expression sequence allows an additional level of control of protein expression, in addition to the promoter.

The gene of the splice control module comprises a coding sequence for a protein or polypeptide, i.e., at least one exon, and preferably two or more exons, capable of encoding a polypeptide, such as a protein or fragment thereof. Preferably, the different exons are differentially spliced together to provide alternative mRNAs. Preferably, said alternative spliced mRNAs have different coding potential, i.e., encode different proteins or polypeptide sequences. Thus, the expression of the coding sequence is regulated by alternative splicing.

Each splice control module in the system comprises at least one splice acceptor site and at least one splice donor site. The number of donor and acceptor sites may vary, depending on the number of segments of sequence that are to be spliced together.

In some embodiments, the splice control module regulates the alternative splicing by means of both intronic and exonic nucleotides. It will be understood that in alternative splicing, sequences may be intronic under some circumstances (i.e., in some alternative splicing variants where introns are spliced out), but exonic under other. In other embodiments, the splice control module is an intronic splice control module. In other words, it is preferred that said splice control sequence is substantially derived from polynucleotides that form part of an intron and are thus excised from the primary transcript by splicing, such that these nucleotides are not retained in the mature mRNA sequence.

As mentioned above, exonic sequences may be involved in the mediation of the control of alternative splicing, but it is preferred that at least some intronic control sequences are involved in the mediation of the alternative splicing.

The splice control module may be removed from the pre-RNA, by splicing or retained so as to encode a fusion protein of at least a portion of the gene of interest to be differentially expressed. Preferably, the splice control module does not result in a frameshift in the splice variant produced. Preferably, this is a splice variant encoding a full-length functional protein.

Interaction of the splice control module with cellular splicing machinery, e.g., the spliceosome, leads to or mediates the removal of a series of, preferably, at least 50 consecutive nucleotides from the primary transcript and ligation (splicing) together of nucleotide sequences that were not consecutive in the primary transcript (because they, or their complement if the antisense sequence is considered, were not consecutive in the original template sequence from which the primary transcript was transcribed). Said series of at least 50 consecutive nucleotides comprises an intron. This mediation acts preferably in a sex-specific, more preferably, female-specific, manner such that equivalent primary transcripts in different sexes, and optionally also in different stages, tissue types, etc., tend to remove introns of different size or sequence, or in some cases may remove an intron in one case but not another. This phenomenon, the removal of introns of different size or sequence in different circumstances, or the differential removal of introns of a given size or sequence, in different circumstances, is known as alternative splicing. Alternative splicing is a well-known phenomenon in nature, and many instances are known.

Where mediation of alternative splicing is sex-specific, it is preferred that the splice variant encoding a functional protein to be expressed in an organism is the F1 splice variant, i.e., a splice variant where the F denotes it is found only or predominantly in females, although this is not essential.

When exonic nucleotides are to be removed, then these must be removed in multiples of three (entire codons), if it is desired to avoid to avoid a frameshift, but as a single nucleotide or multiples of two (that are not also multiples of three) if it is desired to induce a frameshift. It will be appreciated that if only one or certain multiples of two nucleotides are removed, then this could lead to a completely different protein sequence being encoded at or around the splice junction of the mRNA.

This is particularly the case in an embodiment of the system where cassette exons are used to interrupt an open reading frame in some splice variants but not others, such as in, for example, tra, especially Cctra (see below).

Correspondingly for configurations where all or part of a functional open reading frame is on a cassette exon, it is preferred that this cassette exon is included in transcripts found only or predominantly in females, and preferably such transcripts are, individually or in combination, the most abundant variants found in females, although this is not essential.

In one preferred embodiment, sequences are included in a hybrid or recombinant sequence or construct which are derived from naturally occurring intronic sequences which are themselves subject to alternative splicing, in their native or original context. Therefore, an intronic sequence may be considered as one that forms part of an intron in at least one alternative splicing variant of the natural analogue. Thus, sequences corresponding to single contiguous stretches of naturally occurring intronic sequence are envisioned, but also hybrids of such sequences, including hybrids from two different naturally occurring intronic sequences, and also sequences with deletions or insertions relative to single contiguous stretches of naturally occurring intronic sequence, and hybrids thereof. Said sequences derived from naturally occurring intronic sequences may themselves be associated, in the invention, with sequences not themselves part of any naturally occurring intron. If such sequences are transcribed, and preferably retained in the mature RNA in at least one splice variant, they may then be considered exonic.

It will also be appreciated that reference to a "frame shift" could also refer to the direct coding of a stop codon, which is also likely to lead to a non-functioning protein as would a disruption of the spliced mRNA sequence caused by insertion or deletion of nucleotides. Production from different splice variants of two or more different proteins or polypeptide sequences of differential function is also envisioned, in addition to the production of two or more different proteins or polypeptide sequences of which one or more has no predicted or discernable function. Also envisioned is the production from different splice variants of two or more different proteins or polypeptide sequences of similar function, but differing subcellular location, stability or capacity to bind to or associate with other proteins or nucleic acids.

Preferred examples of this include a modified dsx intron. In this instance, it may be preferable to delete, as we have done in the Examples, sizable amounts from alternatively spliced introns, e.g., 90% or more of an intron in some cases, whilst still retaining the alternative splicing function. Thus, whilst large deletions are envisioned, it is also envisaged that smaller, e.g., even single nucleotide insertions, substitutions or deletions are also preferred.

ii. Examples of Splice Modules a. Tra Sequences

As mentioned above, in some embodiments the manner or mechanism of alternative splicing is sex-specific, preferably female-specific, and any suitable splice control sequence may be used. In some embodiments, at least one splice control module is derived from a tra intron. The *Ceratitis capitata* tra intron from the transformer gene was initially characterised by Pane et al. (2002) *Development* 129:3715-3725. In insects, for instance, the tra protein is differentially expressed in different sexes. In particular, the tra protein is known to be present largely in females and, therefore, mediates alternative splicing in such a way that a coding sequence is expressed in a sex-specific manner, i.e., that in some cases a protein is expressed only in females or at a much higher level in females than in males or, alternatively, in other cases a protein is expressed only in males, or at a much higher level in males than in females. The mechanism for achieving this sex-specific alternative splicing mediated by the tra protein or the TRA/TRA-2 complex is known and is discussed, for instance, in Pane et al. (2002) *Development* 129:3715-3725.

It will be appreciated that homologues of the *Ceratitis capitata* tra intron from the transformer gene exist in other species, and these can be easily identified in said species and also in their various genera. Thus, when reference is made to tra it will be appreciated that this also relates to tra homologues in other species. Thus, in some embodiments each of the alternative splicing mechanisms is independently derived from the *Ceratitis capitata* tra intron (Cctra), or from another ortholog or homolog. In some embodiments, the ortholog or homologue is from an arthropod, such as an insect of the order Diptera, such as a tephritid. In other embodiments, the ortholog or homologue is from the genus *Cochliomyia, Glossina, Lucilia, Musca, Ceratitis, Bactrocera, Anastrepha* or *Rhagoletis*. In other embodiments, the ortholog or homolog is from *Ceratitis rosa*, or *Bactrovera zonata*. In further embodiments, the ortholog or homolog is from *B. zonata*, and this ortholog or homolog is referred to herein as Bztra (GenBank accession number BzTra KJ397268). Orthologs may also be from the Order Hymenoptera, or Coleoptera. Examples, include, but are not limited to *Apis cerana, Apis dorsata, Apis florea, Apis mellifera, Atta cephalotes, Bombus impatiens, Bombus terrestris, Camponotus floridanus, Euglossa hemichlora, Harpegnathos saltator, Linepithema humile, Melipona compressipes, Megachile rotundata, Nasonia giraulti, Nasonia longicornis, Nasonia vitripennis, Pogonomyrmex barbatus, Solenopsis invicta*, and *Tribolium castaneum.*

The splicing pattern in Cctra in particular is well conserved, with those transcripts found in males containing additional exonic material relative to the F1 transcript, such that these transcripts do not encode full-length, functional tra protein. By contrast, the F1 transcript does encode full-length, functional tra protein; this transcript is substantially female-specific at most life-cycle stages, though it is speculated that very early embryos of both sexes may contain a small amount of this transcript. We describe the sequence spliced out of the F1 transcript, but not the male-specific or non-sex-specific transcripts, as the tra intron, or even the tra F1 intron. Thus the version of this sequence found in the Cctra gene is the Cctra intron.

Thus the tra gene is regulated in part by sex-specific alternative splicing, while its key product, the tra protein, is itself involved in alternative splicing. In insects, sex-specific alternative splicing mediated by the tra protein, or a complex comprising the tra and TRA2 proteins, include Dipteran splice control sequences derived from the doublesex (dsx) gene and also the tra intron itself, although this would exclude the tra intron from *Drosophila* (Dmtra), which is principally mediated by the Sxl gene product in *Drosophila*, rather than tra or the TRA/TRA2 complex. Outside of *Drosophila*, the Sxl gene product is not differentially expressed in the different sexes. Sxl is not thought to act in the mediation of sex-specific alternative splicing in non-Drosophilid insects.

By "derived" it will be understood that, using reference to the tra intron, this refers to sequences that approximate to or replicate exactly the tra intron, as described in the art, in this case by Pane et al. (2002), supra. However, it will be appreciated that, as these are intronic sequences, that some nucleotides can be added or deleted or substituted without a substantial loss in function.

If more than one splice control module is incorporated into a gene expression system of the invention, the splice control module may be the same or different. In some embodiments, it is preferred that the splice control modules are derived from different species in order to reduce the risk of recombination. Thus, in some embodiments, one of the first and second splice control sequences is Cctra and the other is derived from a different species. In one embodiment, one of the first and second splice control sequences is Cctra and the other is Bztra (GenBank accession number BzTra KJ397268).

In a particular embodiment, the first splice control sequence is Cctra and the second splice control sequence is Bztra (GenBank accession number BzTra KJ397268). The exact length of the splice control sequence derived from the tra intron is not essential, provided that it is capable of mediating alternative splicing. In this regard, it is thought that around 55 to 60 nucleotides is the minimum length for a modified tra intron, although the wild type tra intron (F1 splice variant) from *C. capitata* is in the region of 1345 nucleotides long.

b. Actin-4

In other embodiments, at least one of the splice control sequences is derived from the alternative splicing mechanism of the Actin-4 gene derived from an arthropod, preferably a tephritid. In embodiments wherein more than one splice sequence is derived from Actin-4, they may be derived from the same or from different tephritid species. In some embodiments, each Actin-4 gene is independently derived from a species of the *Ceratitis*, the *Bactrocera*, the *Anastrepha* or the *Rhagoletis* genera. In other embodiments, the first and second Actin-4 genes are independently derived from *Ceratitis capitata, Bactrocera oleae, Ceratitis rosa* or *Bactrocera zonata*. In some embodiments, at least one of the first and second Actin-4 genes is derived from *Ceratitis capitata*. In embodiments wherein more than one splice control sequence is derived from Actin-4, the splice control sequences may be derived from the same species. However, it is preferred that the splice control sequences are derived from different species in order to reduce recombination.

c. Doublesex

In some embodiments, at least one of the splice control sequences comprises at least a fragment of the doublesex (dsx) gene derived from an arthropod, such as a tephritid. In some embodiments, more than one splice control sequence (e.g., both the first and second splice control sequences) is derived from dsx, and the dsx genes are derived from the same or different species. In some embodiments, the dsx gene is derived from a species of the Order Diptera, such as, but not limited to those of the genus *Aedes, Anopheles, Cochliomyia, Culex, Drosophila, Glossina, Lucilia, Lutzomyia, Ceratitis, Bactrocera, Anastrepha, Mayetiola, Megaselia, Musca, Phlebotomus* and *Rhagoletis*. In some embodiments, the dsx genes are independently derived from *Aedes aegypti, Anopheles* spp., *Anopheles gambiae, Anastrepha* spp., *Ceratitis capitata, Bactrocera oleae, Bactrocera dorsalis, Bactrocera zonata, Bactrocera correcta, Bactrocera tryoni, Ceratitis rosa, Cochliomyia homnivorax, Cochliomyia macellaria, Culex quinquefasciatus, Drosophila Americana, Drosophila erecta, Drosophila hydei, Drosophila mauritania, Drosophila melanogaster, Drosophila sechellia, Drosophila simulans, Drosophila virilis, Glossina morsitans, Lucilia cuprina, Lucilia sericata, Lutzomyia longipalpis, Mayetiola destructor, Megaselia scalaris, Musca domestica*, and *Phlebotomus papatasi*.

In some embodiments, the dsx gene is derived from a species of the Order Phtiraptera, such as, for example, *Pediculus humanus corporis*.

In some embodiments, the dsx gene is derived from a species of the Order Hemiptera, including such species as, but not limited to *Acyrthosiphon pisum* and *Rhodnius prolixus*.

In some embodiments, the dsx gene is derived from a species of the Order Hymenoptera, including, but not limited to insects of the genera *Apis, Atta, Bombus, Camponotus, Euglossa, Harpegnathos, Linepithema, Melipona, Megachile, Nasonia, Pogonomyrmex*, and *Solenopsis*. Examples of suitable species, include, but are not limited to *Apis cerana, Apis dorsata, Apis florea, Apis mellifera, Atta cephalotes, Bombus impatiens, Bombus terrestris, Camponotus floridanus, Euglossa hemichlora, Harpegnathos saltator, Linepithema humile, Melipona compressipes, Megachile rotundata, Nasonia giraulti, Nasonia longicornis, Nasonia vitripennis, Pogonomyrmex barbatus, Solenopsis invicta.*

In some embodiments, the dsx gene is derived from a species of the Order Lepidoptera, including but not limited to insects of the genera *Antheraea, Bombyx, Danaus, Heliconius*, and *Ostrinia*. Examples of suitable species, include, but are not limited to *Antheraea assama, Antheraea mylitta, Bombyx mori, Danaus plexippus, Heliconius Melpomene, Plutella xylostella, Pectinophora gossypiella* and *Ostrinia scapulalis.*

In some embodiments, the dsx gene is derived from a species of the Order Coleoptera, including, but not limited to insects of the genera *Dendroctonus, Onthophagus*, and *Tribolium*. Examples of suitable species, include, but are not limited to *Dendroctonus ponderosae, Onthophagus sagittarius, Onthophagus taurus*, and *Tribolium castaneum.*

In some embodiments, the dsx gene is derived from a species of the Order Strepsiptera, including, but not limited to insects of the genus *Mengenilla* (e.g., *Mengenilla moldrzyki*).

In some embodiments, at least one of the first and second dsx genes is derived from the same insect, such as, for example, *Aedes aegypti*. In embodiments wherein more than one splice control sequence is derived from dsx, the splice control sequences may be derived from the same species. In other embodiments, the splice control sequences are derived from different species.

In one embodiment, the present invention provides a doublesex (dsx) splice control module polynucleotide wherein the splice control module comprises (from 5' to 3'): at least a portion of an exon 4 of dsx, preferably the entire exon (an example is shown for *Aedes aegypti* as SEQ ID NO:13), a truncated intron 4 of dsx comprising at least a 5' terminal fragment of the dsx intron 4 that contains at least a portion of the 5' end of intron 4 (an example is shown for *Aedes aegypti* as SEQ ID NO:12) and a 3' fragment of the dsx intron 4 that contains at least a portion of the 3' end of intron 4 (an example is shown for *Aedes aegypti* as SEQ ID NO:11), at least a portion of an exon 5a of dsx, preferably the entire exon 5a (an example is shown for *Aedes aegypti* as SEQ ID NO:6), at least a portion of an intron 5 of dsx, preferably the entire intron 5 (an example is shown for *Aedes aegypti* as SEQ ID NO:10), a modified exon 5b of dsx (an example is shown for *Aedes aegypti* as SEQ ID NO:7), a truncated intron 6 that contains at least a portion of the 5' end of intron 6 of dsx (an example is shown for *Aedes aegypti* as SEQ ID NO:9) linked to at least a portion of the 3' fragment of intron 6 of dsx (an example is shown for *Aedes aegypti* as SEQ ID NO:8) forming a truncated intron 6, and at least a portion of the 5' region of an exon 6 of dsx (an example is shown for *Aedes aegypti* as SEQ ID NO:5).

Figure 3:
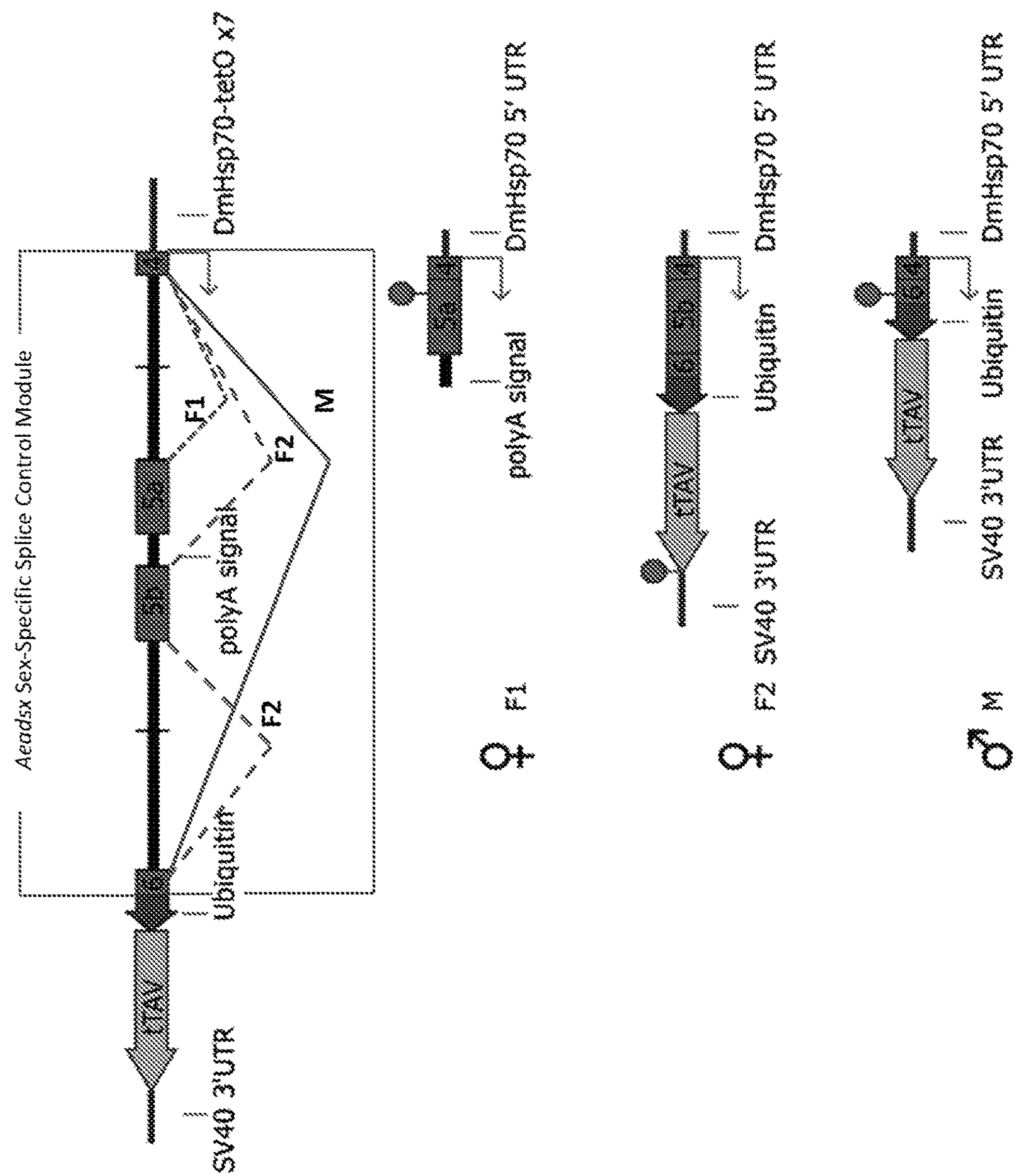
FIG. 3 shows the splicing behaviour of the Aeadsx splice control module in DSX-tTAV-Red strains. The Aeadsx splice module consists of Aeadsx exons 4, 5a, 5b and 6, together with fragments of Aeadsx introns 4 and 5. The F1 transcript contains Aeadsx exon 4 joined to Aeadsx exon 5a and part of Aeadsx intron 5 (serves as a 3'UTR with an internal termination and polyadenylation (polyA) signal). This transcript has a short open reading frame (ORF) that starts immediately upstream to Aeadsx exon 4 and ends at a stop codon in Aeadsx exon 5a. F2 transcript contains Aeadsx exon 4, Aeadsx a modified exon 5b, a truncated Aeadsx exon 6, Ubiquitin and SV40 3'UTR. This transcript has a long ORF, starts upstream to Aeadsx exon 4 and ends immediately after the 3' end of tTAV encoding sequence. Transcript M contains Aeadsx exon 4, Aeadsx exon 6, Ubiquitin, tTAV and SV40 3'UTR. The ORF in this transcript starts, as in the other two transcripts, upstream to Aeadsx exon 4 and ends in Ubiquitin sequence (in a frame different than the ORF coding for Ubiquitin protein). The arrow indicates the position of the start codon and the red stop sign indicates that of the stop codon.

The dsx splice control module allows a sex-specific splicing of the module to a polypeptide encoding polynucleotide such that the polypeptide is expressed in a sex-specific manner. In a specific example, two principle transcripts are made in female *Aedes*: Transcript F1 contains exon 4, 5a, and intron 5, which acts as a 3' UTR and contains a polyadenylation signal; Transcript F2 contains exon 4, exon 5b and truncated exon 6 together with the heterologous gene of interest in frame with the rest of the transcript and with the translation start site 5' to exon 4. In the male *Aedes*, the splice form contains exon 4 and exon 6, but the heterologous gene of interest is out of frame with the translation start site 5' to exon 4 (FIG. 3).

While in some embodiments it is envisaged that the splice control modules are derived from the same gene or intron of origin, in other embodiments the splice control modules are derived from different genes or introns of origin. For example, in some embodiments, one of the splice control modules is derived from the tra intron and the other splice control module is derived from the Actin-4 gene or the dsx gene.

Preferably, the splice control module is 3' to the start codon. Where the splice control module is 3' to the start codon, it is preferred that it is also 5' to the first in-frame stop codon (that is 3' to and in frame with the start codon), so that alternative splicing yields transcripts that encode different protein or polypeptide sequences. Thus in a preferred embodiment, the construct or polynucleotide sequence comprises the following elements in 5' to 3' order, with respect to the sense strand or primary transcript: transcription start, translation start, intron capable of alternative splicing, coding sequence for all or part of a protein, stop codon.

iii. Splicing

Introns typically consist of the following features (given here as the sense DNA sequence 5' to 3'); in RNA thymine (T) will be replaced by uracil (U)):

a. 5' end (known as the splice "donor"): GT (or possibly GC)

b. 3' end (known as the splice "acceptor"): AG c. Upstream/5' of the acceptor (known as the "branch point"): A-polypyrimidine tract, i.e. AYYYYY . . . $Y_n$ The terminal nucleotides of exons immediately adjacent to the 5' intronic splice "donor" and the 3' intronic splice "acceptor" are typically G.

In some embodiments, the splice control module is immediately adjacent, in the 3' direction, the start codon, so that the G of the ATG is 5' to the start (5' end) of the splice control module. This may be advantageous as it allows the G of the ATG start codon to be the 5' G flanking sequence to the splice control module.

Alternatively, the splice control module is 3' to the start codon but within 10,000 exonic bp, 9,000 exonic bp, 8,000 exonic bp, 7,000 exonic bp, 6,000 exonic bp, 5,000 exonic bp, 4,000 exonic bp, exonic 3,000 bp, exonic 2000, bp, or 1000 exonic bp, preferably 500 exonic bp, preferably 300 exonic bp, preferably 200 exonic bp, preferably 150 exonic bp, preferably 100 exonic bp, more preferably 75 exonic bp, more preferably 50 exonic bp, more preferably 30 exonic bp, more preferably 20 exonic bp, and most preferably 10 or even 5, 4, 3, 2, or 1 exonic bp.

Preferably, branch points are included in each splice control sequence, as described above. A branch point is the sequence to which the splice donor is initially joined which shows that splicing occurs in two stages, in which the 5' exon is separated and then is joined to the 3' exon.

The sequences provided can tolerate some sequence variation and still splice correctly. There are a few nucleotides known to be important. These are the ones required for all splicing. The initial GU and the final AG of the intron are particularly important and therefore preferred, as discussed elsewhere, though ~5% of introns start GC instead. This consensus sequence is preferred, although it applies to all splicing, not specifically to alternative splicing.

iv. Heterologous Genes of Interest

The system is capable of expressing at least one protein of interest, i.e., said functional protein to be expressed in an organism. Said at least one protein of interest may have a therapeutic effect or may, be a marker (for instance DsRed, Green Fluorescent Protein (GFP) or one or more of their mutants or variants), or other markers that are well known in the art such as drug resistance genes. Other proteins of interest may be, for example, proteins that have a deleterious, lethal or sterilizing effect. Alternatively, a gene of interest may encode an RNA molecule that has an inhibitory effect. Further proteins to be expressed in the organism are, or course envisaged, in combination with said functional protein, preferably a lethal gene as discussed below.

It is preferred that the expression of the heterologous polynucleotide sequence leads to a phenotypic consequence in the organism. In some embodiments, the functional protein is not beta-galactosidase, but can be associated with visible markers (including fluorescence), viability, fertility, fecundity, fitness, flight ability, vision, and behavioural differences. It will be appreciated, of course, that, in some embodiments, the expression systems are typically conditional, with the phenotype being expressed only under some, for instance restrictive, conditions.

The at least one heterologous polynucleotide sequence to be expressed in an organism is a heterologous sequence. By "heterologous," it would be understood that this refers to a sequence that would not, in the wild type, be normally found in association with, or linked to, at least one element or component of the at least one splice control sequence. For example, where the splice control sequence is derived from a particular organism, and the heterologous polynucleotide is a coding sequence for a protein or polypeptide, i.e., is a polynucleotide sequence encoding a functional protein, then the coding sequence could be derived, in part or in whole, from a gene from the same organism, provided that that the origin of at least some part of the transcribed polynucleotide sequence was not the same as the origin of the at least one splice control sequence. Alternatively, the coding sequence could be from a different organism and, in this context, could be thought of as "exogenous". The heterologous polynucleotide could also be thought of as "recombinant," in that the coding sequence for a protein or polypeptide are derived from different locations, either within the same genome (i.e., the genome of a single species or sub-species) or from different genomes (i.e., genomes from different species or subspecies), or synthetic sources.

Heterologous can refer to a sequence other than the splice control sequence and can, therefore, relate to the fact the promoter, and other sequences such as 5' UTR and/or 3'UTR can be heterologous to the polynucleotide sequence to be expressed in the organism, provided that said polynucleotide sequence is not found in association or operably linked to the promoter, 5' UTR and/or 3'UTR, in the wild type, i.e., the natural context of said polynucleotide sequence, if any.

It will be understood that heterologous also applies to "designer" or hybrid sequences that are not derived from a particular organism but are based on a number of components from different organisms, as this would also satisfy the requirement that the sequence and at least one component of the splice control sequence are not linked or found in association in the wild type, even if one part or element of the hybrid sequence is so found, as long as at least one part or element is not. It will also be understood that synthetic versions of naturally occurring sequences are envisioned. Such synthetic sequences are also considered as heterologous, unless they are of identical sequence to a sequence which would, in the wild type or natural context, be normally found in association with, or linked to, at least one element or component of the at least one splice control sequence.

This applies equally to where the heterologous polynucleotide is a polynucleotide for interference RNA.

In one embodiment, where the polynucleotide sequence to be expressed comprises a coding sequence for a protein or polypeptide, it will be understood that reference to expression in an organism refers to the provision of one or more transcribed RNA sequences, preferably mature mRNAs, but this may, preferably, also refer to translated polypeptides in said organism.

a. Lethal Genes

In some embodiments, the functional protein to be expressed in an organism has a lethal, deleterious or sterilizing effect. Where reference is made herein to a lethal effect, it will be appreciated that this extends to a deleterious or sterilizing effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

A lethal effect resulting in sterilization is particularly preferred, as this allows the organism to compete in the natural environment ("in the wild") with wild-type organisms, but the sterile insect cannot then produce viable offspring. In this way, the present invention achieve a similar or better result to techniques such as the Sterile Insect Technique (SIT) in insects, without the problems associated with SIT, such as the cost, danger to the user, and reduced competitiveness of the irradiated organism.

Preferably, the system comprises at least one positive feedback mechanism, namely at least one functional protein to be differentially expressed, via alternative splicing, and at least one promoter therefor, wherein a product of a gene to be expressed serves as a positive transcriptional control factor for the at least one promoter, and whereby the product, or the expression of the product, is controllable. Preferably, an enhancer is associated with the promoter, the gene product serving to enhance activity of the promoter via the enhancer.

The present invention allows for selective control of the expression of the first and/or second dominant lethal genes, thereby providing selective control of the expression of a lethal phenotype. It will therefore be appreciated that each of the lethal genes encodes a functional protein, such as described in WO2005/012534.

Each of the lethal genes has a lethal effect which is conditional. An example of suitable conditions includes temperature, so that the lethal is expressed at one temperature but not, or to a lesser degree, at another temperature. Another example of a suitable condition is the presence or absence of a substance, whereby the lethal is expressed in either the presence or absence of the substance, but not both. It is preferred that the effect of the lethal gene is conditional and is not expressed under permissive conditions requiring the presence of a substance which is absent from the natural environment of the organism, such that the lethal effect of the lethal system occurs in the natural environment of the organism.

Each lethal genetic system may act on specific cells or tissues or impose its effect on the whole organism. Systems that are not strictly lethal but impose a substantial fitness cost are also envisioned, for example leading to blindness, flightlessness (for organisms that could normally fly), or sterility. Systems that interfere with sex determination are also envisioned, for example transforming or tending to transform all or part of an organism from one sexual type to another.

In some embodiments, the product of at least one of the lethal genes is preferably an apoptosis-inducing factor, such as the AIF protein described for instance in Candé et al. (2002) *J. Cell Science* 115:4727-4734) or homologues thereof. AIF homologues are found in mammals and even in invertebrates, including insects, nematodes, fungi, and plants, meaning that the AIF gene has been conserved throughout the eukaryotic kingdom. In other embodiments, the product of at least one of the lethal genes is Hid, the protein product of the head involution defective gene of *Drosophila melanogaster*, or Reaper (Rpr), the product of the reaper gene of *Drosophila*, or mutants thereof. Use of Hid was described by Heinrich and Scott (2000) *Proc. Natl Acad. Sci USA* 97:8229-8232). Use of a mutant derivative, HidAla5 was described by Horn and Wimmer (2003) *Nature Biotechnology* 21:64-70). Use of a mutant derivative of Rpr, RprKR, is described herein (see also White et al. (1996); *Science* 271(5250):805-807; Wing et al. (2001) *Mech. Dev.* 102(1-2):193-203; and Olson et al. (2003) *J. Biol. Chem.* 278(45):44758-44768. Both Rpr and Hid are pro-apoptotic proteins, thought to bind to IAP1. IAP1 is a well-conserved anti-apoptotic protein. Hid and Rpr are therefore expected to work across a wide phylogenetic range (Huang et al. (2002); Vernooy et al. (2000) *J. Cell Biol.* 150(2):F69-76) even though their own sequence is not well conserved.

Nipp1Dm, the *Drosophila* homologue of mammalian Nipp1 (Parker et al. (2002) *Biochemical Journal* 368:789-797; Bennett et al., (2003) *Genetics* 164:235-245) are utilized in some embodiments. Nipp1Dm is another example of a protein with lethal effect if expressed at a suitable level, as would be understood by the skilled person. Indeed, many other examples of proteins with a lethal effect will be known to the person skilled in the art.

In other embodiments, the lethal genes is tTA or a tTAV gene variant, where tTA denotes 'tetracycline repressible Trans-Activator' and V denotes 'Variant.' tTAV is an analogue of tTA, wherein the sequence of tTA has been modified to enhance the compatibility with the desired insect species. Variants of tTAV are possible, encoding the tTA protein, such that the tTAV gene products have the same functionality as the tTA gene product. Thus, the variants of the tTAV gene comprise modified nucleotide sequences as compared to the tTA nucleotide sequence and to each other, but encode proteins with the same function. Thus, tTAV gene variants can be used in the place of tTA. In some embodiments the tTA Variant proteins contain amino acid substitutions, additions or deletions. Any combination of lethal genes may be used, and, in some embodiments, the lethal genes are the same while, in other embodiments, the lethal genes are different. The improved penetrance of the lethal effect and the earlier onset of lethality is achieved by an accumulation of lethal product.

In particular embodiments, each of the first and second lethal genes is independently tTA or a tTAV gene variant. In some embodiments, each of the first and second lethal gene is independently one of tTAV (SEQ ID NO:3), tTAV2 (SEQ ID NO:27) and tTAV3 (SEQ ID NO:28). In other embodiments, the first and second lethal genes are the same. In further embodiments, one of the first and second lethal genes is tTAV (SEQ ID NO:3) and the other gene is tTAV3 (SEQ ID NO:28). However, any combination of tTAV variants may be used; thus, in some embodiments, one of the first and second genes is tTAV (SEQ ID NO:3) and the other is tTAV2 (SEQ ID NO:27), while, in a further embodiment, one of the first and second genes is tTAV2 (SEQ ID NO:27) and the other gene is tTAV3 (SEQ ID NO:28). In other embodiments, the first lethal gene is tTAV (SEQ ID NO:3) and the second lethal gene is tTAV3 (SEQ ID NO:28).

b. RNAi

The polynucleotide sequence to be expressed may comprise polynucleotides for interference RNA (RNAi). In some embodiments, where the polynucleotide sequence to be expressed comprises polynucleotides for interference RNA, it will also be understood that reference to expression in an organism refers to the interaction of the polynucleotides for interference RNA, or transcripts thereof, in the RNAi pathway, for instance by binding of Dicer (RNA Pol III-like enzyme) or formation of small interfering RNA (siRNA). Such sequences are capable of providing, for instance, one or more stretches of double-stranded RNA (dsRNA), preferably in the form of a primary transcript, which in turn is capable of processing by the Dicer. Such stretches include, for instance, stretches of single-stranded RNA that can form loops, such as those found in short-hairpin RNA (shRNA), or with longer regions that are substantially self-complementary.

Indeed, it is particularly preferred that the polynucleotides for interference RNA comprise siRNA sequences and are, therefore, preferably 20-25 nucleotides long, especially where the organism is mammalian.

In insects and nematodes especially, it is preferred to provide portion of dsRNA, for instance by hairpin formation, which can then be processed by the Dicer system. Mammalian cells generally produce an interferon response against long dsRNA sequences, so for mammalian cells it is more common to provide shorter sequences, such as siRNAs. Antisense sequences or sequences having homology to microRNAs that are naturally occurring RNA molecules targeting protein 3' UTRs are also envisaged as sequences for RNAi according to an embodiment of the present invention.

Thus, where the system is DNA, the polynucleotides for interference RNA are deoxyribonucleotides that, when transcribed into pre-RNA ribonucleotides, provide a stretch of dsRNA, as discussed above.

Polynucleotides for interference RNA are particularly preferred when said polynucleotides are positioned to minimise interference with alternative splicing. This may be achieved by distal positioning of these polynucleotides from the alternative splice control sequences, preferably 3' to the control sequences. In another preferred embodiment, substantially self-complementary regions may be separated from each other by one or more splice control sequences, such as an intron, that mediate alternative splicing. Preferably, the self-complementary regions are arranged as a series of two or more inverted repeats, each inverted repeat separated by splice control sequence, preferably an intron, as defined elsewhere.

In this configuration, different alternatively spliced transcripts may have their substantially self-complementary regions separated by different lengths of non-self-complementary sequence in the mature (post-alternative-splicing) transcript. It will be appreciated that regions that are substantially self-complementary are those that are capable of forming hairpins, for instance, as portions of the sequence are capable of base-pairing with other portions of the sequence. These two portions do not have to be exactly complementary to each other, as there can be some mismatching or toleration of stretches in each portion that do not base-pair with each other. Such stretches may not have an equivalent in the other portion, such that symmetry is lost and "bulges" form, as is known with base-pair complementation in general.

In another preferred embodiment, one or more segment of sequence substantially complementary to another section of the primary transcript is positioned, relative to the at least one splice control sequence, so that it is not included in all of the transcripts produced by alternative splicing of the primary transcript. By this method, some transcripts are produced that tend to produce dsRNA while others do not; by mediation of the alternative splicing, e.g., sex-specific mediation, stage-specific mediation, germline-specific mediation, tissue-specific mediation, and combinations thereof, dsRNA may be produced in a sex-specific, stage-specific, germline-specific or tissue-specific manner, or combinations thereof.

v. Fusion Leaders

In some embodiments it will be desirable to have the functional protein of interest free of the Splice Control Module protein sequence. In some embodiments, the Splice Control Module is operatively linked to a polypeptide-encoding polynucleotide that stimulates proteolytic cleave of a translated polypeptide ("Fusion Leader Sequences" for the polynucleotide and "Fusion Leader Polypeptide" for the encoded polypeptide). An example of such a Fusion Leader Sequence is ubiquitin encoding polynucleotide. Such a Fusion Leader Sequence may be operatively linked in frame to the 3' end of the Splice Control Module and operatively linked in frame to the protein encoding gene of interest (i.e., from 5' to 3': Splice Control Module-Fusion Leader Sequence-Gene of interest). In such a case, the Splice Control Module/Fusion Leader Polypeptide is cleaved from the protein of interest by specific proteases in the cell. Aside from ubiquitin, any other similar fusion may be made in place of ubiquitin that would have the effect of stimulating a cleavage of the N-terminal Splice Control Module.

vi. Promoters and 5'UTRs

Each lethal gene is operably linked to a promoter, wherein said promoter is capable of being activated by an activating transcription factor or trans-activating encoded by a gene also included in at least one of the gene expression systems. It is preferred that any combination of promoter and Splice Control Module is envisaged. The promoter is preferably specific to a particular protein having a short temporal or confined spatial effect, for example a cell-autonomous effect.

The promoter may be a large or complex promoter, but these often suffer the disadvantage of being poorly or patchily utilised when introduced into non-host insects. Accordingly, in some embodiments, it is preferred to employ minimal promoters. It will be appreciated that minimal promoters may be obtained directly from known sources of promoters, or derived from larger naturally occurring, or otherwise known, promoters. Suitable minimal promoters and how to obtain them will be readily apparent to those skilled in the art. For example, suitable minimal promoters include a minimal promoter derived from Hsp70, a P minimal promoter, a CMV minimal promoter, an Acf5C-based minimal promoter, a BmA3 promoter fragment, and an Adh core promoter (Bieschke, E. et al. (1998) *Mol. Gen. Genet.,* 258:571-579). Not all minimal promoters will necessarily work in all species of insect, but it is readily apparent to those skilled in the art as to how to ensure that the promoter is active. It is preferred that at least one of the operably-linked promoters present in the invention is active during early development of the host organism, and particularly preferably during embryonic stages, in order to ensure that the lethal gene is expressed during early development of the organism.

In some embodiments, the promoter can be activated by environmental conditions, for instance the presence or absence of a particular factor such as tetracycline in the tet system described herein, such that the expression of the gene of interest can be easily manipulated by the skilled person. Alternatively, a preferred example of a suitable promoter is the hsp70 heat shock promoter, allowing the user to control expression by variation of the environmental temperature to which the hosts are exposed in a lab or in the field, for instance. Another preferred example of temperature control is described in Fryxell and Miller (1995) *J. Econ. Entomol.* 88:1221-1232.

In some embodiments, the promoter is the srya embryo-specific promoter (Horn and Wimmer (2003) *Nat. Biotechnol.* 21(1):64-70) from *Drosophila melanogaster*, or its homologues, or promoters from other embryo-specific or embryo-active genes, such as that of the *Drosophila* gene slow as molasses (slam), or its homologues from other species.

Alternatively, the promoter may be specific for a broader class of proteins or a specific protein that has a long-term and/or wide system effect, such as a hormone, positive or negative growth factor, morphogen or other secreted or cell-surface signaling molecule. This would allow, for instance, a broader expression pattern so that a combination of a morphogen promoter with a stage-specific alternative splicing mechanism could result in the morphogen being expressed only once a certain life-cycle stage was reached, but the effect of the morphogen would still be felt (i.e., the morphogen can still act and have an effect) beyond that life-cycle stage. Preferred examples would be the morphogen/signaling molecules Hedgehog, Wingless/WNTs, TGFβ/BMPs, EGF and their homologues, which are well-known evolutionarily-conserved signaling molecules.

It is also envisaged that a promoter that is activated by a range of protein factors, for instance transactivators, or which has a broad systemic effect, such as a hormone or morphogen, could be used in combination with an alternative splicing mechanism to achieve a tissue and sex-specific control or sex and stage-specific control, or other combinations of stage-, tissue, germ-line- and sex-specific control.

It is also envisaged that more than one promoter, and optionally an enhancer therefor, can be used in the present system, either as alternative means for initiating transcription of the same protein or by virtue of the fact that the genetic system comprises more than one gene expression system (i.e., more than one gene and its accompanying promoter).

In some embodiments, at least one of the promoters is the minimal promoter is a heat shock promoter, such as Hsp70. In other embodiments, at least one of the promoters is the srya embryo-specific promoter (Horn and Wimmer (2003) *Nat. Biotechnol.* 21(1):64-70) from *Drosophila melanogaster*, or its homologues, or promoters from other embryo-specific or embryo-active genes, such as that of the *Drosophila* gene slow as molasses (slam), or its homologues from other species.

In some embodiments, at least one of the promoters is a minimal promoter. In some embodiments, each of the promoters is independently Baculovirus *Autographica californica* nucleopolyhedrosisvirus (AcNPV) promoter IE1, Hsp70, Hsp73 or sryα. In preferred embodiments, one of the first and second promoters is Hsp70 and the other is sryα. In one embodiment, the first promoter is Hsp70 and the second promoter is sryα. Each gene expression system further comprises a gene encoding an activating transcription factor, wherein each activating transcription factor activates the expression of a lethal gene of the transgene. Thus, each gene encoding an activating transcription factor is able to be expressed by the host organism, to produce a functional protein. In particular, each activating transcription factor is capable of activating at least one promoter, wherein the promoter is operably linked to a lethal gene. Consequently, when an activating transcription factor activates a promoter, the expression of the lethal gene operably linked to the promoter is up-regulated. Each activating transcription factor may act on either the first or the second promoter, or each activating transcription factor may act on both the first and the second promoter. It is preferred that, when more than one activating transcription factor is expressed, more than one promoter is activated. Thus, when both the first and the second activating transcription factors are expressed, both the first and the second promoters are activated. The gene products serving as activating transcription factors may act in any suitable manner. For example, the activating transcription factors may bind to an enhancer located in proximity to the at least one promoter, thereby serving to enhance polymerase binding at the promoter. Other mechanisms may be employed, such as repressor countering mechanisms, such as the blocking of an inhibitor of transcription or translation. Transcription inhibitors may be blocked, for example, by the use of hairpin RNA's or ribozymes to block translation of the mRNA encoding the inhibitor, or the product may bind the inhibitor directly, thereby preventing inhibition of transcription or translation.

vii. Repressible Elements

Preferably, the polynucleotide expression system is a recombinant dominant lethal genetic system, the lethal effect of which is conditional. Suitable conditions include temperature, so that the system is expressed at one temperature but not, or to a lesser degree, at another temperature, for example. The lethal genetic system may act on specific cells or tissues or impose its effect on the whole organism. It will be understood that all such systems and consequences are encompassed by the term lethal as used herein. Similarly, "killing", and similar terms refer to the effective expression of the lethal system and thereby the imposition of a deleterious or sex-distorting phenotype, for example death.

More preferably, the polynucleotide expression system is a recombinant dominant lethal genetic system, the lethal effect of which is conditional and is not expressed under permissive conditions requiring the presence of a substance which is absent from the natural environment of the organism, such that the lethal effect of the lethal system occurs in the natural environment of the organism.

In some embodiments, the coding sequences encode a lethal linked to a system such as the tet system described in WO 01/39599 and/or WO2005/012534.

Indeed it is preferred that the expression of said lethal gene is under the control of a repressible transactivator protein. It is also preferred that the gene whose expression is regulated by alternative splicing encode a transactivator protein such as tTA. This is not incompatible with the regulated protein being a lethal. Indeed, it is particularly preferred that it is both. In this regard, we particularly prefer that the system includes a positive feedback system as taught in WO2005/012534.

Preferably, the lethal effect of the dominant lethal system is conditionally suppressible.

Thus, in some embodiments wherein one or more of the dominant, lethal genes is tTA or a tTAV gene variant, an enhancer is a tetO element, comprising one or more tetO operator units. Upstream of a promoter, in either orientation, tetO is capable of enhancing levels of transcription from a promoter in close proximity thereto, when bound by the product of the tTA gene or a tTAV gene variant. In some embodiments, each enhancer is independently one of tetOx1, tetOx2, tetOx3, tetOx4, tetOx5, tetOx6, tetOx7, tetOx8, tetOx9, tetOx10, tetOx11, tetOx12, tetOx13, tetOx14, tetOx15, tetOx16, tetOx17, tetOx18, tetOx19, tetOx20 and tetOx21. In some embodiments, each enhancer is independently one of tetOx1, tetOx14 and tetOx21. In embodiments comprising more than one enhancer, the first enhancer is the same as or different from the second enhancer. An example of the TetOx7 element is shown in SEQ ID NO:14.

viii. Other Elements

In some embodiments, the system comprises other upstream, 5' factors and/or downstream 3' factors for controlling expression. Examples include enhancers such as the fat-body enhancers from the *Drosophila* yolk protein genes, and the homology region (hr) enhancers from baculoviruses, for example AcNPV Hr5. It will also be appreciated that the RNA products will include suitable 5' and 3' UTRs, for instance.

It will be understood that reference is made to start and stop codons between which the polynucleotide sequence to be expressed in an organism is defined, but that this does not exclude positioning of the at least one splice control sequence, elements thereof, or other sequences, such as introns, in this region. In fact, it will be apparent form the present description that the splice control sequence, can, in some embodiments, be positioned in this region.

Furthermore, the splice control sequence, for instance, can overlap with the start codon at least, in the sense that the G of the ATG can be, in some embodiments, be the initial 5' G of the splice control sequence. Thus, the term "between" can be thought of as referring to from the beginning (3' to the initial nucleotide, i.e., A) of the start codon, preferably 3' to the second nucleotide of the start codon (i.e., T), up to the 5' side of the first nucleotide of the stop codon. Alternatively, as will be apparent by a simple reading of a polynucleotide sequence, the stop codon may also be included.

ix. Vectors in General and Incorporate Elements Permitting Replication

In embodiments of the invention, the system is or comprises a plasmid. As mentioned above, this can be either DNA, RNA or a mixture of both. If the system comprises RNA, then it may be preferable to reverse-translate the RNA into DNA by means of a Reverse Transcriptase. If reverse transcription is required, then the system may also comprise a coding sequence for the RT protein and a suitable promoter therefor. Alternatively, the RTase and promoter therefore may be provided on a separate system, such as a virus. In this case, the system would only be activated following infection with that virus. The need to include suitable cis-acting sequences for the reverse transcriptase or RNA-dependent RNA polymerase would be apparent to the person skilled in the art.

However, it is particularly preferred that the system is predominantly DNA and more preferably consists only of DNA, at least with respect to the sequences to be expressed in the organism.

B. Introduction of Constructs into Organisms

Methods of introduction or transformation of the gene system constructs and induction of expression are well known in the art with respect to the relevant organism. It will be appreciated that the system or construct is preferably administered as a plasmid, but generally tested after integrating into the genome. Administration can be by known methods in the art, such as parenterally, intra-venous intra-muscularly, orally, transdermally, delivered across a mucous membrane, and so forth. Injection into embryos is particularly preferred. The plasmid may be linearised before or during administration, and not all of the plasmid may be integrated into the genome. Where only part of the plasmid is integrated into the genome, it is preferred that this part include the at least one splice control module capable of mediating alternative splicing.

Plasmid vectors may be introduced into the desired host cells by methods known in the art, such as, for example by transfection, electroporation, microinjection, transduction, cell fusion, DEAE dextran, calcium phosphate precipitation, lipofection (lysosome fusion), use of a gene gun, or a DNA vector transporter (see, e.g., Wu et al., (1992) *J. Biol. Chem.* 267:963; Wu et al. (1988) *J. Biol. Chem.* 263:14621; and Canadian Patent Application No. 2,012,311 to Hartmut et al.). The plasmid vector may be integrated into the host chromosome by any means known. Well-known methods of locus-specific insertion may be used, including, homologous recombination and recombinase-mediated genome insertion. In another embodiment, locus-specific insertion may be carried out by recombinase-site specific gene insertion. In one example piggyBac sequences may be incorporated into the vector to drive insertion of the vector into the host cell chromosome. Other technologies such as CRISPRs, TALENs, AttP/AttB recombination may also be employed.

C. Genetically Engineered Insects

Suitable organisms under which the present system can be used include non-human mammals such as mice, rats and farm animals. Also preferred are fish, such as salmon and trout. Plants are also preferred, but it is particularly preferred that the host organism is an insect, preferably a Dipteran or tephritid.

The vectors of the invention may be used to create transgenic insects in a wide variety of genera and species. The insects that may be transformed with a vector of the invention include, but are not limited to those in the Order Diptera, especially higher Diptera, such as, for example, a tephritid fruit fly, such as Medfly (*Ceratitis capitata*), Mexfly (*Anastrepha ludens*), Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha obliqua*). It is also particularly preferred that the host organism is a mosquito, preferably from the genera *Stegomyia, Aedes, Anopheles* or *Culex*. Particularly preferred are *Stegomyia aegyptae*, also known as *Aedes aegypti, Stegomyia albopicta* (also known as *Aedes albopictus*), *Anopheles stephensi, Anopheles albimanus* and *Anopheles gambiae.*

Within Diptera, another group which may be modified using a vector of the invention is Calliphoridae, such as, for example the New world screwworm (*Cochliomyia hominivorax*), and Old world screwworm (*Chrysomya bezziana*). Other dipteran species include Australian sheep blowfly (*Lucilia cuprina*), *Agromyza frontella* (alfalfa blotch leafminer), *Agromyza* spp. (leaf miner flies), *Chrysops* spp. (deer flies), *Contarinia* spp. (Gall midges), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (grass fly),

*Pegomyia betae* (beet leafminer), *Phorbia* spp., *Psila rosae* (carrot rust fly), *Rhagoletis pomonella* (apple maggot), *Sitodiplosis mosellana* (orange wheat blossom midge), *Stomoxys calcitrans* (stable fly), *Tabanus* spp. (horse flies) and *Tipula* spp. (crane flies).

Lepidoptera may likewise be modified using a vector of the invention. Examples of these include, but are not limited to *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrine* (orange torrid), *Autograph gamma, Bongos crunodes*, Bourbon cinnabar (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Darna diducta, Diaphania* spp. (stem borers), *Diatraea* spp. (stalk borers), *Diatraea saccharalis* (sugarcane borer), *Diatraca graniosella* (southwester corn borer), *Earias* spp. (bollworms), *Earias insulata* (Egyptian bollworm), *Earias vitella* (rough northern bollworm), *Ecdytopopha aurantianum, Elasmopatpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis ccrasana* (common currant *tortrix*), *Pandemis heparana* (brown apple *tortrix*), *Papilio demodocus, Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leaf miners), *Pieris rapae* (imported cabbageworm), *Plathypena scabra, Plodia interpunctella* (Indian meal moth), *Polychrosis viteana* (grape berry moth), *Prays endocarpa, Prays oleae* (olive moth), *Pseudaletia* spp. (noctuid moths), *Pseudaletia umpunctata* (armyworm), *Pseudoplusia includens* (soybean looper), *Rachiplusia nu, Scirpophaga incertulas, Sesamia* spp. (stemborers), *Sesamia infercns* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera littoralis* (cotton leafworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), *Zeuzera pyrina* (leopard moth), *Cydia pomonella* (codling moth), *Bombyx mori* (silk worm), *Pectinophora gossypiella* (pink bollworm), *Plutella xylostella* (diamondback moth), *Lymantria dispar* (Gypsy moth), *Amyelois transitella* (Navel Orange Worm), *Anarsia lineatella* (Peach Twig Borer), *Tryporyza incertulas* (rice stem borer), and *Heliothinae* spp. (noctuid moths).

Among Coleoptera, examples include, but are not limited to *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass *Ataenius*), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp, *Cerotoma* spp. (chrysomeids), *Cerotoma trifurcata* (bean leaf beetle), *Ceutorhynchus* spp. (weevils), *Ceutorhynchus assimilis* (cabbage secdpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leafcutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius* pales (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricome* (cigarette beetle), *Leptinotarsa decemlineata* (Colorado potato beetle), *Liogenys futscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha mclolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (Eurpoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle) and *Zabrus tenebioides.*

Further, Hemiptera may also be modified with a vector of the invention. Non-limiting examples of Hemiptera that may be so modified, include: *Acrosternum hilare* (green stink bug), *Blissus leucopterus* (chinch bug), *Calocoris norvegicus* (potato mind), *Cimex hemipterus* (tropical bed bug), *Cimex lectularius* (bed bug), *Dichelops melacanthus* (Dallas), *Dagbertus fasciatus, Dichelops furcatus, Dysdercus suturellus* (cotton stainer), *Edessa meditabunda, Eurygaster maura* (cereal bug), *Euschistus heron, Euschistus servus* (brown stink bug), *Helopeltis antonii, Helopeltis theivora* (tea blight plantbug), *Lagynotomus* spp. (stink bugs), *Leptocorisa oratorius, Leptocorisa varicomis, Lygus* spp. (plant bugs), *Lygus hesperus* (western tarnished plant bug), *Maconellicoccus hirsutus, Neurocolpus longirostris, Nezara viridula* (southern green stink bug), *Paratrioza cockerelli, Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea, Triatoma* spp. (bloodsucking conenose bugs/kissing bugs) and glassy-winged sharpshooters (*Homalodisca vitripennis*).

Further other insects which may be modified with a vector of the invention. *Homoptera*, such as *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis fabae* (aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape *phylloxera*), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum* maida (corn leaf aphid), *Rhapalosiphum padi* (oat bird-cherry aphid), *Saissetia* spp. (scales), *Saissctia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale) and *Zulia entreriana.*

In some embodiments, the insect is not a Drosophilid such as *Drosophila melanogaster*. Thus, in some embodiments, expression in Drosophilids, is excluded. In other embodiments, the splice control sequence is not derived from the tra intron of a Drosophilid, especially *Drosophila melanogaster.*

Species of mosquitoes that may be modified by the constructs of the invention include, but are not limited to mosquitoes of a genera selected from the group consisting of *Anopheles* sp., *Culex* sp., *Aedes* sp., and *Toxorhynchites* sp. In particular embodiments, the mosquitoes are selected from *Anopheles fluviatilis, Culex quinquefasciatus, Anopheles strode, Anopheles pseudopuncti, Aedes aegypti, Anopheles shannoni, Anopheles apicimaculata, Aedes rubrithorax, Anopheles argyritarsis, Anopheles neomaculipal, Anopheles fluminensis, Aedes alboannulatus, Aedes albopictus, Anopheles punctimaculata, Anopheles anomolophyllus, Anopheles vestitipennis, Anopheles albimanus, Toxorhynchites brevipalpie, Toxorhynchites splendens, Toxorhynchites ambionensis, Toxorhynchites rutilus*, and *Toxorhynchites moctezumai*. In specific embodiments, the mosquitoes are selected from the group consisting of *Aedes aegypti, Aedes rubrithorax, Aedes albopictus*, and *Aedes alboannulatus.*

D. Specific Embodiments

In a specific embodiment, a dsx splice control module is used for sex-specific expression in an insect. In this embodiment, the dsx splice control module is derived from *Aedes aegypti* and incorporates both introns and exons from the *Aedes aegypti* dsx (Aeadsx). In a preferred embodiment, the Aeadsx splice control module comprises, Exon 4, Intron 5, Exon 5a, Intron 5, Exon 5b, Intron 6 and Exon 6 of the dsx. In a particularly preferred embodiment, portions of the Introns and Exons are used (preserving the splice donor and splice acceptor sites of each) but that are truncated to reduce the size of the overall splice control module.

In some embodiments, the entire sequence of Exon 4 (135 bp) is used, but smaller fragments may be used provided the sequence retains the splice donor site. The Aeadsx Exon 4 is shown as SEQ ID NO:13.

In some embodiments, the entire sequence of Intron 4 is used, but smaller fragments may be used provided the sequence retains the splice donor site. The Aeadsx Intron 4 is large, so it is advantageous to truncate the intron by removing a portion of the middle of the intron such that nucleotides including the splice donor at the 5' end of the intron are preserved and linked to a 3' portion of the intron that contains the splice acceptor site. An example of the 5' end of Intron 4 is shown as SEQ ID NO:12, and an example of the 3' portion of Intron 4 is shown as SEQ ID NO:11. These are joined to provide a truncated, functional Intron 4.

In some embodiments, the entire sequence of Exon 5a (a female-specific exon) is used, but smaller fragments may be used provided the sequence retains the splice donor site. The Aeadsx Exon 5a is shown as SEQ ID NO:6.

In some embodiments, the entire sequence of Intron 5 (209 bp) is used, but smaller fragments may be used provided the sequence retains the splice donor site. The Aeadsx Intron 5 is shown as SEQ ID NO:10.

In some embodiments, a protein encoding portion of Exon 5b (a female-specific exon) is used. In the native exon, only 56 nucleotides are protein encoding. In some embodiments, the Exon 5b is engineered to open the reading frame so that the entire sequence is protein encoding. This may be done by any manipulation that puts the sequence in frame and retains as much native primary amino acid sequence as will be functional. In one such manipulation (relative to the native *Aedes aegypti* dsx gene (shown as SEQ ID NO:7) a total of 5 nucleotide insertions are made, a single nucleotide is deleted and a single nucleotide change was made to obtain a protein encoding Exon 5b.

In some embodiments, the entire sequence of Intron 6 is used, but smaller fragments may be used provided the sequence retains the splice donor site. The Aeadsx Intron 6 is large, so it is advantageous to truncate the intron by removing a portion of the middle of the intron such that nucleotides including the splice donor at the 5' end of the intron are preserved and linked to a 3' portion of the intron that contains the splice acceptor site. An example of the 5' end of Intron 6 is shown as SEQ ID NO:9, and an example of the 3' portion of Intron 6 is shown as SEQ ID NO:8. These are joined to provide a truncated, functional Intron 6.

In some embodiments, the entire sequence of Exon 6 (a shared exon) is used, but smaller fragments may be used provided the sequence retains the splice acceptor site. In other embodiments, only a 5' portion of the Exon 6 is used. An example of a 5' portion of Exon 6 that may be used is shown as SEQ ID NO:5.

In a specific example, the Splice Control Module is an Aeadsx comprising Exon 4 (SEQ ID NO:13), a truncated Intron 4 (composed of SEQ ID NO:12 and SEQ ID NO:13), Exon 5a (SEQ ID NO:6), Intron 5 (SEQ ID NO:10), a modified Exon 5b (SEQ ID NO:7), a truncated Intron 6 (composed of SEQ ID NO:9 and SEQ ID NO:8) and Exon 6 (SEQ ID NO:5).

As with all nucleotide sequences discussed herein, it is preferred that a certain degree of sequence homology is envisaged, unless otherwise apparent. Thus, it is preferred that the elements of the Aeadsx splice control module has at least 80%, 85%, 90%, 95%, 99% or 99.9% sequence homology with the reference sequences SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13. A suitable algorithm such as BLAST may be used to ascertain sequence homology. If large amounts of sequence are deleted compared to the wild type, then the sequence comparison may be over the full length of the wild type or over aligned sequences of similar homology.

In a specific embodiment of the invention, the control factor is the tTA gene product or an analogue thereof, and wherein one or more tetO operator units is operably linked with the promoter and is the enhancer, tTA or its analogue serving to enhance activity of the promoter via tetO. It is preferred that functional protein encodes the tTAV or tTAV product and preferably, the promoter is substantially inactive in the absence of the positive transcriptional control factor. Suitable, preferably minimal, promoters for this system can be selected from: hsp70, a P minimal promoter, a CMV minimal promoter, an Act5C-based minimal promoter, a BmA3 promoter fragment, a promoter fragment from hunchback, an Adh core promoter, and an Act5C minimal promoter, or combinations thereof. In some embodiments, the functional protein itself a transcriptional transactivator, such as the tTAV system.

E. Methods of Biological Control

In a further aspect, there is also provided a method of population control of an organism in a natural environment therefor, comprising:

i) breeding a stock of the organism, the organism carrying a gene expression system comprising a system according to the present invention which is a dominant lethal genetic system, ii) distributing the said stock animals into the environment at a locus for population control; and iii) achieving population control through early stage lethality by expression of the lethal system in offspring that result from interbreeding of the said stock individuals with individuals of the opposite sex of the wild population.

Preferably, the early stage lethality is embryonic or before sexual maturity, preferably early in development, most preferably in the early larval or embryonic life stages.

Preferably, the lethal effect of the lethal system is conditional and occurs in the said natural environment via the expression of a lethal gene, the expression of said lethal gene being under the control of a repressible transactivator protein, the said breeding being under permissive conditions in the presence of a substance, the substance being absent from the said natural environment and able to repress said transactivator.

Preferably, the lethal effect is expressed in the embryos of said offspring. Preferably, the organism is an invertebrate multicellular animal or is as discussed elsewhere.

Also provided is a method of biological control, comprising:

i) breeding a stock of males and female organisms transformed with the expression system according to the present invention under permissive conditions, allowing the survival of males and females, to give a dual sex biological control agent;

ii) optionally before the next step imposing or permitting restrictive conditions to cause death of individuals of one sex and thereby providing a single sex biological control agent comprising individuals of the other sex carrying the conditional lethal genetic system;

iii) releasing the dual sex or single sex biological control agent into the environment at a locus for biological control; and iv) achieving biological control through expression of the genetic system in offspring resulting from interbreeding of the individuals of the biological control agent with individuals of the opposite sex of the wild population.

Preferably, there is sex-separation prior to organism distribution by expression of a sex specific lethal genetic system.

Preferably, the lethal effect results in killing of greater than 90% of the target class of the progeny of matings between released organisms and the wild population.

Also provided is a method of sex separation comprising:

i) breeding a stock of male and female organisms transformed with the gene expression system under permissive or restrictive conditions, allowing the survival of males and females; and ii) removing the permissive or restrictive conditions to induce the lethal effect of the lethal gene in one sex and not the other by sex-specific alternative splicing of the lethal gene.

Preferably, the lethal effect results in killing of greater than 90% of the target class of the progeny of matings between released organisms and the wild population.

Also provided is a method to selectively eliminate females from a population. The equivalent for males is also envisaged.

The invention will now be described by reference to the following examples which are meant to be illustrative of embodiments of the invention and are not to be construed as limiting the invention.

EXAMPLES

Example 1

Genetically engineered *Aedes aegypti* strains were generated by insertion of the recombinant DNA (rDNA) construct (FIG. 1) (hereinafter "DSX-tTAV-Red") into the *Ae. aegypti* genome. This DNA is comprised of two gene cassettes contained between the 5' and 3' fragments of the *Trichoplusia ni* piggyBac transformation system used to insert them into the insect genome. The gene cassettes are as follows:

1. The Hr5IE1 enhancer and promotor, which derives from *Autographa californica* nuclear polyhedrosis virus (AcNPV), drives expression of the DsRed2 protein. This protein is a synthetic derivative of a red fluorescent protein sourced from Clontech.
2. A minimal promoter from the *Drosophila melanogaster* heat shock protein 70 (Dmhsp70 minipro) gene, downstream of a tetracycline responsive operator (TetO x7), drives expression of the synthetic tetracycline-repressive transcriptional activator protein (tTAV) (Gossen and Bujard 1992) *Proc. Natl. Acad. Sci. USA* 89(12): 5547-5551; Gong et al., (2005) *Nat. Biotech.* 23:453-456). Expression of tTAV protein is rendered female-specific by the inclusion of portions of the *Ae. aegypti* doublesex gene (Aeadsx). As the Aeadsx sequences will lead to additional amino acids included on the N-terminus of the tTAV protein, the ubiquitin protein (Ubi) is placed between the Aeadsx and tTAV sequences. Ubiquitin is cleaved through normal cellular processes, and so the Aeadsx-derived and Ubi amino acids are removed, leaving tTAV (Bachmair et al., (1986) *Science* 234(4773):179-186; Varshaysky, A. (2005) *Meth. Enzymol.* 399:777-799).

Together these gene cassettes deliver a strain of *Ae. aegypti* that, when reared in the presence of tetracycline, development occurs normally in both sexes, but when reared in the absence of tetracycline females do not survive to adulthood and a male-only cohort is produced. Additionally, each insect is marked with the fluorescent DsRed2 protein.

A. Preparation of the Aeadsx Splice Control Module

The Aeadsx splice control module was engineered from endogenous components of the *Ae. aegypti* doublesex gene that normally give rise to the sex-specific alternative splicing of the gene. These are exons 4, 5a, 5b and 6; and introns 4, 5 and 6. The sequences of some of these components (introns 4, intron 6 and exon 5b) were manipulated before being integrated in the sex-specific module.

Introns 4 and 6 are too large to be included full length in pDSX-TTAV-RED, natively 14.526 kb and 10.393 kb, respectively. The 5' and 3' ends of each intron have been retained, but the central intronic sections removed without losing functionality. The final sizes in the Aeadsx splice control module were 1.750 kb for intron 4, and 1.446 kb for intron 6.

Exon 5b, that partially encodes in the native protein, was modified to allow an open reading frame to span the entire exon so that it would be in-frame with the Leading Peptide (e.g., ubiquitin) encoding sequence which was likewise in frame with a gene of interest. This was accomplished by making one base pair substitution, deleting 1 base pair and inserting 5 base pairs. This manipulation made the reading frame in the F2 transcript protein coding from the engineered start codon (ATG) immediately upstream of exon 4, through exons 4, 5b and 6, and into Leading Peptide/gene of interest. The M (male) splice form includes exon 6 which when spliced to exon 4 causes a frame shift which results in the inclusion of a stop codon prior to the gene of interest coding sequence.

a. Aeadsx Control of tTAV

To generate DSX-tTAV-Red, the Aeadsx splice control module described above was engineered to produce a synthetic, repressible transcriptional activator protein, tTAV. It was engineered to be under the control of a tetracycline responsive composite promoter, engineered by joining 7 repeats of TetO operator sequence from *E. coli* (TetO x7) with a minimal promoter from the heat shock protein 70 gene of *Drosophila melanogaster* (DmHsp70 minipro) (Gossen & Bujard, 1992; Gong et al., 2005). The tTAV then acts in a positive feedback loop as the binding of tTAV to TetO drives further expression of that same protein. Without wishing to be bound by any particular theory of operation, it is believed that high level expression is deleterious to cells, likely due to transcriptional "squelching" (Gill and Ptashe, 1988). This feedback loop can be broken by the administration of tetracycline as this molecule is bound by tTAV and thereby rendered unable to bind the operator, TetO.

The feedback loop operates specifically in females due to the addition Aeadsx) splice control module wherein the mRNAs produced in males and females are different due to sex-specific splicing. This, in turn means that the tTAV protein is only correctly encoded by an mRNA produced in females. Only the F2 splice form correctly encodes the tTAV protein.

In addition to the Aeadsx module, the self-limiting gene encodes the *D. melanogaster* Ubiquitin (Ubi) protein as an N-terminal fusion of the tTAV protein. In the insect, Ubi is predicted to be precisely processed post translation of the protein in order to remove any parts of the polypeptide encoded by the Aeadsx splice control module to leave just the tTAV protein without any further polypeptide sequences at the N-terminus of the protein (Bachmair et al., (1986) *Science* 234(4773):179-186; Varshaysky, A. (2005) *Meth. Enzymol.* 399:777-799). Ubiquitin is encoded as a polypeptide in eukaryotes including insects, and relies on precise proteolytic cleavage at the C-terminal residue of the ubiquitin 76-mer sequence to generate free ubiquitin. By fusing alternative sequences to the C-terminus of Ubiquitin, it is possible to take advantage of this cleavage activity to cleave a protein of interest from an N-terminal tag.

B. Preparation of the DsRed2 Cassette

DSX-TTAV-RED contains a Hr5IE1 enhancer and promotor that drives expression of a DsRed2 protein. The fluorescent phenotype is clearly visible in all larval, pupal and adult life stages. This provides an enhancement of the phenotype of self-limiting strain, OX513A, that utilises the Actin5C promoter to produce DsRed2 markings in larval and pupal stages.

Figure 2:
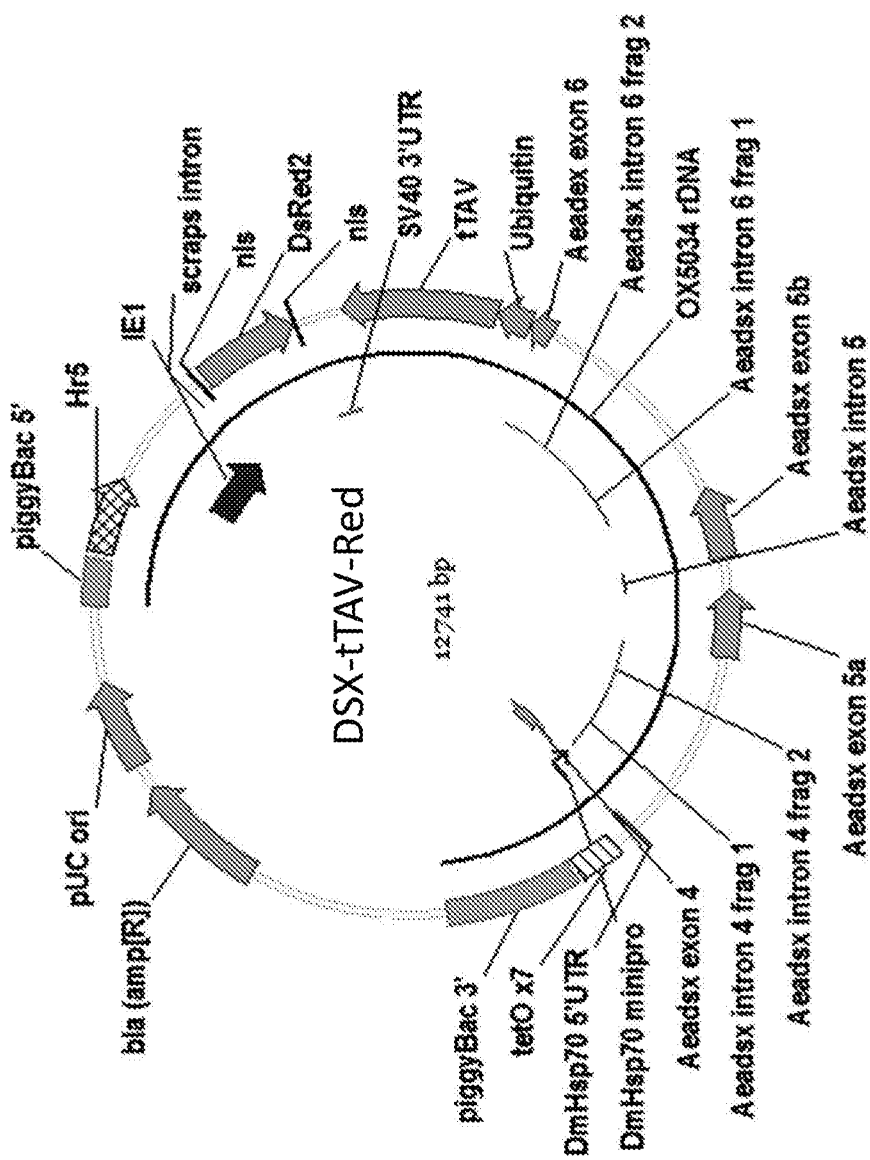
FIG. 2 shows a plasmid map for DSX-tTAV-Red. The rDNA is shown by the thin black line running along the inside of the plasmid schematic. Components not designated as rDNA are not incorporated into the insect genome. A list and description of rDNA components are provided in Table 1.

Nuclear localization signal peptide encoding sequences (nls1 and nls2) were engineered on the N-terminal and C-terminal encoding portions of DsRed2 as shown in FIG. 2 based on SV40 NLS sequence (Kalderon et al. (1984) *Cell* 39(3):499-509). In this example, the nls sequences are shown in SEQ ID NO:20 (nls1) and SEQ ID NO:21 (nls2).

C. Preparation of the Vector Plasmid

The vector plasmid shown in FIG. 2 is based on cloning vector pKC26-FB2 (Genbank #HQ998855). The plasmid backbone contains the pUC origin of replication and the beta-lactamase ampicillin resistance gene for use in molecular cloning procedures. This plasmid section is not included in the rDNA or incorporated into the insect genome. The vector plasmid also contains the complete rDNA that is incorporated into the insect and includes; the 3' and 5' piggyBac element ends derived from *Trichoplusia ni*, the DsRed2 Cassette containing the gene for the DsRed2 red fluorescence marker protein from Dictyosoma, a synthetic DNA sequence for the tetracycline repressible transcriptional activator tTAV based on a fusion of sequences Gossan and Bujard (1992) *Proc. Natl. Acad. Sci. USA* 89(12):5547-5551, and a modified Aeadsx splice control module derived from *Ae. aegypti* (as described above and generally throughout the Specification). A table of the components shown in FIG. 2 is shown in Table 1 where the nature of each component is also described. The plasmid was prepared using routine DNA cloning procedures.

TABLE 1

| Component | Source | Location (bp) in DSX-tTAV-RED | Size (bp) | Function | SEQ ID NO: |
|---|---|---|---|---|---|
| piggyBac 5' | Synthetic (Derived from *Trichoplusia ni*) | 1-309 | 309 | Facilitates germline transformation with rDNA only in the presence of the piggyBac transposase. (Carry et al. (1989) *Virol.* 172(1): 156-169, Fraser et al. (1995) *Virol.* 211: 397-407, Fraser et al. (1996) *Insect Mol. Biol.* 5: 141-151). | 16 |
| Hr5 | Baculovirus nucleopolyhedrovirus (AcNPV) | 355-863 | 509 | Transcriptional enhancer to stimulate expression from the IE1 promoter (Rodems and Friesen (1993) *J. Virol.* 69(10): 5776-5785) | 17 |
| IE1 | Baculovirus *Autographa californica* nucleopolyhedrovirus (AcNPV) | 924-1553 | 630 | Promoter to drive the expression of DsRed2 protein (Guarino and Dong (1991) *J. Virol.* 65(7): 3676-3680) | 18 |
| Scraps intron | *Drosophila melanogaster* | 1569-1631 | 63 | An intron cloned upstream of the DsRed2 coding sequence to facilitate transcription of mRNA (Field et al. (2005) *Development* 132(12): 2849-2860 | 19 |
| nls | Synthetic sequence | 1668-1709 and 2397-2429 | 42 and 33 | nls: Nuclear Localisation Signal. Synthetic DNA sequences that encode protein domains at the N- and C-terminal ends of DsRed2 for import into the cell nucleus by importins (Lange (2007) *J. Biol. Chem.* 282: 5101-5105 | 20 |
| DsRed2 | Synthetic DNA encoding a variant of red fluorescent protein (Clontech) | 1716-2390 | 675 | Marker gene - a red fluorescent protein (Lukyanov et al. (2000) *J. Biol. Chem.* 2755: 25879-25882; Matz et al. (1999)*Nat. Biotechnol.* 17(10): 969-973) | 4 |
| SV40 3'UTR | Synthetic non-coding fragment based on Simian virus (SV40) isolated from pDsRed2-N1 (Clontech plasmid) | 2455-2682 | 228 | A 3' untranslated sequence. It contains the transcription termination and polyadenylation signals (Clontech Laboratories Inc. 2012 available on the Clontech Website; Brand and Perrimon (1993) *Development* 118: 401-415) | 22 |
| tTAV | Synthetic fusion tetracycline transactivator protein. Optimised for expression in insects. | 2715-3725 | 1011 | Tetracycline repressible transcription factor (Gossen and Bujard (1992) *Proc. Natl. Acad. Sci. USA* 89(12): 5547-5551; Gong et al. (2005) *Nat. Biotech.* 23: 453-456). | 3 |
| Ubiquitin | *Drosophila melanogaster* | 3726-3950 | 225 | Stimulates cleavage of tTAV protein from the Aeadsx-Ubi that is N-terminally fused (Varshavsky, (2005)*Meth. Enzymol.* 399777-799) | 2 |
| Aeadsx splice control module | *Aedes aegypti* | 3951-4101 | 151 | Aeadsx exon 6: 5'end of the native Aeadsx exon 6. This is a shared exon. | 5 |
| | | 4100-4987 | 886 | Aeadsx intron 6 frag2: The 3'end of intron 6. This fragment is used with Aeadsx intron 6 frag1 to build the truncated version of intron 6. | 8 |
| | | 4990-5547 | 560 | Aeadsx intron 6 frag1: The 5'end of intron 6. This fragment is used with Aeadsx intron 6 frag2 to build the truncated version of intron 6. | 9 |
| | | 5548-6016 | 469 | Aeadsx exon 5b: An engineered version of the native exon 5b. To open the reading frame throughout the whole exon (only 110 nt are coding in the native exon), a total of 4 insertions, 1 nt deletion and 1 nt change were introduced to this exon. This is a female-specific exon. | 7 |
| | | 6017-6225 | 209 | Aeadsx intron 5: The whole sequence of the native intron 5. | 10 |
| | | 6226-6683 | 458 | Aeadsx exon 5a: The whole sequence of the native exon 5a. This is a female-specific exon. | 6 |
| | | 6684-7267 | 584 | Aeadsx intron 4 frag2: The 3'end of intron 4. This fragment is used with Aeadsx intron 4 frag1 to build the truncated version of intron 4. | 11 |

TABLE 1-continued

| Component | Source | Location (bp) in DSX-tTAV-RED | Size (bp) | Function | SEQ ID NO: |
|---|---|---|---|---|---|
| | | 7268-7858 | 591 | Aeadsx intron 4 frag1: The 5'end of intron 4. This fragment is used with Aeadsx intron 4 frag2 to build the truncated version of intron 4. | 12 |
| | | 7859-7993 | 135 | Aeadsx exon 4: The whole sequence of the native Aeadsx exon 4. This is a shared exon. | 13 |
| DmHsp70 minipro | *Drosophila melanogaster* | 8002-8131 | 130 | The minimal promoter (43 bp) and the 5'UTR (87 bp) from the hsp70 gene promotes expression when the tTAV is bound to the neighbouring TetO operator. | 23 |
| TetO x7 | Synthetic DNA contains 7 repeats of Tn10 tet-operon | 8137-8432 | 296 | Binds tTAV in the absence of tetracycline, facilitating expression by the neighbouring mini-promoter (Gossen and Bujard 1992). | 14 |
| piggyBac 3' | Synthetic (Derived from *Trichoplusia ni*) | 8461-9325 | 865 | Facilitates germline transformation with rDNA only in the presence of the piggyBac transposase. | 15 |

D. Strain Generation

For insertion of the cassettes into *Aedes aegypti, Aedes aegypti* of the Latin wild type strain (originating from Mexico) were reared under standard insectary conditions [26° C.±2° C.], 70% [±10%] relative humidity and 12 h:12 h light:dark cycle. Mosquito embryos were transformed by standard micro-injection methods (Jasinskiene et al., (1998) *Proc. Natl. ACad. Sci. USA* 95:7520-7525; Morris, A. C. (1997) "Microinjection of mosquito embryos" In: Crampton, J. M., Beard, C. B., Louis, C. (Eds.), Molecular Biology of Insect Disease Vectors: A Methods Manual. Chapman & Hall, 2-6 Boundary Row, London SE1 8HN, UK, pp. 423-429), injecting a combination of plasmid DNA (concentration of 300 ng/μl of DSX-tTAV-Red, the plasmid depicted in FIG. 2), and piggyBac mRNA (at a concentration of 500 ng/μl) as the source of transposase. The plasmid DNA and the transposase mRNA were reconstituted in an injection buffer (5 mM KCl, 0.1 mM $NaH_2PO_4$, pH 6.8) made using standard laboratory grade reagents (Handler and James, 1998).

E. Strain Selection

Selection of a transgenic DSX-TTAV-RED strain was carried out by DSX-tTAV-Red adult injection survivors (Generation 0 or $G_0$) were back crossed to Latin WT. Two $G_0$ males were crossed to 10 Latin WT females and 6 $G_0$ females were crossed with 6 Latin WT males. $G_1$ pupae were screened for DsRed2 fluorescence using a Leica M80 microscope equipped with filters for detection: maximum excitation 563 nm, emission 582 nm. Ten $G_1$ transgenic families were obtained (8 from male $G_0$ crosses, 2 from female $G_0$ crosses) from which 3 individual $G_2$ males were crossed to WT females, resulting in 20 transgenic strains producing viable eggs. Strains were maintained by crossing $G_3$ males to Latin WT females. $G_4$ hemizygous progeny from all strains were assessed for their survivability when reared in the presence and absence of antidote (doxycycline hyclate). Fifteen strains presented the desired phenotype; an unbiased sex ratio in the presence of doxycycline and complete female penetrance in the absence of doxycycline (i.e., no female survival). Strains not showing this phenotype were discarded. Assessment of adult eclosion and survival of individuals carrying the DSX-tTAV-Red transgene suggests that pupae from these 15 strains can successfully eclose into adults. Results from the two relevant strains (O and S) are displayed in FIG. 5.

Figure 4:
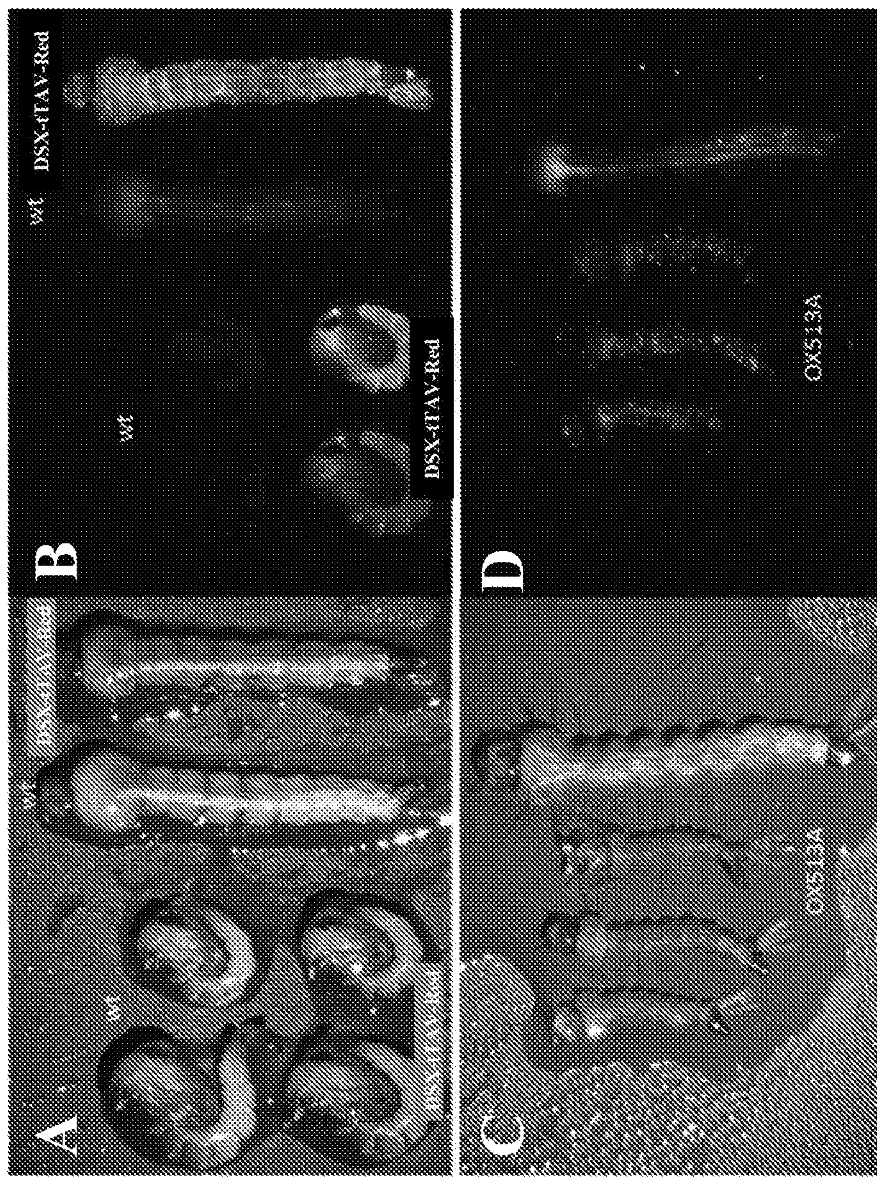
FIG. 4 shows Images of DSX-tTAV-Red-O, OX513A and WT life stages expressing the DsRed2 marker under white light and fluorescent light. Panel A: wild type (wt) pupae and larva, DSX-tTAV-Red-O pupae and larva under white light; Panel B: the same pupae and larvae shown in A under fluorescent light; Panel C: OX513A larvae under white light; Panel D: the same larvae shown in C under fluorescent light.
Figure 6:
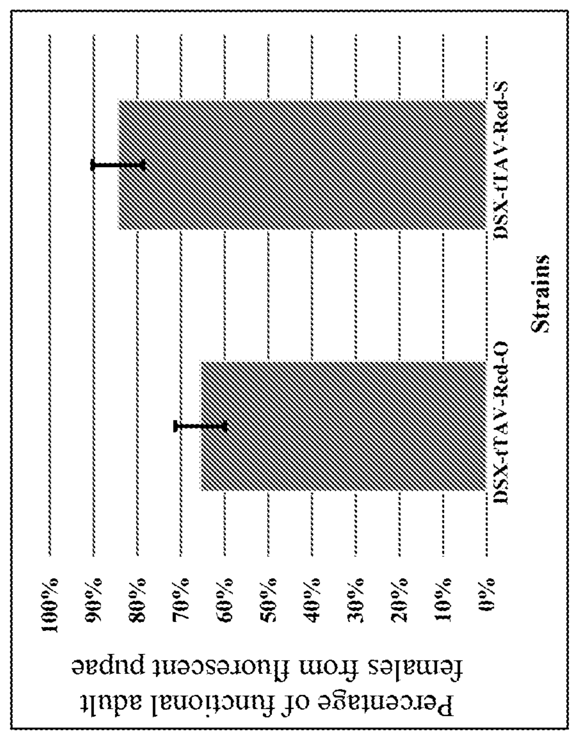
FIG. 6 shows functional DSX-tTAV-Red adult female eclosion. Percentages are the means of fluorescent female pupae eclosing into functional adults. 95% confidence intervals are displayed. Of the fluorescent pupae collected from hemizygous crossed individuals, the ratio of hemizygotes to homozygotes is expected to be 2:1 (based on Mendelian genetics). Any adult eclosion over 50% indicates survival of homozygotes under permissive conditions.

Assessment of the potential zygosity of the strains was carried out by screening the pupae from $G_5$ hemizygous crosses according to Mendelian genetics (3:1 ratio fluorescent:non fluorescent) where homozygotes are expected to have a brighter fluorescent phenotype. Nine strains presenting with over 10% survival of potential homozygotes were selected for eclosion assessment. Results from the two strains (DSX-tTAV-Red-O and DSX-tTAV-Red-S) are shown in FIG. 6. Nine strains were found to have the expected Mendelian inheritance ratios and these were further evaluated by crossing male and females expressing the bright phenotype (families of 1 male to 2 females) and PCR analysis (genotyping). Progeny of the crosses were screened for fluorescence over 2 generations (Representative Fluorescent larval/pupal stages shown in FIG. 4) resulting in a homozygous DSX-tTAV-Red-O substrain from 16 parents (7 male and 9 female) and DSX-tTAV-Red-S strain from 70 parents (29 male and 41 female). Despite the fact that integration occurred in the same position within the mosquito chromosome for each transgenic event, only substrains O and S showed the desired phenotype. The mosquitoes are not inbred, so there are small variations in the chromosome near the site of integration which may influence whether the inserted genetic material functions or does not. Therefore, we assessed the precise integration point of the vector and designed an assay to detect divergence in the mosquitoes and approximate the variations present in the *Aedes aegypti* population.

To ensure DSX-tTAV-Red homozygotes successfully eclosed into viable adults, survivorship was assessed. Of the fluorescent pupae, the expected ratio of hemizygotes to homozygotes would be 2:1, according to Mendelian genetics. Two strains, O and S were identified as suitable candidates, with the proportion of potential homozygotes being 15.6% and 34.4%, respectively (FIG. 6). Strain S4a was later found to contain two insertions of the DSX-TTAV-RED transgene. These were separated prior to homozygosis of the strain.

Not all strains tested satisfied all criteria. While not wishing to be bound by any particular the transgenic event and insertion into particular areas of the *Aedes aegypti* chromosome influences the expression of the gene and observed phenotype. The summary of the strain selection is shown in FIG. 7.

Example 4: Protocol for Detection of DSX-tTAV-Red Transgene

This assay was used to detect the presence or absence of the DSX-tTAV-Red transgene in a variety of DSX-tTAV-Red insect samples (field, mass-rearing and laboratory). The same protocol can also be used to provide evidence of stability of the DSX-tTAV-Red transgene over time. Successful amplification of the DSX-tTAV-Red transgene over time provides evidence of its stability, as one primer anneals to the transgene, the other to the flanking genomic sequence, so mobilisation of the transgene results in a negative PCR.

a. Extraction of Genomic DNA

Genomic DNA was isolated from individual insects using the protocol below using the Invitrogen Purelink™ genomic extraction kit.

A solution of 96-100% ethanol is added to PureLink™ Genomic Wash Buffer and PureLink™ Genomic Wash Buffer 2 according to Instructions on each label (Invitrogen) and mixed well.

180 μL of PureLink™ Genomic Digestion Buffer and 20 μL Proteinase K is added to each pool of abdomens. The insect samples are broken up with a sterile pestle, ensuring that the tissue is completely immersed in the buffer mix. The solutions are incubated at 55° C. with occasional vortexing until lysis is complete (1-4 hours). Alternatively, the samples may be placed overnight to digest.

The samples are centrifuged at maximum speed for 3 minutes at room temperature to remove any particulate materials, and the supernatant is transferred to a new microcentrifuge tube. 20 μL RNase A is added to lysate, and mixed well by briefly vortexing, then incubate at room temperature for 2 minutes.

200 μL PureLink™ Genomic Lysis/Binding Buffer is added and mixed well by vortexing to yield a homogenous solution. 200 μL 96-100% ethanol is then added to the lysate. The lysates are mixed well by vortexing to yield a homogenous solution. Alternatively, the Lysis/binding buffer and 100% Ethanol can be mixed before adding.

The lysate (~640 μL) prepared with PureLink™ Genomic Lysis/Binding Buffer and ethanol is added to the PureLink™ Spin Column in a Collection Tube from the kit.

The columns are then centrifuged at 10,000×g for 1 minute at room temperature. The collection tube is discarded and the spin column is placed into a clean PureLink™ Collection Tube supplied with the kit.

500 μL Wash Buffer 1 prepared with ethanol is added to the column and the column is centrifuged at 10,000×g for 1 minute at room temperature. The collection tube is discarded and the spin column is placed into a clean PureLink™ Collection Tube supplied with the kit.

500 μL of Wash Buffer 2 prepared with ethanol is added to the column and the column is centrifuged at maximum speed for 3 minutes at room temperature. The flow through is discarded and the column is re-spun for a further minute at 10,000×g.

The spin column is placed in a sterile 1.5-ml microcentrifuge tube and 100 μL of PureLink™ Genomic Elution Buffer is added to the column. The column is incubated at room temperature for 1 minute then centrifuged at maximum speed for 1 minute at room temperature. The column is then removed and discarded and the purified DNA collected is used or stored the purified DNA at 4° C. (short-term) or −20° C. (long-term).

It was found that for the DSX-TTAV-RED-O strain, the DSX-TTAV-RED rDNA was inserted at supercont1.420 position 324552, between gene AAEL009696 and an exon in gene AAEL009706, while for the DSX-TTAV-RED-S strain, the DSX-TTAV-RED rDNA was inserted at supercont1.19 position 2799615, also known as contig AAGE02001348.1 position 88740.

For the DSX-TTAV-RED-O strain, the insertion of DSX-TTAV-RED rDNA in the *Aedes aegypti* genome, the rDNA is inserted in a region corresponding to a sequence of SEQ ID NO: 46 between nucleotides 1845 and 1850. The rDNA insert is flanked on the 5' end by sequence of the *Aedes aegypti* genome corresponding to nucleotides 1443 to 1845 of SEQ ID NO: 46 (SEQ ID NO: 73) and on the 3' end by sequence of the *Aedes aegypti* genome corresponding to nucleotides 1859 to 2222 of SEQ ID NO: 46 (SEQ ID NO: 74).

For the DSX-TTAV-RED-S strain, the insertion of DSX-TTAV-RED rDNA in the *Aedes aegypti* genome, the rDNA is flanked on the 5' end by sequence of the *Aedes aegypti* genome corresponding to SEQ ID NO: 75 and on the 3' end by sequence of the *Aedes aegypti* genome corresponding to SEQ ID NO: 76.

PCR for Genotyping DSX-tTAV-Red-O and DSX-tTAV-Red-S

A) DSX-tTAV-Red-O

Genotyping for DSX-tTAV-Red-O strain was carried out by Taqman real-time PCR. The DSX-tTAV-Red transgene is quantified by normalising qPCR Ct values to an internal reference gene, IAP. Relative copy number of the DSX-tTAV-Red transgene is calculated by comparing the normalised Ct values for DSX-tTAV-Red in the (known heterozygote) calibrator sample with that in each unknown sample. The relative copy number of DSX-tTAV-Red rDNA in the unknown samples are expected to be ~1 for hemizygotes and ~2 for homozygotes, although inefficiencies in amplification under these conditions led to individuals with relative DSX-tTAV-Red copy number >1.2 being considered to be homozygotes.

The PCR was carried out using TaqMan® Gene Expression Master Mix (ThermoFisher Scientific) under the following conditions: initial denaturation and enzyme activation at 95° C. for 10 mins, 43 cycles of denaturation at 94° C. for 11 s, probe annealing at 60° C. for 15 s, primers annealing at 54° C. for 30 s and extension at 60° C. for 30 s.

| Oligonucleotide name | Target | Sequence (SEQ ID NO) | Fluorescent quencher/label |
|---|---|---|---|
| 711-VP16taqF | DSX-tTAV-Red-O | CATGCCGACGCGCTAGA (SEQ ID NO: 47) | N/A |
| 712-VP16taqR | DSX-tTAV-Red-O | GGTAAACATCTGCTCAAACTCGAAGTC (SEQ ID NO: 48) | N/A |
| 2131-VP16probe2 | DSX-tTAV-Red-O | FAM-TCGATCTGGACATGTTGGGGGACG-BHQ1 (SEQ ID NO: 49) | BHQ1, FAM |

-continued

| Oligonucleotide name | Target | Sequence (SEQ ID NO) | Fluorescent quencher/label |
|---|---|---|---|
| SS1752-AedesF | IAP | CTGCAGTAGTGATGAAGATGAACCA (SEQ ID NO: 50) | N/A |
| SS1753-AedesR | IAP | GGGCGAAAATGCCGTATTGTACTCA (SEQ ID NO: 51) | N/A |
| SS1884-AedesPro | IAP | HEX-AGACACCAGTCGGACTTGCAAAATCTG-BHQ1 (SEQ ID NO: 52) | BHQ1, HEX |

B. DSX-tTAV-Red-S

Genotyping for DSX-tTAV-Red-S was carried out by endpoint PCR using the oligonucleotides shown below and the following PCR conditions: 94° C., 2 min; 3-5 cycles of 94° C. 15 s, 60° C. 30 s −0.5° C./cycle, 72° C. 15 s; 23 cycles of 94° C. 15 s, 55° C. 30 s, 72° C. 15 s; 72° C. 7 min; 4° C. hold. Wild-type PCR product (240 bp) was the result of amplification with primers SS2326)5034S5R1 and SS2336)5034S3F2. DSX-tTAV-Red PCR product (221 bp) was the result of amplification with primers SS2326)5034S5R3 and TD225)Mod-666-sal.

| Oligonucleotide name | Target | Sequence | SEQ ID NO |
|---|---|---|---|
| SS2326 | DSX-tTAV-Red-S 5' flanking sequence | GCTTCATTAAGCAGAAACACTGA | SEQ ID NO: 53 |
| TD225)Mod-666-sal | DSX-tTAV-Red-S transgene | TGACAAGCACGCCTCACGGGAG | SEQ ID NO: 55 |
| SS2336)5034S3F2 | DSX-tTAV-Red-S 3' flanking sequence | CATCTAACTCTACTTTGTGTGGGAATCA | SEQ ID NO: 54 |

Transgene specific gene sequences are amplified by PCR using PCR BIO polymerase as follows:

To amplify the insert in the DSX-tTAV-RED-O substrain, two specific oligonucleotide primers were designed: TD4037 (5'-CTGTTGCTGCGCACGAAACAC-3'; SEQ ID NO: 38) which anneals to the *Aedes aegypti* genomic DNA, and TD2127 (5'-GTGCCAAAGTTGTTTCTGACTGAC-3'; SEQ ID NO: 39) which anneals to the inserted construct in a region shown in SEQ ID NO: 36. This primer set only amplifies samples containing the DSX-tTAV-RED-O transgene (data not shown).

To amplify the insert in the DSX-tTAV-RED-S substrain, two specific oligonucleotide primers were designed: TD4037 (5'-TGACAAGCACGCCTCACGGGAG-3'; SEQ ID NO:41) which anneals to the *Aedes aegypti* genomic DNA, and TD225 (5'-GCTTCATTAAGCAGAAACACTGA-3'; SEQ ID NO: 40) which anneals to the inserted construct in a region shown in SEQ ID NO: 37, and produces a product of 221 bp. This primer set only amplifies samples containing the DSX-tTAV-RED-S transgene.

Other methods for amplifying and detecting the transgene are as follows:

1. Endpoint PCR Detection Methods 1.1 Detection of DSX-tTAV-Red rDNA

In the first method, PCR primers may be designed such that one primer anneals within the DSX-tTAV-Red rDNA and the other primer anneals to *Aedes aegypti* DNA in the region flanking the insertion site of the OX5034 rDNA. Such primers can be as close together or as far away (in terms of bp) from one another as desired. For convenience, we generally design for amplicons that are 200-500 bp for agarose gel analysis, 200 bp for qPCR with SybrGreen, and 100 bp for Taqman qPCR.

These primers may be used to amplify a suitable PCR amplicon which may be detected by agarose gel DNA electrophoresis using an intercalating dye such as ethidium bromide.

For example, DSX-tTAV-Red-O rDNA may be detected using the following primers:

| | Primer ID | Sequence |
|---|---|---|
| Primer 1 | 4039)5034Ofla4 | CTGTTGCTGCGCACGAAACAC (SEQ ID NO: 56) |
| Primer 2 | 2127)PB4-2 | GTGCCAAAGTTGTTTCTGACTGAC (SEQ ID NO: 57) |

For example, DSX-tTAV-Red-S rDNA may be detected using the following primers:

| | Primer ID | Sequence |
|---|---|---|
| Primer 1 | SS2326)5034S5R3 | GCTTCATTAAGCAGAAACACTGA (SEQ ID NO: 53) |
| Primer 2 | TD225)Mod-666-sal | TGACAAGCACGCCTCACGGGAG (SEQ ID NO: 55) |

Figure 8:
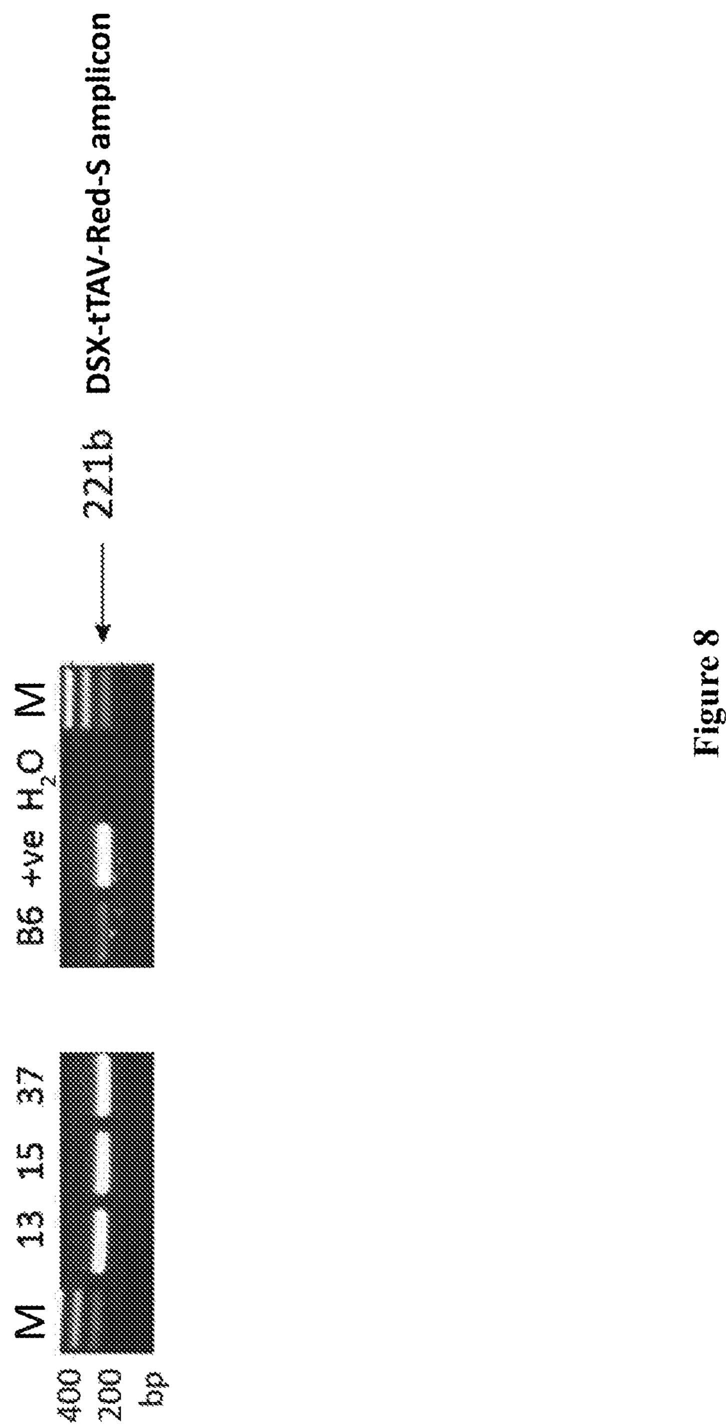
FIG. 8 is a representative gel showing PCR products using primers SS2326 and TD225)Mod-666-sal to amplify across the genomic DNA-transgene rDNA boundary in DSX-tTAV-Red-S. Expected amplicon size: 221 bp. Samples 13, 15, 37, and B6 represent individual mosquitoes screened for the presence of the DSX-tTAV-Red-S transgene insertion. Sample '+ve' is a known DSX-tTAV-Red-S individual and '$H_2O$' is a no-DNA negative control sample. M indicates molecular weight markers.

A representative gel showing amplification of PCR products using primers SS2326)5034S5R3 and TD225)Mod-666-sal to amplify across the genomic DNA-transgene rDNA boundary in DSX-tTAV-Red-S with an expected amplicon size of 221 bp is shown in FIG. 8.

1.2 Detection of Wild-Type Alleles

Figure 9:
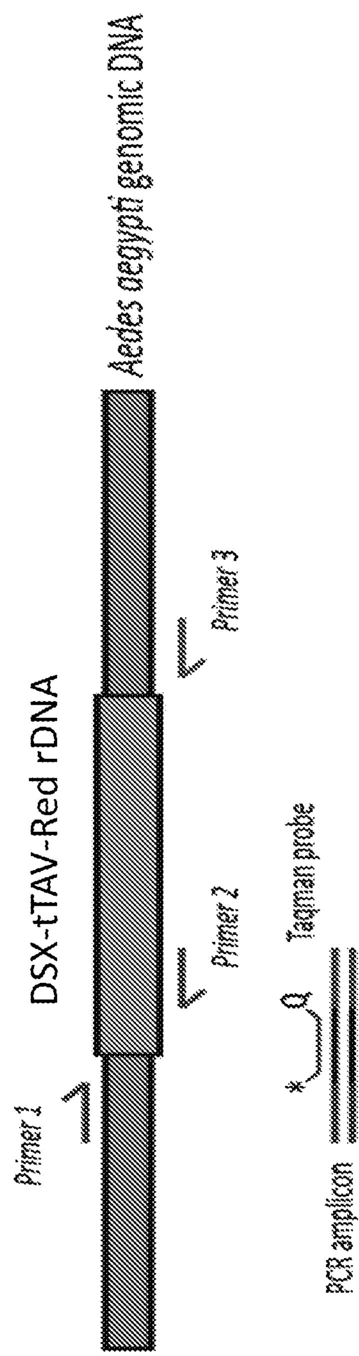
FIG. 9 presents a schematic figure showing detection methods for DSX-tTAV-Red rDNA in *Aedes aegypti* genomic DNA. Primer 1 anneals to DNA in the region flanking the insertion site of the DSX-tTAV-Red rDNA. Primer 2 anneals to DNA within the DSX-tTAV-Red rDNA. A Taqman probe annealing to the amplicon is also depicted, where '*' represents a generic fluorophore and 'Q' represents a generic quencher in the Taqman probe. Primer 3 anneals to DNA in the region flanking the other end of the insertion site.
Figure 10:
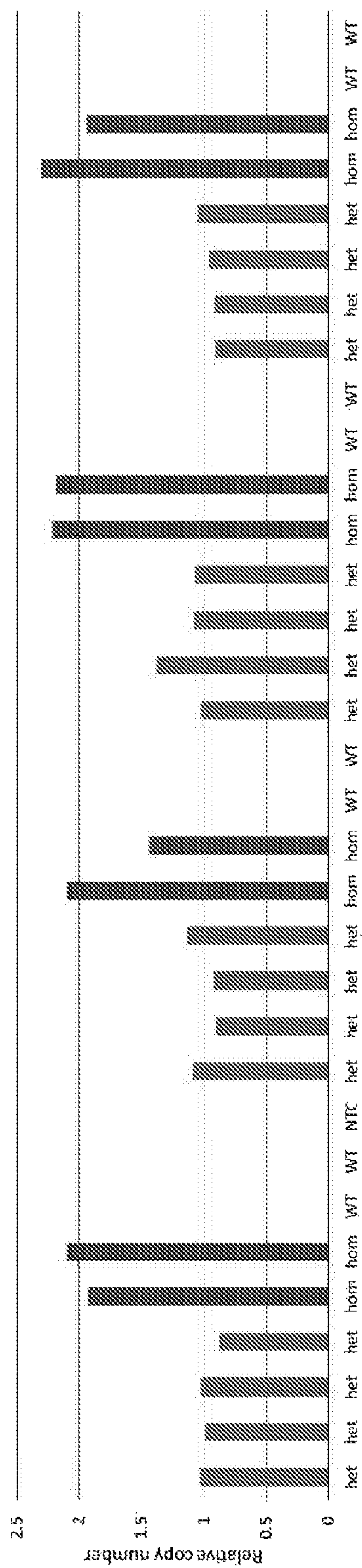
FIG. 10 shows relative copy number of the DSX-tTAV-Red rDNA detected in DSX-tTAV-Red-O homozygous individual mosquitoes (hom, in red), DSX-tTAV-Red-O hemizygous individuals (het, in blue) and wild-type individuals (WT). A no-DNA control reaction (NTC) was also carried out. These data were generated using the primers and probe outlined in Table 10. Relative copy number was calculated by first normalising Ct (cycle threshold) values to Ct values obtained for an endogenous *Aedes aegypti* gene (IAP1), and then normalising Ct values to DSX-tTAV-Red rDNA Ct values obtained for an DSX-tTAV-Red rDNA homozygous individual.

This assay method may also be adapted to detect the absence of the DSX-tTAV-Red rDNA (for example in DSX-tTAV-Red hemizygous individuals or in wild/wild-type mosquitoes) by designing a PCR reaction using primers annealing either side of the insertion site of the DSX-tTAV-Red rDNA (i.e., Primer 1 and Primer 3, FIG. 9). However, the presence of natural variation in the *Aedes aegypti* genome means that multiple primer sets may be required to amplify the various wild-type alleles that exist within a population (e.g., 3 wild-type alleles have been discovered in the lab population), and the discovery of further wild-type alleles will necessitate the design of further primer sets along the lines outlined here.

DSX-tTAV-Red-O wild-type alleles:

| | Primer ID | Sequence |
|---|---|---|
| Wild-type allele 1 | | |
| Primer 1 | TD4037)5034Ofla2 | GATGGTCCCTAGAAACAGCTTTCC (SEQ ID NO: 58) |
| Primer 3 | TD4039)5034Ofla4 | CTGTTGCTGCGCACGAAACAC (SEQ ID NO: 59) |
| Wild-type allele 2 | | |
| Primer 1 | TD4305)OX5034OWtF2 | TCGATCAACTAACTGAAATCGATGA (SEQ ID NO: 60) |
| Primer 3 | TD4324)OX5034Wt2R | CCTAAGACCGTTAACATTTCAAGTGAC (SEQ ID NO: 61) |
| Wild-type allele 3 | | |
| Primer 1 | TD4393)OX5034Oal2F | CTTCGAGAGTAAGCGGAAACTCC (SEQ ID NO: 62) |
| Primer 3 | TD4394)OX5034Oal2R | AGTATTAGCATCCGAAGCTCATGAC (SEQ ID NO: 63) |

DSX-tTAV-S wild-type alleles:

| | Primer ID | Sequence |
|---|---|---|
| Wild-type allele 1 | | |
| Primer 1 | SS2326)5034S5R1 | GCTTCATTAAGCAGAAACACTGA (SEQ ID NO: 64) |
| Primer 3 | and SS2336)5034S3F2 | CATCTAACTCTACTTTGTGTGGGAATCA (SEQ ID NO: 54) |

The PCR reaction mix for endpoint PCR detection methods is as follows:

12.8 μL MilliQ water
4 μL Biotaq buffer
0.5 μL 10×BSA
0.25 μL Primer 1 (10 μM)
0.25 μL Primer 2/Primer 3 (10 μM)
0.2 μL PCRBIO Taq polymerase (PCR Biosystems)
2 μl template gDNA at a concentration of approximately 10 ng/uL PCR Cycling:
Step 1) 94° C. 2 min
Step 2) 94° C. 15 s
Step 3) 60° C. 30 s −0.5° C./cycle
Step 4) 72° C. 15 s
Step 5) Repeat Steps 2 to 4 nine more times.
Step 6) 94° C. 15 s
Step 7) 55° C. 30 s
Step 8) 72° C. 15 s
Step 9) Repeat Steps 6 to 8 nineteen more times
Step 10) 72° C. 7 min
Step 11) 4° C. hold PCR reaction mixtures are analysed on an appropriate agarose gel containing ethidium bromide or a similar DNA intercalating dye such as SYBR-safe.

2. SYBR-Green qPCR Detection Methods

In a variation on the endpoint PCR method, amplification may be detected by quantitative real-time PCR (qPCR) using an intercalating due such as SYBR-Green.

For qPCR amplification/detection, primers are designed to amplify a product of around 200 bp, using standard parameters:

Length 18-40 bp
Predicted $T_m$ approx 55° C.,
GC content between 30-70%
No significant secondary structure: dimer/hairpin dG<3.

Primers for DSX-tTAV-Red-O rDNA:

| | Primer ID | Sequence | Amplicon size (bp) |
|---|---|---|---|
| Primer 1 | TD4039)5034Ofla4 | CTGTTGCTGCGCACGAAACAC (SEQ ID NO: 56) | 219 |
| Primer 2 | SS218)PB3 | CAGACCGATAAAACACATGCGTCA (SEQ ID NO: 65) | |

Primers for DSX-tTAV-Red-S rDNA:

| | Primer ID | Sequence | Amplicon size (bp) |
|---|---|---|---|
| Primer 1 | TD225)Mod-666-sal | TGACAAGCACGCCTCACGGGAG (SEQ ID NO: 55) | 218 |
| Primer 2 | SS2326)5034S5R1 | GCTTCATTAAGCAGAAACACTGA (SEQ ID NO: 64) | |

Primers for DSX-tTAV-Red-O wild-type alleles:

| | Primer ID | Sequence | Amplicon size (bp) |
|---|---|---|---|
| Wild-type allele 1 | | | |
| Primer 1 | SS2399)OX5034OWT1R | TCGACTCATGGAGGTTTCACTG (SEQ ID NO: 66) | 177 |
| Primer 3 | SS2398)OX5034WT1F | ATGCGTTGCATTGTTATTCAATG (SEQ ID NO: 67) | |
| Wild-type allele 2 | | | |
| Primer 1 | TD4324)OX5034Wt2R | CCTAAGACCGTTAACATTTCAAGTGAC (SEQ ID NO: 61) | 333 |
| Primer 3 | SS2401)OX5034WT2F2 | AAATATCAGCCTCAAATAAGCACTT (SEQ ID NO: 68) | |
| Wild-type allele 3 | | | |
| Primer 1 | TD4394)OX5034Oal2R | AGTATTAGCATCCGAAGCTCATGAC (SEQ ID NO: 63) | 330 |
| Primer 3 | TD4393)OX5034Oal2F | CTTCGAGAGTAAGCGGAAACTCC (SEQ ID NO: 62) | |

Primers for DSX-tTAV-Red-S wild-type allele:

| | Primer ID | Sequence | Amplicon size (bp) |
|---|---|---|---|
| Wild-type allele 1 | | | |
| Primer 1 | 2335)5034S3F1 | CTATAGCTTTCTGGTGTACGGAATA GAG (SEQ ID NO: 69) | 218 |
| Primer 3 | SS2327)5034S5R2 | GGTCTCATAAGTATAACTCTGCACA GAG (SEQ ID NO: 70) | |

*Aedes aegypti* endogenous control primers and probe (IAP1):

| | Primer ID | Sequence |
|---|---|---|
| Primer 1 | SS2320)AedesF2 | TGCAGTAGTGATGAAGATGAACCA (SEQ ID NO: 71) |
| Primer 2 | SS2321)AedesR2 | CGAAAATGCCGTATTGTACTCA (SEQ ID NO: 72) |

Reaction Mix per well (using qPCR kit, SuperMix-UDG Platinum SYBR Green Cat #10633863 from Thermofisher):

4.1 μl MilliQ Water
0.4 μL Primer 1 (10 μM)
0.4 μL Primer 2 (10 μM)
0.1 μl ROX
10 μl SYBR Mastermix
5 μl template gDNA, approx. 1 ng/uL
PCR cycling:
Step 1) 50° C. 2 mins
Step 2) 95° C. 2 min
Step 3) 95° C. 15 s
Step 4) 60° C. 30 s
Step 5) Repeat Steps 3 to 4 thirty-nine more times.

Cycle threshold (Ct) values are converted to concentration using a standard calibration curve, normalised to an endogenous control PCR (e.g. *Aedes aegypti* IAP1 gene, Table 9)) and assessed against predetermined limits of detection and limits of quantification to determine whether the OX5034 rDNA or wild-type alleles are present in the insect sample.

3. Taqman qPCR Detection Methods

PCR primers may be designed such that one primer anneals within the DSX-tTAV-Red rDNA and the other primer anneals to *Aedes aegypti* DNA in the region flanking the insertion site of the DSX-tTAV-Red rDNA. These primers may be used to amplify a PCR amplicon which may be detected by quantitative real-time PCR (qPCR) using a Taqman probe designed to anneal to the PCR amplicon. Using this method, the presence and copy number of the transgene may be detected, such that it is possible to differentiate mosquitoes homozygous for the DSX-tTAV-Red rDNA from those hemizygous for the DSX-tTAV-Red rDNA and also from wild-type/wild mosquitoes.

Primers and probes are designed according to the following rules:

Probes: no G as 5' nucleotide
More Cs than Gs
$T_m$ 68-70° C.

Primers are designed to amplify a product of approx. 100 bp (less than 150 bp), using the following rules:

Length 18-40 bp
Tm 58-60° C. (or 5-10° C. lower than the Tm of the probe)
More A/Ts than G/Cs in the last 5 nucleotides (no GC clamp)
GC between 30-70%
No significant secondary structure: dimer/hairpin dG<3.

For example, DSX-tTAV-Red-O rDNA may be detected using the following primers and Taqman probe:

| | Primer ID | Sequence |
|---|---|---|
| Primer 1 | 2323)5034OtaqR | AAATGAAATTGCAAGTCCACTTT (SEQ ID NO: 77) |
| Primer 2 | 2322)PB5taqF | GCGTCAATTTTACGCAGACTATC (SEQ ID NO: 78) |
| Probe | 2325)5034OtaqPr | FAM-ACACCCGGCACGGTAAAATGTCA-BHQ1 (SEQ ID NO: 79) |

For example, DSX-tTAV-Red-S rDNA may be detected using the following primers and Taqman probe:

| | Primer ID | Sequence |
|---|---|---|
| Primer 1 | 2408)5034StaqR | AGCAGAAACACTGAATTTTCAAAG (SEQ ID NO: 80) |
| Primer 2 | 2322)PB5taqF | GCGTCAATTTTACGCAGACTATC (SEQ ID NO: 81) |
| Probe | 2407)5034Staqpr | FAM-ATGATGCGGAAGCGTAATCTTTACCCA-BHQ1 (SEQ ID NO: 82) |

Thus this reaction may be carried out as a multiplexed Taqman qPCR reaction.

The DSX-tTAV-Red rDNA may be detected by using a FAM-labelled rDNA probe, while a HEX-labelled endogenous control probe may be used to detect an endogenous *Aedes aegypti* single copy gene PCR amplicon, e.g., IAP1 (inhibitor of apoptosis gene 1). Relative copy number may be calculated by first normalising DSX-tTAV-Red rDNA Ct (cycle threshold) values to endogenous control Ct values, and then to DSX-tTAV-Red rDNA Ct values obtained for a known OX5034 rDNA homozygous individual.

Primers for *Aedes aegypti* endogenous control primers and probe (IAP1):

| | Primer ID | Sequence |
|---|---|---|
| Primer 1 | SS2320)AedesF2 | TGCAGTAGTGATGAAGATGAACCA (SEQ ID NO: 83) |
| Primer 2 | SS2321)AedesR2 | CGAAAATGCCGTATTGTACTCA (SEQ ID NO: 84) |
| Probe | 551884)AedesPro | HEX-AGACACCAGTCGGACTTGCAAAATCTG-BHQ1 (SEQ ID NO: 85) |

Reaction mix per well (using Applied Biosystems Taqman Gene expression master mix, cat #4369016 from Thermofisher):

1.4 µl MilliQ $H_2O$
0.6 µl OX5034 rDNA Primer 1 (10 µM)
0.6 µl OX5034 rDNA Primer 2 (10 µM)
0.6 µl endogenous control Primer 1 (10 µM)
0.6 µl endogenous control Primer 2 (10 µM)
10 µl Gene expression Master mix
0.6 µl OX5034 rDNA probe (10 µM)
0.6 µl endogenous control probe (10 µM)
5 µl Template gDNA (approx. 1 ng/uL)

PCR Cycling:
Step 1) 95° C. for 10 mins
Step 2) 94° C. for 15 secs
Step 3) 60° C. for 1 min (read fluorescence at the end of this step)
Step 4) Repeat steps 2 and 3 thirty-nine more times.

The invention claimed is:

1. A doublesex (dsx) splice control module comprising, from 5' to 3':

i. an exon 4 of dsx;

ii. a truncated intron 4 of dsx comprising a 5' terminal fragment of the dsx intron 4 and a 3' fragment of the dsx intron 4;

iii. an exon 5a of dsx;

iv. an intron 5 of dsx;

v. a modified exon 5b of dsx, wherein the modified dsx exon 5b is set forth in SEQ ID NO: 7;

vi. a truncated intron 6 of dsx comprising a 5' terminal fragment of the dsx intron 6 and a 3' fragment of the dsx intron 6; and vii. a 5' fragment of exon 6 of dsx, wherein said dsx is derived from *Aedes aegypti*.

2. The dsx splice control module of claim 1, wherein said modified exon 5b is modified with at least one substitution, insertion, and/or deletion to create an open reading frame for the entire exon, and wherein said splice control module is spliced on a sex-specific basis when introduced into an insect.

3. The dsx splice control module of claim 2, wherein said insect is a Diptera of a species selected from the group consisting of *Ceratitis capitata, Anastrepha ludens, Bactrocera dorsalis, Bactrocera oleae, Bactrocera cucurbitae, Ceratitis rosa, Rhagoletis cerasi, Bactrocera tyroni, Bactrocera zonata, Anastrepha suspense, Anastrepha obliqua, Aedes aegypti, Aedes albopictus, Anopheles stephensi, Anopheles albimanus*, and *Anopheles gambiae*.

4. A comprising a polynucleotide comprising the doublesex (dsx) splice control module of claim 1 operably linked to a polynucleotide sequence encoding a heterologous protein, wherein said heterologous protein is lethal, deleterious, or sterilizing to an insect.

5. The polynucleotide of claim 4, wherein said heterologous protein is a protein selected from the group consisting tTAV, tTAV2, tTAV3, an apoptosis-inducing factor, Hid, Reaper (Rpr), and NipplDm.

6. The polynucleotide of claim 4, further comprising a polynucleotide sequence encoding a ubiquitin Fusion Leader Polypeptide fused in frame to the 5' end of said polynucleotide sequence encoding said heterologous protein.

7. The polynucleotide of claim 6, further comprising a 5' untranslated region (5'UTR) operably linked 5' of said dsx splice control module, wherein said 5'UTR comprises a promoter operable in an insect and a tetracycline-responsive operator.

8. The polynucleotide of claim 7, wherein said promoter is a *Drosophila melanogaster* minimal HSP70 promoter (DmHsp70).

9. The polynucleotide of claim 6, further comprising a 3' untranslated region (3'UTR) operably linked 3' of said polynucleotide sequence encoding said heterologous protein.

10. The polynucleotide of claim 9, wherein said 3'UTR is an SV40 3'UTR.

11. An expression vector plasmid comprising the polynucleotide of claim 4.

* * * * *

UNITED STATES PATENT AND TRADEMARK OFFICE

CERTIFICATE OF CORRECTION

PATENT NO. : 11,827,876 B2
APPLICATION NO. : 16/324078
DATED : November 28, 2023
INVENTOR(S) : Luke Alphey It is certified that error appears in the above-identified patent and that said Letters Patent is hereby corrected as shown below:

In the Claims

Column 114, Lines 15-20 Claim 4 reads:
"4. A comprising a polynucleotide comprising the doublesex (dsx) splice control module of claim 1 operably linked to a polynucleotide sequence encoding a heterologous protein, wherein said heterologous protein is lethal, deleterious, or sterilizing to an insect."

Should read:
-- 4. A polynucleotide comprising the doublesex (dsx) splice control module of claim 1 operably linked to a polynucleotide sequence encoding a heterologous protein, wherein said heterologous protein is lethal, deleterious, or sterilizing to an insect. --

Signed and Sealed this
Twenty-eighth Day of May, 2024

Katherine Kelly Vidal

Katherine Kelly Vidal
*Director of the United States Patent and Trademark Office*

SEQUENCE LISTING

```
<160> NUMBER OF SEQ ID NOS: 85

<210> SEQ ID NO 1
<211> LENGTH: 4043
<212> TYPE: DNA
<213> ORGANISM: Aedes aegypti

<400> SEQUENCE: 1

tccggcgagc tggactgtga ccgggtacga aaatcggcac atggcgaccg tgacgcagac      60

ggagtgcggg tgacggagat gttctcctcg tccggccagt gtctgtgtct gctggaacgc     120
```

-continued

```
ttcggaaagt agatgcaaca aatgtcgtat cctgtttgag ggattgaatt attggggggc    180
gaaagtgggg aaagaaaatg taaaatagaa caaattattt attgtttata gaaaagtgta    240
atgctgttaa gaggttagta tactcaatgt ctttccatca aatacggtta gaaattgttc    300
attctatgga gattgcacga cgccacgagt ttgattttac cttttgatgt ttgtcacaaa    360
cagcactagg tactgtaatt ttgaggtgat gcaaataaat tttgaaccat cctgctgaac    420
acaaatttat tagacgtatt tcgacgtttg gtgagctcgt ttccatactt gcctatctta    480
cgttacttca atgaacaact aaatacacat ttgtatgcgc ttatccccta aagacgggtg    540
ataatgtcaa ctgtttagct aatttccaaa acaatcaaac cttgatacga gataactgac    600
tttgcatctc tcaaactacg attaatagaa agctatagca aattatgtac ttagatagca    660
ttggaaagat gacgctttcc gctacctcat aacgccattg gctttatcta tatgactgtt    720
catagctgga gagatggatt tgaaggtcta attctaagtt atcgcatatc aaggtatcgt    780
tgtgctggaa aatctgatct gacagtatcg aaatagcgca actctttgta cccaataatg    840
gaaagttctg atttattgta tttataaaaa cgttgtctat ttgttccgat ttcaggtcgt    900
caaatcactt gctagtaaat aacgtctcca tagcaattat cattattata tactaaatga    960
aacgagctca ccaattagat agtttcaaac agttatacag ttgcttcaaa caacatacat   1020
acatgccttg ataagtaccg tgcgccaaat cgagctcgca acatgagtat gaaaagccac   1080
tagtaacaca ttgataatca gcatagaatt taaaataaaa taatatttta tactgtggat   1140
atcttcataa cactgcacgc tgatataaaa ttcagaacta caaaaggatc gttgaaattt   1200
tacgtaactc aacagagtaa gggagggggt cttccgaaat gctacggtct atacacaaaa   1260
tttaaatttt tcacacaaaa gccgttacgt ggaggaggga ggggttctaa aattggcaaa   1320
ctttgcgtca cgtaatattt gaatcatccc aaagaaaata aacttctatg ctgattataa   1380
cgcgcgcaga acaatggttg cggtgagaga cattaacagg cttgtttgtg gtgctgaaat   1440
agaacttgtc atcaatatgt tttagctggt taaactatac aatcattacg tagcctgaaa   1500
atcacccttg aaaaggccga atatatgacg aaaagacaca ctctccaact caaaaggcaa   1560
actcaacgtg gtcgtgcaca acctccaata gcagtacctg tcggagccgt ttggcaacgg   1620
ccagctacca aaatacgctc gcaatggcat gcaagctaca gagagataag tgtttatcag   1680
atcattttgg gcaccgaaac cgaccgatgt cggaaacgat tgaagagata taatctctgg   1740
tttgtagatt gtaggatggt tggttgaaga tccggtttcc cggatttttt cggatggatg   1800
ttgcttgttg atgattctgc tgtcgtcgtt tttttccggt ggcagatgga acagcctcac   1860
ttcggctttc gaaacacaat cttcaaagtt aagtactact gctgttttgc attttttaaa   1920
ttttccctct gaaacttgct ttgcactatt ggtttcatca cttgtttgca ctttcacact   1980
ctttaggaac gctgtctcac aagtagagct cacgtggtag ccccagaatg gctgcatgtc   2040
gctattatcg ttaaacagca tttgcactgt ggtcattatg ttgtttgtat tagagttcgt   2100
cgcgttcgtg gaattgggaa ggagaagata cagaattact caaatgaaac cattccacgg   2160
gagaatacat ttcaggttta atcttattct tctaggacga aagcccatcg acagagtctt   2220
gcaggcttcc gtcgatcgac tttcacccgt ggatgctaag gaagcttata atgacctcaa   2280
cattctccgc gcacaggttg gctctattct gtttcacagt ttccggtgca gttgtgacga   2340
actcagacga atacccacga ttgtatgtcc aacctcattt tttatctttg taaactaacg   2400
tcgaaaaatc tagatactac atttctgctt tgcttcatct tacactaatc actagtttga   2460
acttgcgggt tttccgttat gctttgtaaa tatgcgatgc tttagagttt tcttcgttcc   2520
```

```
gattcttctt tgcattcgat tgcttcttcc gtcgaatcga tctgatcttc gtggtttatt   2580

cttgtttcgg ttcgaccttt gccgcagcgc agtgggtcgt gctgatcgtg taaaaagtct   2640

atcatccgga ctggcgcgtc gtactgcgca actctacacc gtcgaacatg ttcagattgt   2700

gcaatcgtga gtattcattg accacggctt gacctgcgag gcagagaaga acagttggat   2760

ttttcggata ttggtacgac ccgggggccg cgttgtcatc agttgcatga atcgttggtc   2820

caagttcgac gaaacgatat ggacatcggt gtttcggtgg accaagatcg acgacacgat   2880

cttggtcatg agtgtttttc ggtggaccta gagatattgc aacgaccgga gtggaatacg   2940

acggtacgat gttggtttgt actgttctgg acgctagtta cttcattgat acgataaagt   3000

ttacattcgt catatctctt gcttttcttg aatccaaatg cttaggacgt gtaaccttca   3060

caaaccgtca taaatcagtt tcgattcact acatgttgta gttattcagg ctcttataat   3120

tgaatattca aaaatcgaat tttctatttt atcttgatca gaggatataa ctcgcttaaa   3180

atgcacaatt ttattagcga caccatgtgg atttgtttta attgaaacct ctatcttctc   3240

atatgtatca cgatataaaa tgctcatttt attgactgtt taacgataaa cttgcgacga   3300

tcgacgcacc accgacctaa ttccattgtg gaagcaaggg gcactgcaat accgaaatgt   3360

gaagtaaatt tcaaatctgc tattatagac gatgatctaa tactcttgaa tggtcttaaa   3420

cgtgagttgt atttcaagaa gttatgacga ttcgattttg gggccattat gaccccaaaa   3480

cccagccaac gtaactttta ttagtacaga cagaaggtca agcgtgcaag tctttcatcc   3540

gtgtgtcaat aaggccatca gttgaaaccg tgtcaattaa ccctccagtt aacccttttta   3600

acttttacca ggacaaacca atgacttcgt gcgcaaattc caccactcgt tgtctcaggc   3660

cttgagttgt tgtttgataa gaatgggggga tgtcaagtcg gggagcgtag cccaacaggc   3720

tacggaaact gcatgatggc agtgtttgat ccagggcact gttgggaata gactccgtcg   3780

accgaagatc ccagatgtcc tgaaactcaa taataagcgt tagcagttac aaaatgggag   3840

cacccaggaa gtgagtgaca cccgatcgat acctcggaaa cagtcccaac cggtaagaac   3900

ccccatacct tcgtcaatcc gttggcgcgc tttattgacg tctccgtcgg cgcctttcag   3960

tatcacgtac atcaggggca tcatctccca ggggtatcgc agcttctcca ggagccattg   4020

agatcgtttg acaagttcgt cgt                                           4043
```

<210> SEQ ID NO 2
<211> LENGTH: 225
<212> TYPE: DNA
<213> ORGANISM: Drosophila melanogaster

<400> SEQUENCE: 2

```
cagatcttcg tcaagaccct gaccggcaag accatcaccc tggaggtgga gccgagcgat     60

accatcgaga acgtgaaggc caagatccag gacaaggagg gcatcccgcc ggatcagcag    120

cgcctgatct tcgccggacg ccagctggag gatggccgca ccctgagcga ctacaacatc    180

cagaaggaga gcaccctgca cctggtgctg cgcctgcgcg gtggt                   225
```

<210> SEQ ID NO 3
<211> LENGTH: 1011
<212> TYPE: DNA
<213> ORGANISM: Artificial Sequence
<220> FEATURE:
<223> OTHER INFORMATION: synthetic tetracycline responsive activator

<400> SEQUENCE: 3

```
gtcagccgcc tggataagtc caaagtcatc aactccgcgt tggagctgtt gaacgaagtt     60
ggcattgagg gactgacgac ccgcaagttg gcgcagaagc tgggcgtgga gcagcccacc    120
ctctactggc acgtgaagaa taagcgggcg ctgctggatg ccctggccat cgagatgctc    180
gaccgccacc acacgcattt ttgcccgttg gaaggcgagt cctggcagga cttcctccgc    240
aataacgcca agtcgttccg ctgcgctctg ctgtcccacc gagacggtgc caaagtccat    300
ctcggcacgc gcccgaccga aaagcaatac gagacactgg agaaccagct cgcgttcctg    360
tgccagcaag gcttcagcct ggaaaatgct ctctacgctc tgagcgccgt cggtcacttt    420
accctgggct gcgtgctgga ggaccaagag catcaagtcg caaaagagga gcgcgagacc    480
ccaacaaccg attcgatgcc cccactgctg cgtcaggcaa tcgagctgtt cgatcatcaa    540
ggagccgagc cggcattcct gttcggcttg gagctgatta tctgcggatt ggaaaagcaa    600
ctgaaatgcg agtcgggctc gggccccgcg tacagccgcg cgcgtacgaa aaacaattac    660
gggtctacca tcgagggcct gctcgatctc ccggacgacg acgcccccga agaggcgggg    720
ctggcggctc cgcgcctgtc ctttctcccc gcgggacaca cgcgcagact gtcgacggcc    780
cccccgaccg atgtcagcct gggggacgag ctccacttag acggcgagga cgtggcgatg    840
gcgcatgccg acgcgctaga cgatttcgat ctggacatgt tgggggacgg ggattccccg    900
ggtccgggat ttacccccca cgactccgcc ccctacggcg ctctggatat ggccgacttc    960
gagtttgagc agatgtttac cgatgccctt ggaattgacg agtacggtgg g            1011
```

<210> SEQ ID NO 4
<211> LENGTH: 1011
<212> TYPE: DNA
<213> ORGANISM: Dictyosoma burgeri

<400> SEQUENCE: 4

```
gtcagccgcc tggataagtc caaagtcatc aactccgcgt tggagctgtt gaacgaagtt     60
ggcattgagg gactgacgac ccgcaagttg gcgcagaagc tgggcgtgga gcagcccacc    120
ctctactggc acgtgaagaa taagcgggcg ctgctggatg ccctggccat cgagatgctc    180
gaccgccacc acacgcattt ttgcccgttg gaaggcgagt cctggcagga cttcctccgc    240
aataacgcca agtcgttccg ctgcgctctg ctgtcccacc gagacggtgc caaagtccat    300
ctcggcacgc gcccgaccga aaagcaatac gagacactgg agaaccagct cgcgttcctg    360
tgccagcaag gcttcagcct ggaaaatgct ctctacgctc tgagcgccgt cggtcacttt    420
accctgggct gcgtgctgga ggaccaagag catcaagtcg caaaagagga gcgcgagacc    480
ccaacaaccg attcgatgcc cccactgctg cgtcaggcaa tcgagctgtt cgatcatcaa    540
ggagccgagc cggcattcct gttcggcttg gagctgatta tctgcggatt ggaaaagcaa    600
ctgaaatgcg agtcgggctc gggccccgcg tacagccgcg cgcgtacgaa aaacaattac    660
gggtctacca tcgagggcct gctcgatctc ccggacgacg acgcccccga agaggcgggg    720
ctggcggctc cgcgcctgtc ctttctcccc gcgggacaca cgcgcagact gtcgacggcc    780
cccccgaccg atgtcagcct gggggacgag ctccacttag acggcgagga cgtggcgatg    840
gcgcatgccg acgcgctaga cgatttcgat ctggacatgt tgggggacgg ggattccccg    900
ggtccgggat ttacccccca cgactccgcc ccctacggcg ctctggatat ggccgacttc    960
gagtttgagc agatgtttac cgatgccctt ggaattgacg agtacggtgg g            1011
```

<210> SEQ ID NO 5
<211> LENGTH: 151
<212> TYPE: DNA
<213> ORGANISM: Aedes aegypti

<400> SEQUENCE: 5
gatacgacat ttgttgcatc tactttccga agcgttccag cagacacaga cactggccgg 60
acgaggagaa catctccgtc acccgcactc cgtctgcgtc acggtcgcca tgtgccgatt 120
ttcgtacccg gtcacagtcc agctcgccgg a 151

<210> SEQ ID NO 6
<211> LENGTH: 458
<212> TYPE: DNA
<213> ORGANISM: Aedes aegypti

<400> SEQUENCE: 6
ctcaacattc tccgcgcaca ggttggctct attctgtttc acagtttccg gtgcagttgt 60
gacgaactca gacgaatacc cacgattgta tgtccaacct catttttat ctttgtaaac 120 taacgtcgaa aaatctagat actacatttc tgctttgctt catcttacac taatcactag 180
tttgaacttg cgggttttcc gttatgcttt gtaaatatgc gatgctttag agttttcttc 240
gttccgattc ttctttgcat tcgattgctt cttccgtcga atcgatctga tcttcgtggt 300
ttattcttgt ttcggttcga cctttgccgc agcgcagtgg gtcgtgctga tcgtgtaaaa 360
agtctatcat ccggactggc gcgtcgtact gcgcaactct acaccgtcga acatgttcag 420
attgtgcaat cgtgagtatt cattgaccac ggcttgac 458

<210> SEQ ID NO 7
<211> LENGTH: 469
<212> TYPE: DNA
<213> ORGANISM: Aedes aegypti

<400> SEQUENCE: 7
tgcaaatgct gtttaacgat aatagcgaca tgcagccatt ctggggctac cacgtgagct 60
ctacttgtga gacagcgttc ctaaagagtg tgaaagtgca aacaagtgat gaaaccaata 120
gtgcaaagca agtttcagag ggaaaattta aaaaatgcaa aacagcagta gtacttaact 180
ttgaagattg tgtttcgaaa gccgaagtga ggctgttcca tctgccaccg gaaaaaaacg 240
acgacagcag aatcatcaac aagcaacatc catccgaaaa aatccgggaa accggatctt 300
caaccaacca tcctacaatc tacaaaccag agattatatc tcttcaatcg tttccgacat 360
cggtcggttt cggtgcccaa aatgatctga taaacactta tctctctgta gcttgcatgc 420
cattgcgagc gtattttggt agctggccgt tgccaaacgg ctccgacag 469

<210> SEQ ID NO 8
<211> LENGTH: 886
<212> TYPE: DNA
<213> ORGANISM: Aedes aegypti

<400> SEQUENCE: 8
tacttatcaa ggcatgtatg tatgttgttt gaagcaactg tataactgtt tgaaactatc 60
taattggtga gctcgtttca tttagtatat aataatgata attgctatgg agacgttatt 120
tactagcaag tgatttgacg acctgaaatc ggaacaaata gacaacgttt ttataaatac 180
aataaatcag aactttccat tattgggtac aaagagttgc gctatttcga tactgtcaga 240
tcagattttc cagcacaacg ataccttgat atgcgataac ttagaattag accttcaaat 300

```
ccatctctcc agctatgaac agtcatatag ataaagccaa tggcgttatg aggtagcgga    360

aagcgtcatc tttccaatgc tatctaagta cataatttgc tatagctttc tattaatcgt    420

agtttgagag atgcaaagtc agttatctcg tatcaaggtt tgattgtttt ggaaattagc    480

taaacagttg acattatcac ccgtctttag gggataagcg catacaaatg tgtatttagt    540

tgttcattga agtaacgtaa gataggcaag tatggaaacg agctcaccaa acgtcgaaat    600

acgtctaata aatttgtgtt cagcaggatg gttcaaaatt tatttgcatc acctcaaaat    660

tacagtacct agtgctgttt gtgacaaaca tcaaaaggta aaatcaaact cgtggcgtcg    720

tgcaatctcc atagaatgaa caatttctaa ccgtatttga tggaaagaca ttgagtatac    780

taacctctta acagcattac acttttctat aaacaataaa taatttgttc tattttacat    840

tttctttccc cactttcgcc ccccaataat tcaatccctc aaacag                   886
```

<210> SEQ ID NO 9
<211> LENGTH: 558
<212> TYPE: DNA
<213> ORGANISM: Aedes aegypti

<400> SEQUENCE: 9

```
gtactgctat tggaggttgt gcacgaccac gttgagtttg ccttttgagt tggagagtgt     60

gtcttttcgt catatattcg gccttttcaa gggtgatttt caggctacgt aatgattgta    120

tagtttaacc agctaaaaca tattgatgac aagttctatt tcagcaccac aaacaagcct    180

gttaatgtct ctcaccgcaa ccattgttct gcgcgcgtta taatcagcat agaagtttat    240

tttctttggg atgattcaaa tattacgtga cgcaaagttt gccaatttta gaacccctcc    300

ctcctccacg taacggcttt tgtgtgaaaa atttaaattt tgtgtataga ccgtagcatt    360

tcggaagacc ccctccctta ctctgttgag ttacgtaaaa tttcaacgat ccttttgtag    420

ttctgaattt tatatcagcg tgcagtgtta tgaagatatc cacagtataa aatattattt    480

tattttaaat tctatgctga ttatcaatgt gttactagtg gcttttcata ctcatgttgc    540

gagctcgatt tggcgcac                                                  558
```

<210> SEQ ID NO 10
<211> LENGTH: 209
<212> TYPE: DNA
<213> ORGANISM: Aedes aegypti

<400> SEQUENCE: 10

```
gtcattataa gcttccttag catccacggg tgaaagtcga tcgacggaag cctgcaagac     60

tctgtcgatg ggctttcgtc ctagaagaat aagattaaac ctgaaatgta ttctcccgtg    120

gaatggtttc atttgagtaa ttctgtatct tctccttccc aattccacga acgcgacgaa    180

ctctaataca aacaacataa tgaccacag                                      209
```

<210> SEQ ID NO 11
<211> LENGTH: 584
<212> TYPE: DNA
<213> ORGANISM: Aedes aegypti

<400> SEQUENCE: 11

```
ggtcggtggt gcgtcgatcg tcgcaagttt atcgttaaac agtcaataaa atgagcattt     60

tatatcgtga tacatatgag aagatagagg tttcaattaa aacaaatcca catggtgtcg    120

ctaataaaat tgtgcatttt aagcgagtta tatcctctga tcaagataaa atagaaaatt    180
```

```
cgatttttga atattcaatt ataagagcct gaataactac aacatgtagt gaatcgaaac    240

tgatttatga cggtttgtga aggttacacg tcctaagcat ttggattcaa gaaaagcaag    300

agatatgacg aatgtaaact ttatcgtatc aatgaagtaa ctagcgtcca gaacagtaca    360

aaccaacatc gtaccgtcgt attccactcc ggtcgttgca atatctctag gtccaccgaa    420

aaacactcat gaccaagatc gtgtcgtcga tcttggtcca ccgaaacacc gatgtccata    480

tcgtttcgtc gaacttggac caacgattca tgcaactgat gacaacgcgg cccccgggtc    540

gtaccaatat ccgaaaaatc caactgttct tctctgcctc gcag                     584
```

<210> SEQ ID NO 12
<211> LENGTH: 591
<212> TYPE: DNA
<213> ORGANISM: Aedes aegypti

<400> SEQUENCE: 12

```
gtatgggggt tcttaccggt tgggactgtt tccgaggtat cgatcgggtg tcactcactt     60

cctgggtgct cccattttgt aactgctaac gcttattatt gagtttcagg acatctggga    120

tcttcggtcg acggagtcta ttcccaacag tgccctggat caaacactgc catcatgcag    180

tttccgtagc ctgttgggct acgctccccg acttgacatc ccccattctt atcaaacaac    240

aactcaaggc ctgagacaac gagtggtgga atttgcgcac gaagtcattg gtttgtcctg    300

gtaaaagtta aaagggttaa ctggagggtt aattgacacg gtttcaactg atggccttat    360

tgacacacgg atgaaagact tgcacgcttg accttctgtc tgtactaata aaagttacgt    420

tggctgggtt ttggggtcat aatggcccca aaatcgaatc gtcataactt cttgaaatac    480

aactcacgtt taagaccatt caagagtatt agatcatcgt ctataatagc agatttgaaa    540

tttacttcac atttcggtat tgcagtgccc cttgcttcca caatggaatt a             591
```

<210> SEQ ID NO 13
<211> LENGTH: 135
<212> TYPE: DNA
<213> ORGANISM: Aedes aegypti

<400> SEQUENCE: 13

```
acgacgaact tgtcaaacga tctcaatggc tcctggagaa gctgcgatac ccctgggaga     60

tgatgcccct gatgtacgtg atactgaaag gcgccgacgg agacgtcaat aaagcgcgcc    120

aacggattga cgaag                                                     135
```

<210> SEQ ID NO 14
<211> LENGTH: 296
<212> TYPE: DNA
<213> ORGANISM: Artificial Sequence
<220> FEATURE:
<223> OTHER INFORMATION: Synthetic sequence with 7 TetO sequence motifs from Tn10

<400> SEQUENCE: 14

```
tcgagtttac cactccctat cagtgataga gaaaagtgaa agtcgagttt accactccct     60

atcagtgata gagaaaagtg aaagtcgagt ttaccactcc ctatcagtga tagagaaaag    120

tgaaagtcga gtttaccact ccctatcagt gatagagaaa agtgaaagtc gagtttacca    180

ctccctatca gtgatagaga aaagtgaaag tcgagtttac cactccctat cagtgataga    240

gaaaagtgaa agtcgagttt accactccct atcagtgata gagaaaagtg aaagtc        296
```

<210> SEQ ID NO 15

```
<211> LENGTH: 184
<212> TYPE: DNA
<213> ORGANISM: Trichoplusia ni

<400> SEQUENCE: 15

taagaggcgc ggtaaaccgc aaatggttat gtattataat caaactaaag gcggagtgga     60

cacgctagac caaatgtgtt ctgtgatgac ctgcagtagg aagacgaata ggtggcctat    120

ggcattattg tacggaatga taaacattgc ctgcataaat tcttttatta tatacagcca    180

taat                                                                 184


<210> SEQ ID NO 16
<211> LENGTH: 309
<212> TYPE: DNA
<213> ORGANISM: Trichoplusia ni

<400> SEQUENCE: 16

ccctagaaag atagtctgcg taaaattgac gcatgcattc ttgaaatatt gctctctctt     60

tctaaatagc gcgaatccgt cgctgtgcat ttaggacatc tcagtcgccg cttggagctc    120

ccgtgaggcg tgcttgtcaa tgcggtaagt gtcactgatt ttgaactata acgaccgcgt    180

gagtcaaaat gacgcatgat tatcttttac gtgactttta agatttaact catacgataa    240

ttatattgtt atttcatgtt ctacttacgt gataacttat tatatatata ttttcttgtt    300

atagatatc                                                            309


<210> SEQ ID NO 17
<211> LENGTH: 509
<212> TYPE: DNA
<213> ORGANISM: Autographa californica nucleopolyhedrovirus

<400> SEQUENCE: 17

gctttacgag tagaattcta cgcgtaaaac acaatcaagt atgagtcata agctgatgtc     60

atgttttgca cacggctcat aaccgaactg gctttacgag tagaattcta cttgtaacgc    120

acgatcagtg gatgatgtca tttgtttttc aaatcgagat gatgtcatgt tttgcacacg    180

gctcataaac tcgctttacg agtagaattc tacgtgtaac gcacgatcga ttgatgagtc    240

atttgttttg caatatgata tcatacaata tgactcattt gtttttcaaa accgaacttg    300

atttacgggt agaattctac ttgtaaagca caatcaaaaa gatgatgtca tttgtttttc    360

aaaactgaac tcgctttacg agtagaattc tacgtgtaaa acacaatcaa gaaatgatgt    420

catttgttat aaaaataaaa gctgatgtca tgttttgcac atggctcata actaaactcg    480

ctttacgggt agaattctac gcgtaaaac                                      509


<210> SEQ ID NO 18
<211> LENGTH: 630
<212> TYPE: DNA
<213> ORGANISM: Autographa californica nucleopolyhedrovirus

<400> SEQUENCE: 18

gttgcacaac actattatcg atttgcagtt cgggacataa atgtttaaat atatcgatgt     60

ctttgtgatg cgcgcgacat ttttgtaggt tattgataaa atgaacggat acgttgcccg    120

acattatcat taaatccttg gcgtagaatt tgtcgggtcc attgtccgtg tgcgctagca    180

tgcccgtaac ggacctcgta cttttggctt caaaggtttt gcgcacagac aaaatgtgcc    240

acacttgcag ctctgcatgt gtgcgcgtta ccacaaatcc caacggcgca gtgtacttgt    300

tgtatgcaaa taaatctcga taaaggcgcg gcgcgcgaat gcagctgatc acgtacgctc    360
```

```
ctcgtgttcc gttcaaggac ggtgttaccg acctcagatt aatgtttatc ggccgactgt    420

tttcgtatcc gctcaccaaa cgcgtttttg cattaacatt gtatgtcggc ggatgttcta    480

tatctaattt gaataaataa acgataaccg cgttggtttt agagggcata ataaaagaaa    540

tattgttatc gtgttcgcca ttagggcagt ataaattgac gttcatgttg gatattgttt    600

cagttgcaag ttgacactgg cggcgacaag                                     630


<210> SEQ ID NO 19
<211> LENGTH: 63
<212> TYPE: DNA
<213> ORGANISM: Artificial Sequence
<220> FEATURE:
<223> OTHER INFORMATION: Synthetic sequence

<400> SEQUENCE: 19

gtaagttttc ccgttctttt ctgggttctt cccttttgct catccttgct gcactacctt     60

cag                                                                   63


<210> SEQ ID NO 20
<211> LENGTH: 42
<212> TYPE: DNA
<213> ORGANISM: Artificial Sequence
<220> FEATURE:
<223> OTHER INFORMATION: Synthetic sequence

<400> SEQUENCE: 20

agagtcgatc ccaccccacc caagaagaag cgcaaaccgg tc                        42


<210> SEQ ID NO 21
<211> LENGTH: 33
<212> TYPE: DNA
<213> ORGANISM: Artificial Sequence
<220> FEATURE:
<223> OTHER INFORMATION: Synthetic sequence

<400> SEQUENCE: 21

cgacccaaga aaaagcggaa ggtggaggac ccg                                  33


<210> SEQ ID NO 22
<211> LENGTH: 228
<212> TYPE: DNA
<213> ORGANISM: Simian virus 40

<400> SEQUENCE: 22

taagatacat tgatgagttt ggacaaacca caactagaat gcagtgaaaa aaatgcttta     60

tttgtgaaat ttgtgatgct attgctttat ttgtaaccat tataagctgc aataaacaag    120

ttaacaacaa caattgcatt cattttatgt ttcaggttca gggggaggtg tgggaggttt    180

tttaaagcaa gtaaaacctc tacaaatgtg gtatggctga ttatgatc                 228


<210> SEQ ID NO 23
<211> LENGTH: 130
<212> TYPE: DNA
<213> ORGANISM: Drosophila melanogaster

<400> SEQUENCE: 23

gcagattgtt tagcttgttc agctgcgctt gtttatttgc ttagctttcg cttagcgacg     60

tgttcacttt gcttgtttga attgaattgt cgctccgtag acgaagcgcc tctatttata    120

ctccggcgct                                                           130
```

<210> SEQ ID NO 24
<211> LENGTH: 858
<212> TYPE: DNA
<213> ORGANISM: Escherichia coli

<400> SEQUENCE: 24

```
atgagtattc aacatttccg tgtcgccctt attccctttt ttgcggcatt ttgccttcct      60

gtttttgctc acccagaaac gctggtgaaa gtaaaagatg ctgaagatca gttgggtgca     120

cgagtgggtt acatcgaact ggatctcaac agcggtaaga tccttgagag ttttcgcccc     180

gaagaacgtt ttccaatgat gagcactttt aaagttctgc tatgtggcgc ggtattatcc     240

cgtattgacg ccgggcaaga gcaactcggt cgccgcatac actattctca gaatgacttg     300

gttgagtact caccagtcac agaaaagcat cttacggatg gcatgacagt aagagaatta     360

tgcagtgctg ccataaccat gagtgataac actgcggcca acttacttct gacaacgatc     420

ggaggaccga aggagctaac cgcttttttg cacaacatgg gggatcatgt aactcgcctt     480

gatcgttggg aaccggagct gaatgaagcc ataccaaacg acgagcgtga caccacgatg     540

cctgtagcaa tggcaacaac gttgcgcaaa ctattaactg gcgaactact tactctagct     600

tcccggcaac aattaataga ctggatggag gcggataaag ttgcaggacc acttctgcgc     660

tcggcccttc cggctggctg gtttattgct gataaatctg gagccggtga gcgtgggtct     720

cgcggtatca ttgcagcact ggggccagat ggtaagccct cccgtatcgt agttatctac     780

acgacgggga gtcaggcaac tatggatgaa cgaaatagac agatcgctga gataggtgcc     840

tcactgatta agcattgg                                                   858
```

<210> SEQ ID NO 25
<211> LENGTH: 589
<212> TYPE: DNA
<213> ORGANISM: Escherichia coli

<400> SEQUENCE: 25

```
ttcttgagat cctttttttc tgcgcgtaat ctgctgcttg caaacaaaaa aaccaccgct      60

accagcggtg gtttgtttgc cggatcaaga gctaccaact ctttttccga aggtaactgg     120

cttcagcaga gcgcagatac caaatactgt ccttctagtg tagccgtagt taggccacca     180

cttcaagaac tctgtagcac cgcctacata cctcgctctg ctaatcctgt taccagtggc     240

tgctgccagt ggcgataagt cgtgtcttac cgggttggac tcaagacgat agttaccgga     300

taaggcgcag cggtcgggct gaacgggggg ttcgtgcaca cagcccagct tggagcgaac     360

gacctacacc gaactgagat acctacagcg tgagcattga gaaagcgcca cgcttcccga     420

agggagaaag gcggacaggt atccggtaag cggcagggtc ggaacaggag agcgcacgag     480

ggagcttcca gggggaaacg cctggtatct ttatagtcct gtcgggtttc gccacctctg     540

acttgagcgt cgatttttgt gatgctcgtc aggggggcgg agcctatgg                 589
```

<210> SEQ ID NO 26
<211> LENGTH: 12741
<212> TYPE: DNA
<213> ORGANISM: Artificial Sequence
<220> FEATURE:
<223> OTHER INFORMATION: Synthetic vector construct

<400> SEQUENCE: 26

```
ccctagaaag atagtctgcg taaaattgac gcatgcattc ttgaaatatt gctctctctt      60

tctaaatagc gcgaatccgt cgctgtgcat ttaggacatc tcagtcgccg cttggagctc     120
```

```
ccgtgaggcg tgcttgtcaa tgcggtaagt gtcactgatt ttgaactata acgaccgcgt   180

gagtcaaaat gacgcatgat tatcttttac gtgactttta agatttaact catacgataa   240

ttatattgtt atttcatgtt ctacttacgt gataacttat tatatatata ttttcttgtt   300

atagatatct accgggtgta tcatagcgat gcggccactc gagaaattga actggcttta   360

cgagtagaat tctacgcgta aaacacaatc aagtatgagt cataagctga tgtcatgttt   420

tgcacacggc tcataaccga actggcttta cgagtagaat tctacttgta acgcacgatc   480

agtggatgat gtcatttgtt tttcaaatcg agatgatgtc atgttttgca cacggctcat   540

aaactcgctt tacgagtaga attctacgtg taacgcacga tcgattgatg agtcatttgt   600

tttgcaatat gatatcatac aatatgactc atttgttttt caaaaccgaa cttgatttac   660

gggtagaatt ctacttgtaa agcacaatca aaaagatgat gtcatttgtt tttcaaaact   720

gaactcgctt tacgagtaga attctacgtg taaaacacaa tcaagaaatg atgtcatttg   780

ttataaaaat aaaagctgat gtcatgtttt gcacatggct cataactaaa ctcgctttac   840

gggtagaatt ctacgcgtaa aacatgattg ataattaaat aattcatttg caagctatac   900

gttaaatcaa acggacgctc gaggttgcac aacactatta tcgatttgca gttcgggaca   960

taaatgttta aatatatcga tgtctttgtg atgcgcgcga catttttgta ggttattgat  1020

aaaatgaacg gatacgttgc ccgacattat cattaaatcc ttggcgtaga atttgtcggg  1080

tccattgtcc gtgtgcgcta gcatgcccgt aacggacctc gtacttttgg cttcaaaggt  1140

tttgcgcaca gacaaaatgt gccacacttg cagctctgca tgtgtgcgcg ttaccacaaa  1200

tcccaacggc gcagtgtact tgttgtatgc aaataaatct cgataaaggc gcggcgcgcg  1260

aatgcagctg atcacgtacg ctcctcgtgt tccgttcaag gacggtgtta ccgacctcag  1320

attaatgttt atcggccgac tgttttcgta tccgctcacc aaacgcgttt ttgcattaac  1380

attgtatgtc ggcggatgtt ctatatctaa tttgaataaa taaacgataa ccgcgttggt  1440

tttagagggc ataataaaag aaatattgtt atcgtgttcg ccattagggc agtataaatt  1500

gacgttcatg ttggatattg tttcagttgc aagttgacac tggcggcgac aagacaattc  1560

taattggggt aagttttccc gttcttttct gggttcttcc cttttgctca tccttgctgc  1620

actaccttca ggtgcaagtt gagattcagg ccaccatggg taccgctaga gtcgatccca  1680

ccccacccaa gaagaagcgc aaaccggtcg ccaccatggc ctcctccgag aacgtcatca  1740

ccgagttcat gcgcttcaag gtgcgcatgg agggcaccgt gaacggccac gagttcgaga  1800

tcgagggcga gggcgagggc cgcccctacg agggccacaa caccgtgaag ctgaaggtga  1860

ccaagggcgg cccccctgccc ttcgcctggg acatcctgtc cccccagttc cagtacggct  1920

ccaaggtgta cgtgaagcac cccgccgaca tccccgacta caagaagctg tccttccccg  1980

agggcttcaa gtgggagcgc gtgatgaact tcgaggacgg cggcgtggcg accgtgaccc  2040

aggactcctc cctgcaggac ggctgcttca tctacaaggt gaagttcatc ggcgtgaact  2100

tcccctccga cggccccgtg atgcagaaga agaccatggg ctgggaggcc tccaccgagc  2160

gcctgtaccc ccgcgacggc gtgctgaagg gcgagaccca caaggccctg aagctgaagg  2220

acggcggcca ctacctggtg gagttcaagt ccatctacat ggccaagaag cccgtgcagc  2280

tgcccggcta ctactacgtg gacgccaagc tggacatcac ctcccacaac gaggactaca  2340

ccatcgtgga gcagtacgag cgcaccgagg gccgccacca cctgttcctg agatctcgac  2400

ccaagaaaaa gcggaaggtg gaggacccgt aagatccacc ggatctagat aactgatcat  2460
```

```
aatcagccat accacatttg tagaggtttt acttgcttta aaaaacctcc cacacctccc   2520
cctgaacctg aaacataaaa tgaatgcaat tgttgttgtt aacttgttta ttgcagctta   2580
taatggttac aaataaagca atagcatcac aaatttcaca aataaagcat ttttttcact   2640
gcattctagt tgtggtttgt ccaaactcat caatgtatct tatcatgtct ggacctaggt   2700
aagaggcgcg cctacccacc gtactcgtca attccaaggg catcggtaaa catctgctca   2760
aactcgaagt cggccatatc cagagcgccg taggggggcgg agtcgtgggg ggtaaatccc   2820
ggacccgggg aatccccgtc ccccaacatg tccagatcga aatcgtctag cgcgtcggca   2880
tgcgccatcg ccacgtcctc gccgtctaag tggagctcgt cccccaggct gacatcggtc   2940
gggggggccg tcgacagtct gcgcgtgtgt cccgcgggga gaaaggacag gcgcggagcc   3000
gccagccccg cctcttcggg ggcgtcgtcg tccgggagat cgagcaggcc ctcgatggta   3060
gacccgtaat tgtttttcgt acgcgcgcgg ctgtacgcgg ggcccgagcc cgactcgcat   3120
ttcagttgct tttccaatcc gcagataatc agctccaagc cgaacaggaa tgccggctcg   3180
gctccttgat gatcgaacag ctcgattgcc tgacgcagca gtgggggcat cgaatcggtt   3240
gttggggtct cgcgctcctc ttttgcgact tgatgctctt ggtcctccag cacgcagccc   3300
agggtaaagt gaccgacggc gctcagagcg tagagagcat tttccaggct gaagccttgc   3360
tggcacagga acgcgagctg gttctccagt gtctcgtatt gcttttcggt cgggcgcgtg   3420
ccgagatgga ctttggcacc gtctcggtgg gacagcagag cgcagcggaa cgacttggcg   3480
ttattgcgga ggaagtcctg ccaggactcg ccttccaacg ggcaaaaatg cgtgtggtgg   3540
cggtcgagca tctcgatggc cagggcatcc agcagcgccc gcttattctt cacgtgccag   3600
tagagggtgg gctgctccac gcccagcttc tgcgccaact tgcgggtcgt cagtccctca   3660
atgccaactt cgttcaacag ctccaacgcg gagttgatga ctttggactt atccaggcgg   3720
ctgacaccac cgcgcaggcg cagcaccagg tgcagggtgc tctccttctg gatgttgtag   3780
tcgctcaggg tgcggccatc ctccagctgg cgtccggcga agatcaggcg ctgctgatcc   3840
ggcgggatgc cctccttgtc ctggatcttg gccttcacgt tctcgatggt atcgctcggc   3900
tccacctcca gggtgatggt cttgccggtc agggtcttga cgaagatctg tccggcgagc   3960
tggactgtga ccgggtacga aaatcggcac atggcgaccg tgacgcagac ggagtgcggg   4020
tgacggagat gttctcctcg tccggccagt gtctgtgtct gctggaacgc ttcggaaagt   4080
agatgcaaca aatgtcgtat cctgtttgag ggattgaatt attgggggc gaaagtgggg   4140
aaagaaaatg taaaatagaa caaattattt attgtttata gaaaagtgta atgctgttaa   4200
gaggttagta tactcaatgt ctttccatca aatacggtta gaaattgttc attctatgga   4260
gattgcacga cgccacgagt ttgattttac cttttgatgt ttgtcacaaa cagcactagg   4320
tactgtaatt ttgaggtgat gcaaataaat tttgaaccat cctgctgaac acaaatttat   4380
tagacgtatt tcgacgtttg gtgagctcgt ttccatactt gcctatctta cgttacttca   4440
atgaacaact aaatacacat ttgtatgcgc ttatccccta aagacgggtg ataatgtcaa   4500
ctgtttagct aatttccaaa acaatcaaac cttgatacga gataactgac tttgcatctc   4560
tcaaactacg attaatagaa agctatagca aattatgtac ttagatagca ttggaaagat   4620
gacgctttcc gctacctcat aacgccattg gctttatcta tatgactgtt catagctgga   4680
gagatggatt tgaaggtcta attctaagtt atcgcatatc aaggtatcgt tgtgctggaa   4740
aatctgatct gacagtatcg aaatagcgca actctttgta cccaataatg gaaagttctg   4800
atttattgta tttataaaaa cgttgtctat ttgttccgat ttcaggtcgt caaatcactt   4860
```

-continued

```
gctagtaaat aacgtctcca tagcaattat cattattata tactaaatga aacgagctca   4920
ccaattagat agtttcaaac agttatacag ttgcttcaaa caacatacat acatgccttg   4980
ataagtaccg tgcgccaaat cgagctcgca acatgagtat gaaaagccac tagtaacaca   5040
ttgataatca gcatagaatt taaaataaaa taatatttta tactgtggat atcttcataa   5100
cactgcacgc tgatataaaa ttcagaacta caaaaggatc gttgaaattt tacgtaactc   5160
aacagagtaa gggagggggt cttccgaaat gctacggtct atacacaaaa tttaaatttt   5220
tcacacaaaa gccgttacgt ggaggaggga ggggttctaa aattggcaaa ctttgcgtca   5280
cgtaatattt gaatcatccc aaagaaaata aacttctatg ctgattataa cgcgcgcaga   5340
acaatggttg cggtgagaga cattaacagg cttgtttgtg gtgctgaaat agaacttgtc   5400
atcaatatgt tttagctggt taaactatac aatcattacg tagcctgaaa atcacccttg   5460
aaaaggccga atatatgacg aaaagacaca ctctccaact caaaaggcaa actcaacgtg   5520
gtcgtgcaca acctccaata gcagtacctg tcggagccgt ttggcaacgg ccagctacca   5580
aaatacgctc gcaatggcat gcaagctaca gagagataag tgtttatcag atcattttgg   5640
gcaccgaaac cgaccgatgt cggaaacgat tgaagagata taatctctgg tttgtagatt   5700
gtaggatggt tggttgaaga tccggtttcc cggatttttt cggatggatg ttgcttgttg   5760
atgattctgc tgtcgtcgtt tttttccggt ggcagatgga acagcctcac ttcggctttc   5820
gaaacacaat cttcaaagtt aagtactact gctgttttgc attttttaaa ttttccctct   5880
gaaacttgct ttgcactatt ggtttcatca cttgtttgca ctttcacact ctttaggaac   5940
gctgtctcac aagtagagct cacgtggtag ccccagaatg gctgcatgtc gctattatcg   6000
ttaaacagca tttgcactgt ggtcattatg ttgtttgtat tagagttcgt cgcgttcgtg   6060
gaattgggaa ggagaagata cagaattact caaatgaaac cattccacgg gagaatacat   6120
ttcaggttta atcttattct tctaggacga aagcccatcg acagagtctt gcaggcttcc   6180
gtcgatcgac tttcacccgt ggatgctaag gaagcttata atgacctcaa cattctccgc   6240
gcacaggttg gctctattct gtttcacagt ttccggtgca gttgtgacga actcagacga   6300
atacccacga ttgtatgtcc aacctcattt tttatctttg taaactaacg tcgaaaaatc   6360
tagatactac atttctgctt tgcttcatct tacactaatc actagtttga acttgcgggt   6420
tttccgttat gctttgtaaa tatgcgatgc tttagagttt tcttcgttcc gattcttctt   6480
tgcattcgat tgcttcttcc gtcgaatcga tctgatcttc gtggtttatt cttgtttcgg   6540
ttcgaccttt gccgcagcgc agtgggtcgt gctgatcgtg taaaaagtct atcatccgga   6600
ctggcgcgtc gtactgcgca actctacacc gtcgaacatg ttcagattgt gcaatcgtga   6660
gtattcattg accacggctt gacctgcgag gcagagaaga acagttggat ttttcggata   6720
ttggtacgac ccgggggccg cgttgtcatc agttgcatga atcgttggtc caagttcgac   6780
gaaacgatat ggacatcggt gtttcggtgg accaagatcg acgacacgat cttggtcatg   6840
agtgtttttc ggtggaccta gagatattgc aacgaccgga gtggaatacg acggtacgat   6900
gttggtttgt actgttctgg acgctagtta cttcattgat acgataaagt ttacattcgt   6960
catatctctt gcttttcttg aatccaaatg cttaggacgt gtaaccttca caaaccgtca   7020
taaatcagtt tcgattcact acatgttgta gttattcagg ctcttataat tgaatattca   7080
aaaatcgaat tttctatttt atcttgatca gaggatataa ctcgcttaaa atgcacaatt   7140
ttattagcga caccatgtgg atttgtttta attgaaacct ctatcttctc atatgtatca   7200
```

-continued

```
cgatataaaa tgctcatttt attgactgtt taacgataaa cttgcgacga tcgacgcacc   7260
accgacctaa ttccattgtg gaagcaaggg gcactgcaat accgaaatgt gaagtaaatt   7320
tcaaatctgc tattatagac gatgatctaa tactcttgaa tggtcttaaa cgtgagttgt   7380
atttcaagaa gttatgacga ttcgattttg ggccattat gaccccaaaa cccagccaac   7440
gtaactttta ttagtacaga cagaaggtca agcgtgcaag tctttcatcc gtgtgtcaat   7500
aaggccatca gttgaaaccg tgtcaattaa ccctccagtt aacccttta actttacca   7560
ggacaaacca atgacttcgt gcgcaaattc caccactcgt tgtctcaggc cttgagttgt   7620
tgtttgataa gaatgggga tgtcaagtcg gggagcgtag cccaacaggc tacggaaact   7680
gcatgatggc agtgtttgat ccagggcact gttgggaata gactccgtcg accgaagatc   7740
ccagatgtcc tgaaactcaa taataagcgt tagcagttac aaaatgggag cacccaggaa   7800
gtgagtgaca cccgatcgat acctcggaaa cagtcccaac cggtaagaac cccatacct   7860
tcgtcaatcc gttggcgcgc tttattgacg tctccgtcgg cgcctttcag tatcacgtac   7920
atcaggggca tcatctccca ggggtatcgc agcttctcca ggagccattg agatcgtttg   7980
acaagttcgt cgtccatggt ggcagattgt ttagcttgtt cagctgcgct tgtttatttg   8040
cttagctttc gcttagcgac gtgttcactt tgcttgtttg aattgaattg tcgctccgta   8100
gacgaagcgc ctctatttat actccggcgc tcgttttcga gtttaccact ccctatcagt   8160
gatagagaaa agtgaaagtc gagtttacca ctccctatca gtgatagaga aaagtgaaag   8220
tcgagtttac cactccctat cagtgataga gaaaagtgaa agtcgagttt accactccct   8280
atcagtgata gagaaaagtg aaagtcgagt ttaccactcc ctatcagtga tagagaaaag   8340
tgaaagtcga gtttaccact ccctatcagt gatagagaaa agtgaaagtc gagtttacca   8400
ctccctatca gtgatagaga aaagtgaaag tcgaaacctg gctagcagat ctcatatgat   8460
taagaggcgc ggtaaaccgc aaatggttat gtattataat caaactaaag gcggagtgga   8520
cacgctagac caaatgtgtt ctgtgatgac ctgcagtagg aagacgaata ggtggcctat   8580
ggcattattg tacggaatga taaacattgc ctgcataaat tcttttatta tatacagcca   8640
taatgtcagt agcaagggag aaaaggtcca aagtcgcaaa aaatttatga gaaaccttta   8700
catgagcctg acgtcatcgt ttatgcgtaa gcgtttagaa gctcctactt tgaagagata   8760
tttgcgcgat aatatctcta atattttgcc aaatgaagtg cctggtacat cagatgacag   8820
tactgaagag ccagtaatga aaaaacgtac ttactgtact tactgcccct ctaaaataag   8880
gcgaaaggca aatgcatcgt gcaaaaaatg caaaaaagtt atttgtcgag agcataaatat   8940
tgatatgtgc caaagttgtt tctgactgac taataagtat aatttgtttc tattatgtat   9000
aagttaagct aattacttat tttataatac aacatgactg tttttaaagt acaaaataag   9060
tttatttttg taaaagagag aatgtttaaa agttttgtta ctttatagaa gaaattttga   9120
gtttttgttt ttttttaata aataaataaa cataaataaa ttgtttgttg aatttattat   9180
tagtatgtaa gtgtaaatat aataaaactt aatatctatt caaattaata aataaacctc   9240
gatatacaga ccgataaaac acatgcgtca attttacgca tgattatctt taacgtacgt   9300
cacaatatga ttatctttct agggttaaat aatagtttct aattttttta ttattcagcc   9360
tgctgtcgtg aataccgtat atctcaacgc tgtctgtgag attgtcgtat tctagccttt   9420
ttagtttttc gctcatcgac ttgatattgt ccgacacatt ttcgtcgatt tgcgttttga   9480
tcaaagactt gagcagagac acgttaatca actgttcaaa ttgatccata ttaacgatat   9540
caacccgatg cgtatatggt gcgtaaaata tattttttaa ccctcttata ctttgcactc   9600
```

```
tgcgttaata cgcgttcgtg tacagacgta atcatgtttt ctttttttgga taaaactcct   9660
actgagtttg acctcatatt agaccctcac aagttgcaaa acgtggcatt ttttaccaat   9720
gaagaattta aagttatttt aaaaaatttc atcacagatt taaagaagaa ccaaaaatta   9780
aattatttca acagtttaat cgaccagtta atcaacgtgt acacagacgc gtcggcaaaa   9840
aacacgcagc ccgacgtgtt ggctaaaatt attaaatcaa cttgtgttat agtcacggat   9900
ttgccgtcca acgtgttcct caaaaagttg aagaccaaca agtttacgga cactattaat   9960
tatttgattt tgccccactt cattttgtgg gatcacaatt ttgttatatt ttaaacaaag  10020
cttggcactg gccgtcgttt tacaacgtcg tgactgggaa aaccctggcg ttacccaact  10080
taatcgcctt gcagcacatc ccccttttcgc cagctggcgt aatagcgaag aggcccgcac  10140
cgatcgccct tcccaacagt tgcgcagcct gaatggcgaa tggcgcctga tgcggtattt  10200
tctccttacg catctgtgcg gtatttcaca ccgcatatat ggtgcactct cagtacaatc  10260
tgctctgatg ccgcatagtt aagccagccc cgacacccgc caacacccgc tgacgcgccc  10320
tgacgggctt gtctgctccc ggcatccgct tacagacaag ctgtgaccgt ctccgggagc  10380
tgcatgtgtc agaggttttc accgtcatca ccgaaacgcg cgagacgaaa gggcctcgtg  10440
atacgcctat ttttataggt taatgtcatg ataataatgg tttcttagac gtcaggtggc  10500
acttttcggg gaaatgtgcg cggaacccct atttgtttat ttttctaaat acattcaaat  10560
atgtatccgc tcatgagaca ataaccctga taaatgcttc aataatattg aaaaaggaag  10620
agtatgagta ttcaacattt ccgtgtcgcc cttattccct tttttgcggc attttgcctt  10680
cctgtttttg ctcacccaga aacgctggtg aaagtaaaag atgctgaaga tcagttgggt  10740
gcacgagtgg gttacatcga actggatctc aacagcggta agatccttga gagttttcgc  10800
cccgaagaac gttttccaat gatgagcact tttaaagttc tgctatgtgg cgcggtatta  10860
tcccgtattg acgccgggca agagcaactc ggtcgccgca tacactattc tcagaatgac  10920
ttggttgagt actcaccagt cacagaaaag catcttacgg atggcatgac agtaagagaa  10980
ttatgcagtg ctgccataac catgagtgat aacactgcgg ccaacttact tctgacaacg  11040
atcggaggac cgaaggagct aaccgctttt ttgcacaaca tgggggatca tgtaactcgc  11100
cttgatcgtt gggaaccgga gctgaatgaa gccataccaa acgacgagcg tgacaccacg  11160
atgcctgtag caatggcaac aacgttgcgc aaactattaa ctggcgaact acttactcta  11220
gcttcccggc aacaattaat agactggatg gaggcggata aagttgcagg accacttctg  11280
cgctcggccc ttccggctgg ctggtttatt gctgataaat ctggagccgg tgagcgtggg  11340
tctcgcggta tcattgcagc actggggcca gatggtaagc cctcccgtat cgtagttatc  11400
tacacgacgg ggagtcaggc aactatggat gaacgaaata gacagatcgc tgagataggt  11460
gcctcactga ttaagcattg gtaactgtca gaccaagttt actcatatat actttagatt  11520
gatttaaaac ttcattttta atttaaaagg atctaggtga agatcctttt tgataatctc  11580
atgaccaaaa tcccttaacg tgagttttcg ttccactgag cgtcagaccc cgtagaaaag  11640
atcaaaggat cttcttgaga tcctttttttt ctgcgcgtaa tctgctgctt gcaaacaaaa  11700
aaaccaccgc taccagcggt ggtttgtttg ccggatcaag agctaccaac tctttttccg  11760
aaggtaactg gcttcagcag agcgcagata ccaaatactg tccttctagt gtagccgtag  11820
ttaggccacc acttcaagaa ctctgtagca ccgcctacat acctcgctct gctaatcctg  11880
ttaccagtgg ctgctgccag tggcgataag tcgtgtctta ccgggttgga ctcaagacga  11940
```

```
tagttaccgg ataaggcgca gcggtcgggc tgaacggggg gttcgtgcac acagcccagc  12000

ttggagcgaa cgacctacac cgaactgaga tacctacagc gtgagcattg agaaagcgcc  12060

acgcttcccg aagggagaaa ggcggacagg tatccggtaa gcggcagggt cggaacagga  12120

gagcgcacga gggagcttcc agggggaaac gcctggtatc tttatagtcc tgtcgggttt  12180

cgccacctct gacttgagcg tcgatttttg tgatgctcgt caggggggcg gagcctatgg  12240

aaaaacgcca gcaacgcggc ctttttacgg ttcctggcct tttgctggcc ttttgctcac  12300

atgttctttc ctgcgttatc ccctgattct gtggataacc gtattaccgc ctttgagtga  12360

gctgataccg ctcgccgcag ccgaacgacc gagcgcagcg agtcagtgag cgaggaagcg  12420

gaagagcgcc caatacgcaa accgcctctc cccgcgcgtt ggccgattca ttaatgcagc  12480

tggcacgaca ggtttcccga ctggaaagcg ggcagtgagc gcaacgcaat taatgtgagt  12540

tagctcactc attaggcacc ccaggcttta cactttatgc ttccggctcg tatgttgtgt  12600

ggaattgtga gcggataaca atttcacaca ggaaacagct atgaccatga ttacgaattt  12660

cgacgctcgc gcgacttggt ttgccattct ttagcgcgcg tcgcgtcaca cagcttggcc  12720

acaatgtgga tgtcgactta a                                            12741
```

```
<210> SEQ ID NO 27
<211> LENGTH: 1014
<212> TYPE: DNA
<213> ORGANISM: Ceratitis capitata

<400> SEQUENCE: 27

atggtcagcc gcctggataa gtccaaagtc atcaactccg cgttggagct gttgaacgaa     60

gttggcattg agggactgac gacccgcaag ttggcgcaga agctgggcgt ggagcagccc    120

accctctact ggcacgtgaa gaataagcgg gcgctgctgg atgccctggc catcgagatg    180

ctcgaccgcc accacacgca tttttgcccg ttggaaggcg agtcctggca ggacttcctc    240

cgcaataacg ccaagtcgtt ccgctgcgct ctgctgtccc accgagacgg tgccaaagtc    300

catctcggca cgcgcccgac cgaaaagcaa tacgagacac tggagaacca gctcgcgttc    360

ctgtgccagc aaggcttcag cctggaaaat gctctctacg ctctgagcgc cgtcggtcac    420

tttaccctgg gctgcgtgct ggaggaccaa gagcatcaag tcgcaaaaga ggagcgcgag    480

accccaacaa ccgattcgat gcccccactg ctgcgtcagg caatcgagct gttcgatcat    540

caaggagccg agccggcatt cctgttcggc ttggagctga ttatctgcgg attggaaaag    600

caactgaaat gcgagtcggg ctcgggcccc gcctacagcc gcgcccgcac caagaacaac    660

tacggcagca ccatcgaggg cctgctggat ctgccggatg atgatgcccc ggaggaggcg    720

ggcctggccg ccccgcgcct gagcttcctg ccggccggac acacccgccg cctgtcgacc    780

gccccgccga ccgacgtgag cctgggcgat gagctgcacc tggatggcga ggatgtggcg    840

atggcccacg ccgatgccct ggacgacttc gacctggaca tgctgggcga tggcgatagc    900

ccgggaccgg gattcacccc gcacgatagc gccccctacg gcgccctgga tatggccgat    960

ttcgagttcg agcagatgtt caccgacgcc ctgggcatcg atgagtacgg cggc          1014

<210> SEQ ID NO 28
<211> LENGTH: 1008
<212> TYPE: DNA
<213> ORGANISM: Ceratitis capitata
```

<400> SEQUENCE: 28

```
atggtcagcc gcctggacaa gagcaaggtg atcaacagcg ccctggagct gctgaacgaa      60
gtgggcatcg agggcctgac cacccgcaag ctggcccaga agctgggcgt ggaacagccg     120
accctgtact ggcacgtgaa gaacaagcgc gccctgctgg acgccctggc catcgaaatg     180
ctggatcgcc accacaccca cttctgcccg ctggagggcg agagctggca ggatttcctg     240
cgcaacaacg ccaagagctt ccgctgcgcc ctgctgtcgc accgcgatgg cgccaaggtg     300
cacctgggca cccgcccgac cgagaagcag tacgagaccc tggagaacca gctggccttc     360
ctgtgccagc agggcttcag cctggagaac gccctgtacg ccctgagcgc cgtgggccac     420
ttcaccctgg gctgtgtgct ggaggatcag gagcaccagg tggccaagga ggagcgcgag     480
accccgacca ccgatagcat gccgccgctg ctgcgccagg ccatcgagct gttcgatcac     540
cagggcgccg agccggcctt cctgttcggc ctggagctga tcatctgcgg cctggaaaag     600
cagctgaagt gcgagagcgg cagcgcctac agccgcgccc gtaccaagaa caactatggc     660
agcaccatcg agggactgct ggacctgccg gatgacgatg ccccggagga agccggcctg     720
gccgcccccc gcctgagctt cctgcccgcc ggacacacgc gccgcctgag caccgccccg     780
ccgaccgatg tgagcctggg cgacgagctg cacctggatg gagaggatgt ggcaatggcc     840
cacgccgacg ccctggacga tttcgacctg gatatgctgg gcgatggaga tagcccggga     900
ccgggcttca cgccccacga tagcgccccg tacggcgccc tggacatggc cgacttcgag     960
ttcgagcaaa tgttcaccga cgcgctgggc atcgatgagt atggcggg                 1008
```

<210> SEQ ID NO 29
<211> LENGTH: 337
<212> TYPE: PRT
<213> ORGANISM: Ceratitis capitata

<400> SEQUENCE: 29

```
Val Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175
```

```
Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285

Phe Asp Leu Asp Met Leu Gly Asp Gly Asp Ser Pro Gly Pro Gly Phe
    290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly


<210> SEQ ID NO 30
<211> LENGTH: 238
<212> TYPE: PRT
<213> ORGANISM: Dictyosoma burgeri

<400> SEQUENCE: 30

Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205
```

```
Thr Ile Val Glu Gln Tyr Glu Arg Thr Glu Gly Arg His His Leu Phe
    210                 215                 220

Leu Arg Ser Arg Pro Lys Lys Lys Arg Lys Val Glu Asp Pro
225                 230                 235


<210> SEQ ID NO 31
<211> LENGTH: 20
<212> TYPE: PRT
<213> ORGANISM: Artificial Sequence
<220> FEATURE:
<223> OTHER INFORMATION: Artificial leader peptide

<400> SEQUENCE: 31

Met Gly Thr Ala Arg Val Asp Pro Thr Pro Pro Lys Lys Lys Arg Lys
1               5                   10                  15

Pro Val Ala Thr
            20


<210> SEQ ID NO 32
<211> LENGTH: 76
<212> TYPE: PRT
<213> ORGANISM: Ceratitis capitata

<400> SEQUENCE: 32

Met Asp Asp Glu Leu Val Lys Arg Ser Gln Trp Leu Leu Glu Lys Leu
1               5                   10                  15

Arg Tyr Pro Trp Glu Met Met Pro Leu Met Tyr Val Ile Leu Lys Gly
            20                  25                  30

Ala Asp Gly Asp Val Asn Lys Ala Arg Gln Arg Ile Asp Glu Gly Gln
        35                  40                  45

Ala Val Val Asn Glu Tyr Ser Arg Leu His Asn Leu Asn Met Phe Asp
    50                  55                  60

Gly Val Glu Leu Arg Ser Thr Thr Arg Gln Ser Gly
65                  70                  75


<210> SEQ ID NO 33
<211> LENGTH: 665
<212> TYPE: PRT
<213> ORGANISM: Artificial Sequence
<220> FEATURE:
<223> OTHER INFORMATION: Fusion of Drosophila melanogaster Ubiquitin
      with Ceratitis capitata tTAV

<400> SEQUENCE: 33

Met Asp Asp Glu Leu Val Lys Arg Ser Gln Trp Leu Leu Glu Lys Leu
1               5                   10                  15

Arg Tyr Pro Trp Glu Met Met Pro Leu Met Tyr Val Ile Leu Lys Gly
            20                  25                  30

Ala Asp Gly Asp Val Asn Lys Ala Arg Gln Arg Ile Asp Glu Val Gln
        35                  40                  45

Met Leu Phe Asn Asp Asn Ser Asp Met Gln Pro Phe Trp Gly Tyr His
    50                  55                  60

Val Ser Ser Thr Cys Glu Thr Ala Phe Leu Lys Ser Val Lys Val Gln
65                  70                  75                  80

Thr Ser Asp Glu Thr Asn Ser Ala Lys Gln Val Ser Glu Gly Lys Phe
                85                  90                  95

Lys Lys Cys Lys Thr Ala Val Val Leu Asn Phe Glu Asp Cys Val Ser
            100                 105                 110
```

```
Lys Ala Glu Val Arg Leu Phe His Leu Pro Pro Glu Lys Asn Asp Asp
        115                 120                 125

Ser Arg Ile Ile Asn Lys Gln His Pro Ser Glu Lys Ile Arg Glu Thr
    130                 135                 140

Gly Ser Ser Thr Asn His Pro Thr Ile Tyr Lys Pro Glu Ile Ile Ser
145                 150                 155                 160

Leu Gln Ser Phe Pro Thr Ser Val Gly Phe Gly Ala Gln Asn Asp Leu
                165                 170                 175

Ile Asn Thr Tyr Leu Ser Val Ala Cys Met Pro Leu Arg Ala Tyr Phe
            180                 185                 190

Gly Ser Trp Pro Leu Pro Asn Gly Ser Asp Arg Ile Arg His Leu Leu
        195                 200                 205

His Leu Leu Ser Glu Ala Phe Gln Gln Thr Gln Thr Leu Ala Gly Arg
    210                 215                 220

Gly Glu His Leu Arg His Pro His Ser Val Cys Val Thr Val Ala Met
225                 230                 235                 240

Cys Arg Phe Ser Tyr Pro Val Thr Val Gln Leu Ala Gly Gln Ile Phe
                245                 250                 255

Val Lys Thr Leu Thr Gly Lys Thr Ile Thr Leu Glu Val Glu Pro Ser
            260                 265                 270

Asp Thr Ile Glu Asn Val Lys Ala Lys Ile Gln Asp Lys Glu Gly Ile
        275                 280                 285

Pro Pro Asp Gln Gln Arg Leu Ile Phe Ala Gly Arg Gln Leu Glu Asp
    290                 295                 300

Gly Arg Thr Leu Ser Asp Tyr Asn Ile Gln Lys Glu Ser Thr Leu His
305                 310                 315                 320

Leu Val Leu Arg Leu Arg Gly Gly Val Ser Arg Leu Asp Lys Ser Lys
                325                 330                 335

Val Ile Asn Ser Ala Leu Glu Leu Leu Asn Glu Val Gly Ile Glu Gly
            340                 345                 350

Leu Thr Thr Arg Lys Leu Ala Gln Lys Leu Gly Val Glu Gln Pro Thr
        355                 360                 365

Leu Tyr Trp His Val Lys Asn Lys Arg Ala Leu Leu Asp Ala Leu Ala
    370                 375                 380

Ile Glu Met Leu Asp Arg His His Thr His Phe Cys Pro Leu Glu Gly
385                 390                 395                 400

Glu Ser Trp Gln Asp Phe Leu Arg Asn Asn Ala Lys Ser Phe Arg Cys
                405                 410                 415

Ala Leu Leu Ser His Arg Asp Gly Ala Lys Val His Leu Gly Thr Arg
            420                 425                 430

Pro Thr Glu Lys Gln Tyr Glu Thr Leu Glu Asn Gln Leu Ala Phe Leu
        435                 440                 445

Cys Gln Gln Gly Phe Ser Leu Glu Asn Ala Leu Tyr Ala Leu Ser Ala
    450                 455                 460

Val Gly His Phe Thr Leu Gly Cys Val Leu Glu Asp Gln Glu His Gln
465                 470                 475                 480

Val Ala Lys Glu Glu Arg Glu Thr Pro Thr Thr Asp Ser Met Pro Pro
                485                 490                 495

Leu Leu Arg Gln Ala Ile Glu Leu Phe Asp His Gln Gly Ala Glu Pro
            500                 505                 510

Ala Phe Leu Phe Gly Leu Glu Leu Ile Ile Cys Gly Leu Glu Lys Gln
        515                 520                 525
```

```
Leu Lys Cys Glu Ser Gly Ser Gly Pro Ala Tyr Ser Arg Ala Arg Thr
    530                 535                 540

Lys Asn Asn Tyr Gly Ser Thr Ile Glu Gly Leu Leu Asp Leu Pro Asp
545                 550                 555                 560

Asp Asp Ala Pro Glu Glu Ala Gly Leu Ala Ala Pro Arg Leu Ser Phe
                565                 570                 575

Leu Pro Ala Gly His Thr Arg Arg Leu Ser Thr Ala Pro Pro Thr Asp
            580                 585                 590

Val Ser Leu Gly Asp Glu Leu His Leu Asp Gly Glu Asp Val Ala Met
        595                 600                 605

Ala His Ala Asp Ala Leu Asp Asp Phe Asp Leu Asp Met Leu Gly Asp
    610                 615                 620

Gly Asp Ser Pro Gly Pro Gly Phe Thr Pro His Asp Ser Ala Pro Tyr
625                 630                 635                 640

Gly Ala Leu Asp Met Ala Asp Phe Glu Phe Glu Gln Met Phe Thr Asp
                645                 650                 655

Ala Leu Gly Ile Asp Glu Tyr Gly Gly
            660                 665


<210> SEQ ID NO 34
<211> LENGTH: 337
<212> TYPE: PRT
<213> ORGANISM: Ceratitis capitata

<400> SEQUENCE: 34

Val Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Asp Ala Pro Glu Glu Ala Gly
225                 230                 235                 240
```

```
Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285

Phe Asp Leu Asp Met Leu Gly Asp Gly Asp Ser Pro Gly Pro Gly Phe
    290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly


<210> SEQ ID NO 35
<211> LENGTH: 103
<212> TYPE: PRT
<213> ORGANISM: Ceratitis capitata

<400> SEQUENCE: 35

Met Asp Asp Glu Leu Val Lys Arg Ser Gln Trp Leu Leu Glu Lys Leu
1               5                   10                  15

Arg Tyr Pro Trp Glu Met Met Pro Leu Met Tyr Val Ile Leu Lys Gly
            20                  25                  30

Ala Asp Gly Asp Val Asn Lys Ala Arg Gln Arg Ile Asp Glu Gly Tyr
        35                  40                  45

Asp Ile Cys Cys Ile Tyr Phe Pro Lys Arg Ser Ser Arg His Arg His
    50                  55                  60

Trp Pro Asp Glu Glu Asn Ile Ser Val Thr Arg Thr Pro Ser Ala Ser
65                  70                  75                  80

Arg Ser Pro Cys Ala Asp Phe Arg Thr Arg Ser Gln Ser Ser Ser Pro
                85                  90                  95

Asp Arg Ser Ser Ser Arg Pro
            100


<210> SEQ ID NO 36
<211> LENGTH: 1627
<212> TYPE: DNA
<213> ORGANISM: Artificial Sequence
<220> FEATURE:
<223> OTHER INFORMATION: Insertion of synthetic contruct in Aedes
      aegypti chromosome

<400> SEQUENCE: 36

cttcaaagtc tcatccccat tgccataaag cctattcagt ttccccaaaa gtgtactgaa      60

acagtgatta ttttaaacct ccgcctatag ttaaatttcg gtgcgacatt ccacgataaa     120

tacatttcag gcagaatttg acgtcatagt cccagtattt cagcgataag actcatttgt     180

acttccgtga gatgtttcta taatatgaaa acactgataa ataattaaat ttaaaaaaaa     240

aatccattag ataaaatttt acgctgttgc tgcgcacgaa acacagttgc tggtttgaaa     300

agttatcaaa atgcgttgca ttgttattca atgaatggaa tactcaagta gacttgttag     360

atgtttcaaa gatgctgtat ttagaaagaa taaacacatc ttaaagataa tcatgcgtaa     420

aattgacgca tgtgttttat cggtctgtat atcgaggttt atttattaat ttgaatagat     480

attaagtttt attatattta cacttacata ctaataataa attcaacaaa caatttattt     540
```

```
atgtttattt atttattaaa aaaaaacaaa aactcaaaat ttcttctata aagtaacaaa    600

acttttaaac attctctctt ttacaaaaat aaacttattt tgtactttaa aaacagtcat    660

gttgtattat aaaataagta attagcttaa cttatacata atagaaacaa attatactta    720

ttagtcagtc agaaacaact ttggcacata tcaatattat gctctcgaca aataactttt    780

ttgcattttt tgcacgatgc atttgccttt cgccttattt tagaggggca gtaagtacag    840

taagtacgtt ttttcattac agataatcat gcgtcatttt gactcacgcg gtcgttatag    900

ttcaaaatca gtgacactta ccgcattgac aagcacgcct cacgggagct ccaagcggcg    960

actgagatgt cctaaatgca cagcgacgga ttcgcgctat ttagaaagag agagcaatat   1020

ttcaagaatg catgcgtcaa ttttacgcag actatctttc tagggttaat gaaaaaagag   1080

aacacccggc acggtaaaat gtcaaaaaag tggacttgca atttcattta cagtgaaacc   1140

tccatgagtc gatattgaag ggaccatcga ctcatggaaa tatcgagtca tggaacaaca   1200

atcctttgga aagctgtttc tagggaccat catagtaacc atgaaatttt gtttttagta   1260

tggttccatg agtcgatatc gagtcatgga acatcgactc atggaggtat cactgtacta   1320

tcgttcttgc ttgacccaat ctcaccgcta tttttgatgt tttaaacact gtaccgagaa   1380

aaatgatttt tttaaggaaa aatcaaatag attccggaaa atacgtgtga agtgtaatga   1440

aaagactttc aaccttctac taatagaacg atagaggtta aagtacatgc gtgatacttt   1500

gaacaggaga aatttaatgt tgtaaatttt ctctagtttc aaaatagttt attgatatag   1560

taaacaaata ctactatttc tagaaatgtg tattgtgata aattacgtgt aataaatatgt  1620

tccctaa                                                             1627
```

```
<210> SEQ ID NO 37
<211> LENGTH: 1399
<212> TYPE: DNA
<213> ORGANISM: Artificial Sequence
<220> FEATURE:
<223> OTHER INFORMATION: Synthetic construct inserted into the Aedes
      aegypti chromosome

<400> SEQUENCE: 37
```

```
gaccctaaat tcaaaaacag ataccaggca ctctctctat atgtttcctc cagattacga     60

agattgataa tattttgaaa gaataataaa ttgaaaaaaa tcattatgtt cacatcgatg    120

agtgataaaa agccgtatta aaaaaaatta cgatgatatt tcaaatgaat aataaattca    180

ctagagcagc atttttttagt caatgtgcaa aattattttg aaaaagctta ttgatataac   240

catctaactc tactttgtgt gggaatcatt tcacatttgc cggtcaaaaa ctcaaaaggc    300

ctgttttaat aagcattttc catagctttc tggtgtacgg aatagaggtc aaaagtgagg    360

aagcgtccga aataagaacc atgtaaaggc cacaagtttc tattaaagat aatcatgcgt    420

aaaattgacg catgtgtttt atcggtctgt atatcgaggt ttatttatta atttgaatag    480

atattaagtt ttattatatt tacacttaca tactaataat aaattcaaca aacaatttat    540

ttatgtttat ttatttatta aaaaaaaaca aaaactcaaa atttcttcta taaagtaaca    600

aaacttttaa acattctctc ttttacaaaa ataaacttat tttgtacttt aaaaacagtc    660

atgttgtatt ataaaataag taattagctt aacttataca taatagaaac aaattatact    720

tattagtcag tcagaaacaa ctttggcaca tatcaatatt atgctctcga caaataactt    780

ttttgcattt tttgcacgat gcatttgcct ttcgccttat tttagagggg cagtaagtac    840

agtaagtacg ttttttcatt acagataatc atgcgtcatt ttgactcacg cggtcgttat    900
```

```
agttcaaaat cagtgacact taccgcattg acaagcacgc ctcacgggag ctccaagcgg     960

cgactgagat gtcctaaatg cacagcgacg gattcgcgct atttagaaag agagagcaat    1020

atttcaagaa tgcatgcgtc aattttacgc agactatctt tctagggtta atataaaatt    1080

atgcatgatg cggaagcgta atctttaccc acctttgaaa attcagtgtt tctgcttaat    1140

gaagctgagt tattacacaa aattatttta tgtgctctgt gcagagttat acttatgaga    1200

ccttaaataa ctgttatatg actcagaacg gtattttcat agcttagaac gccaacaaat    1260

agatgtttaa agctaataaa taggattata taaaaattcc cattctttca tccaacatca    1320

tttcataaat caaatttttc aaagaagctg tgcatcagtt gtatttcgtg gaacggatct    1380

ggtgtagtga ttagcacac                                                 1399


<210> SEQ ID NO 38
<211> LENGTH: 21
<212> TYPE: DNA
<213> ORGANISM: Artificial Sequence
<220> FEATURE:
<223> OTHER INFORMATION: Synthetic Primer

<400> SEQUENCE: 38

ctgttgctgc gcacgaaaca c                                                21


<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39

gtcagtcaga aacaactttg gca                                              23


<210> SEQ ID NO 40
<211> LENGTH: 23
<212> TYPE: DNA
<213> ORGANISM: Artificial Sequence
<220> FEATURE:
<223> OTHER INFORMATION: Synthetic primer

<400> SEQUENCE: 40

gcttcattaa gcagaaacac tga                                              23


<210> SEQ ID NO 41
<211> LENGTH: 23
<212> TYPE: DNA
<213> ORGANISM: Artificial Sequence
<220> FEATURE:
<223> OTHER INFORMATION: Synthetic Primer

<400> SEQUENCE: 41

tcagtgtttc tgcttaatga agc                                              23


<210> SEQ ID NO 42
<211> LENGTH: 404
<212> TYPE: DNA
<213> ORGANISM: Aedes aegypti

<400> SEQUENCE: 42

cttcaaagtc tcatccccat tgccataaag cctattcagt ttccccaaaa gtgtactgaa      60

acagtgatta ttttaaacct ccgcctatag ttaaatttcg gtgcgacatt ccacgataaa     120

tacatttcag gcagaatttg acgtcatagt cccagtattt cagcgataag actcatttgt     180
```

```
acttccgtga gatgtttcta taatatgaaa acactgataa ataattaaat ttaaaaaaaa    240

aatccattag ataaaatttt acgctgttgc tgcgcacgaa acacagttgc tggtttgaaa    300

agttatcaaa atgcgttgca ttgttattca atgaatggaa tactcaagta gacttgttag    360

atgtttcaaa gatgctgtat ttagaaagaa taaacacatc ttaa                      404
```

<210> SEQ ID NO 43
<211> LENGTH: 558
<212> TYPE: DNA
<213> ORGANISM: Aedes aegypti

<400> SEQUENCE: 43

```
tgaaaaaaga gaacacccgg cacggtaaaa tgtcaaaaaa gtggacttgc aatttcattt     60

acagtgaaac ctccatgagt cgatattgaa gggaccatcg actcatggaa atatcgagtc    120

atggaacaac aatcctttgg aaagctgttt ctagggacca tcatagtaac catgaaattt    180

tgtttttagt atggttccat gagtcgatat cgagtcatgg aacatcgact catggaggta    240

tcactgtact atcgttcttg cttgacccaa tctcaccgct atttttgatg ttttaaacac    300

tgtaccgaga aaaatgattt ttttaaggaa aaatcaaata gattccggaa aatacgtgtg    360

aagtgtaatg aaaagacttt caaccttcta ctaatagaac gatagaggtt aaagtacatg    420

cgtgatactt tgaacaggag aaatttaatg ttgtaaattt tctctagttt caaaatagtt    480

tattgatata gtaaacaaat actactattt ctagaaatgt gtattgtgat aaattacgtg    540

taataatatg ttccctaa                                                  558
```

<210> SEQ ID NO 44
<211> LENGTH: 406
<212> TYPE: DNA
<213> ORGANISM: Aedes aegypti

<400> SEQUENCE: 44

```
gaccctaaat tcaaaaacag ataccaggca ctctctctat atgtttcctc cagattacga     60

agattgataa tattttgaaa gaataataaa ttgaaaaaaa tcattatgtt cacatcgatg    120

agtgataaaa agccgtatta aaaaaaatta cgatgatatt tcaaatgaat aataaattca    180

ctagagcagc attttttagt caatgtgcaa aattattttg aaaaagctta ttgatataac    240

catctaactc tactttgtgt gggaatcatt tcacatttgc cggtcaaaaa ctcaaaaggc    300

ctgttttaat aagcattttc catagctttc tggtgtacgg aatagaggtc aaaagtgagg    360

aagcgtccga aataagaacc atgtaaaggc cacaagtttc tattaa                    406
```

<210> SEQ ID NO 45
<211> LENGTH: 328
<212> TYPE: DNA
<213> ORGANISM: Aedes aegypti

<400> SEQUENCE: 45

```
tataaaatta tgcatgatgc ggaagcgtaa tctttaccca cctttgaaaa ttcagtgttt     60

ctgcttaatg aagctgagtt attacacaaa attattttat gtgctctgtg cagagttata    120

cttatgagac cttaaataac tgttatatga ctcagaacgg tattttcata gcttagaacg    180

ccaacaaata gatgtttaaa gctaataaat aggattatat aaaaattccc attctttcat    240

ccaacatcat ttcataaatc aaatttttca aagaagctgt gcatcagttg tatttcgtgg    300

aacggatctg gtgtagtgat tagcacac                                       328
```

<210> SEQ ID NO 46
<211> LENGTH: 2880
<212> TYPE: DNA
<213> ORGANISM: Aedes aegypti

<400> SEQUENCE: 46

```
aaataggaaa agtttttcat gggggtattc ttctagaaag ttgaagatac aatgacaagg     60
aatgtatcta gtactaaaca tattgttatt tttattacca tgtggttcat gtaacagttg    120
tcagttcagc gccattttca acttgcatga caaattgtga cacgtttcac gtctttaatt    180
gactcgcaaa aaataaatgt gttttaaatc aaatttccat cagtaagcta taatttttag    240
tattattaca agctgctaac gataaaccag tattttgttt tcatttcata tgaaattttc    300
gatggtctat cttaccccaa aatatatttg tacctggggt aagtgggacc tatcaaaaca    360
aaaaccagaa tcaaaacctt tcgtacacgt ttcatacatt tagctagaga gtagcactaa    420
aacattcaaa caaatgattt ttatcaaaaa agatgaacct caaattacgt aattgcataa    480
aagggagaaa aaaagtgtta ttattcttta ttatttaatt attttttatt tttgaaatac    540
gacttcaaaa ttgaacaaac actcagctga aatttgaaat gtatcatgag aacgattact    600
tttctatgtt gtttgaactt tatttgttat ttctaccaaa ttaagtagtg atggaaaaca    660
attccatccc ataaggtggt tttctgccat gcatataaat aataacaaaa catatttata    720
atttcgtcaa ttattgattg tttatgagct acatttttat taacaactta taaatgatat    780
attttgaaca tgtttaattc ctctttacgc atttattgag gaattttcag ttaatattaa    840
atatgaggtg acatactatt aaattgaggg tttcttccta aaacgtaacg tattttatgg    900
ttgatccctt atgtacatca aatatgtact taaaattaaa aatctattac tgtaatagtt    960
gacttactga tgtggattga cgcatgaaac tggatgtgtc ccacttgccc cgcttagaga   1020
ggtaattgcg tccattcgct cattctaaaa ctttcttcta aggttttcac aatttcgaaa   1080
ttattcgatt agtttcatgc acacaccagc aaatatgttg ccaaaacgtg attgtgttgt   1140
tggaattgaa aaatattgac atttggaaat tttattgaac aatttgtttg aactatcgtt   1200
ttttttcgt tcccacttgc cccgcggtac cttaacttgt ttttgaaaac atgatttcaa    1260
aaccattcac aactgaaaaa tattgacaaa aaacgatgca aacaagaaaa aaatatctaa   1320
gatgtttcac aagtatgata aacccactta aaagaaagat tatactgaaa attgaagagc   1380
tatgagaaaa aatatgtaaa cccaacattt atcgtcaatt cttggttttt ccctcaaatt   1440
gtcttcaaag tctcattccc attgctataa agcccattca gtttccccaa aggtgtactg   1500
aaacagtgat tattttaaac cttcgcaaat agttaaattt cggtgcgaca ttccacgatc   1560
aataaatttc aggcagaagt tgacgtcata attccagtat ttcagcgatc caactcattt   1620
gtacttccgt gagatgtttc tataatataa aaacactgat aaataatcaa atttagaaaa   1680
aaaaacacct ttttgataaa aatttacggt gttgctgcgc acgaaacaca gttgctggtt   1740
tgagaagttg tcaaaatgcg ttgtattgtt attcaatgca cggaatactc aagtagactt   1800
gtttgatgtt tcagagatgc tgtatttaga aagaataaac acatcttaat gaaaaaagag   1860
aacacccggc accgtaaaat gtcaaaaaag tggacttgga attttattta ctatcgttct   1920
tgcttgatcc aatctcaccc ccatttccaa tgttttagac atcgtgccga aacaaatgat   1980
tttttgtgg gaaaatcaaa cagattccgg aaaataccctg tgatgtgtaa tgaaaagact   2040
ttcaacattc tactaataca acgatagagg ctagagtaca tgcgtgatac tttgacagga   2100
gaaatttaat gttgaaaatt ttatttagtt tcaacatgca agtttattgc tgtagtacac   2160
```

```
aaaaactact atttctaaaa atgtatattg ttatgcatta tgtgtaataa tatgttccct   2220

aacatatgaa ttattaattt tagtaatatc tgaaatattt cacaaaacat atttttccgt   2280

tttgacccaa tctcaccccc atcgacggta ttcagttctt tcaaattata tgaatacatt   2340

aaaatcagat ctctaccatc atttctttaa ctcattcggc cgaatgaccc tttcatctta   2400

atgatttatc ggtctgatgt gttttgtcct aacgaacttc tgcttaacga ctcaacaccg   2460

tgaacttctg agtaatccac gaagattgta tttaatattt ttatttattt atttatttat   2520

ttttttttt ttttttgaag cactgcggaa ataatcccta ggtgaaaatg aaatgctaga   2580

taaatactta tggtggtaac ctccattagg gaaatacccc cagacaacca gaagtcgcat   2640

gaaagctcac gtaataactc gttaattcct acaaattaca tcaaacccgc aaaacacggt   2700

gcataaaatc gccagattga tgagtttcct cgcgaaaaac gatttttttt tctgggttca   2760

tttgtacatt ttgtttcgtt ccgtacactc gtacaaagta agtcgaatta atccgtagaa   2820

gctgtcaaat cagcatttgt tatcataagt taagtcgcat atgaccacag gttagttcgg   2880
```

<210> SEQ ID NO 47
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 47

```
catgccgacg cgctaga                                                  17
```

<210> SEQ ID NO 48
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 48

```
ggtaaacatc tgctcaaact cgaagtc                                       27
```

<210> SEQ ID NO 49
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: FAM fluorescent label
<220> FEATURE:
<221> NAME/KEY: misc_feature
<222> LOCATION: (24)..(24)
<223> OTHER INFORMATION: BHQ-1 quencher

<400> SEQUENCE: 49

```
tcgatctgga catgttgggg gacg                                          24
```

<210> SEQ ID NO 50
<211> LENGTH: 25
<212> TYPE: DNA
<213> ORGANISM: Aedes aegypti

<400> SEQUENCE: 50

```
ctgcagtagt gatgaagatg aacca                                         25
```

<210> SEQ ID NO 51
<211> LENGTH: 25
<212> TYPE: DNA
<213> ORGANISM: Aedes aegypti

<400> SEQUENCE: 51
gggcgaaaat gccgtattgt actca 25

<210> SEQ ID NO 52
<211> LENGTH: 27
<212> TYPE: DNA
<213> ORGANISM: Aedes aegypti
<220> FEATURE:
<221> NAME/KEY: misc_feature
<222> LOCATION: (1)..(1)
<223> OTHER INFORMATION: HEX Fluorescent Label
<220> FEATURE:
<221> NAME/KEY: misc_feature
<222> LOCATION: (27)..(27)
<223> OTHER INFORMATION: BHQ-1 Quencher

<400> SEQUENCE: 52
agacaccagt cggacttgca aaatctg 27

<210> SEQ ID NO 53
<211> LENGTH: 23
<212> TYPE: DNA
<213> ORGANISM: Aedes aegypti

<400> SEQUENCE: 53
gcttcattaa gcagaaacac tga 23

<210> SEQ ID NO 54
<211> LENGTH: 28
<212> TYPE: DNA
<213> ORGANISM: Aedes aegypti

<400> SEQUENCE: 54
catctaactc tactttgtgt gggaatca 28

<210> SEQ ID NO 55
<211> LENGTH: 22
<212> TYPE: DNA
<213> ORGANISM: Aedes aegypti

<400> SEQUENCE: 55
tgacaagcac gcctcacggg ag 22

<210> SEQ ID NO 56
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 56
ctgttgctgc gcacgaaaca c 21

<210> SEQ ID NO 57
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 57
gtgccaaagt tgtttctgac tgac 24

<210> SEQ ID NO 58
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 58
gatggtccct agaaacagct ttcc 24

<210> SEQ ID NO 59
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 59
ctgttgctgc gcacgaaaca c 21

<210> SEQ ID NO 60
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 60
tcgatcaact aactgaaatc gatga 25

<210> SEQ ID NO 61
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 61
cctaagaccg ttaacatttc aagtgac 27

<210> SEQ ID NO 62
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 62
cttcgagagt aagcggaaac tcc 23

<210> SEQ ID NO 63
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 63
agtattagca tccgaagctc atgac 25

<210> SEQ ID NO 64

<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 64
gcttcattaa gcagaaacac tga 23

<210> SEQ ID NO 65
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 65
cagaccgata aaacacatgc gtca 24

<210> SEQ ID NO 66
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 66
tcgactcatg gaggtttcac tg 22

<210> SEQ ID NO 67
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 67
atgcgttgca ttgttattca atg 23

<210> SEQ ID NO 68
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 68
aaatatcagc ctcaaataag cactt 25

<210> SEQ ID NO 69
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 69
ctatagcttt ctggtgtacg gaatagag 28

<210> SEQ ID NO 70
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 70
ggtctcataa gtataactct gcacagag 28

<210> SEQ ID NO 71
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 71
tgcagtagtg atgaagatga acca 24

<210> SEQ ID NO 72
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 72
cgaaaatgcc gtattgtact ca 22

<210> SEQ ID NO 73
<211> LENGTH: 402
<212> TYPE: DNA
<213> ORGANISM: Aedes aegypti

<400> SEQUENCE: 73
cttcaaagtc tcatccccat tgccataaag cctattcagt ttccccaaaa gtgtactgaa 60
acagtgatta ttttaaacct ccgcctatag ttaaatttcg gtgcgacatt ccacgataaa 120
tacatttcag gcagaatttg acgtcatagt cccagtattt cagcgataag actcatttgt 180
acttccgtga gatgtttcta taatatgaaa acactgataa ataattaaat ttaaaaaaaa 240
aatccattag ataaaatttt acgctgttgc tgcgcacgaa acacagttgc tggtttgaaa 300
agttatcaaa atgcgttgca ttgttattca atgaatggaa tactcaagta gacttgttag 360
atgtttcaaa gatgctgtat ttagaaagaa taaacacatc tt 402

<210> SEQ ID NO 74
<211> LENGTH: 560
<212> TYPE: DNA
<213> ORGANISM: Aedes aegypti

<400> SEQUENCE: 74
aatgaaaaaa gagaacaccc ggcacggtaa aatgtcaaaa aagtggactt gcaatttcat 60
ttacagtgaa acctccatga gtcgatattg aagggaccat cgactcatgg aaatatcgag 120
tcatggaaca acaatccttt ggaaagctgt ttctagggac catcatagta accatgaaat 180
tttgttttta gtatggttcc atgagtcgat atcgagtcat ggaacatcga ctcatggagg 240
tatcactgta ctatcgttct tgcttgaccc aatctcaccg ctatttttga tgttttaaac 300
actgtaccga gaaaaatgat ttttttaagg aaaaatcaaa tagattccgg aaaatacgtg 360
tgaagtgtaa tgaaaagact ttcaaccttc tactaataga acgatagagg ttaaagtaca 420
tgcgtgatac tttgaacagg agaaatttaa tgttgtaaat tttctctagt ttcaaaatag 480
tttattgata tagtaaacaa atactactat ttctagaaat gtgtattgtg ataaattacg 540
tgtaataata tgttccctaa 560

<210> SEQ ID NO 75
<211> LENGTH: 404
<212> TYPE: DNA
<213> ORGANISM: Aedes aegypti

<400> SEQUENCE: 75
gaccctaaat tcaaaaacag ataccaggca ctctctctat atgtttcctc cagattacga 60
agattgataa tattttgaaa gaataataaa ttgaaaaaaa tcattatgtt cacatcgatg 120
agtgataaaa agccgtatta aaaaaaatta cgatgatatt tcaaatgaat aataaattca 180
ctagagcagc attttttagt caatgtgcaa aattattttg aaaaagctta ttgatataac 240
catctaactc tactttgtgt gggaatcatt tcacatttgc cggtcaaaaa ctcaaaaggc 300
ctgttttaat aagcattttc catagctttc tggtgtacgg aatagaggtc aaaagtgagg 360
aagcgtccga aataagaacc atgtaaaggc cacaagtttc tatt 404

<210> SEQ ID NO 76
<211> LENGTH: 206
<212> TYPE: DNA
<213> ORGANISM: Aedes aegypti

<400> SEQUENCE: 76
aatataaaat tatgcatgat gcggaagcgt aatctttacc cacctttgaa aattcagtgt 60
ttctgcttaa tgaagctgag ttattacaca aaattatttt atgtgctctg tgcagagtta 120
tacttatgag accttaaata actgttatat gactcagaac ggtattttca tagcttagaa 180
cgccaacaaa tagatgttta aagcta 206

<210> SEQ ID NO 77
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 77
aaatgaaatt gcaagtccac ttt 23

<210> SEQ ID NO 78
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 78
gcgtcaattt tacgcagact atc 23

<210> SEQ ID NO 79
<211> LENGTH: 23
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: FAM Fluorescent Label
<220> FEATURE:
<221> NAME/KEY: misc_feature
<222> LOCATION: (23)..(23)
<223> OTHER INFORMATION: BHQ-1 Quencher

<400> SEQUENCE: 79
acacccggca cggtaaaatg tca 23

<210> SEQ ID NO 80
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 80
agcagaaaca ctgaattttc aaag 24

<210> SEQ ID NO 81
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 81
gcgtcaattt tacgcagact atc 23

<210> SEQ ID NO 82
<211> LENGTH: 27
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: FAM Fluorescent label
<220> FEATURE:
<221> NAME/KEY: misc_feature
<222> LOCATION: (27)..(27)
<223> OTHER INFORMATION: BHQ-1 Quencher

<400> SEQUENCE: 82
atgatgcgga agcgtaatct ttaccca 27

<210> SEQ ID NO 83
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 83
tgcagtagtg atgaagatga acca 24

<210> SEQ ID NO 84
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 84
cgaaaatgcc gtattgtact ca 22

<210> SEQ ID NO 85
<211> LENGTH: 27
<212> TYPE: DNA
<213> ORGANISM: Artificial Sequence
<220> FEATURE:

-continued

```
<223> OTHER INFORMATION: Oligonucleotide primer
<220> FEATURE:
<221> NAME/KEY: misc_feature
<222> LOCATION: (1)..(1)
<223> OTHER INFORMATION: HEX Fluorescent label
<220> FEATURE:
<221> NAME/KEY: misc_feature
<222> LOCATION: (27)..(27)
<223> OTHER INFORMATION: BHQ-1 Quencher

<400> SEQUENCE: 85

agacaccagt cggacttgca aaatctg                                          27
```